(12) United States Patent
Johansson et al.

(10) Patent No.: US 9,157,070 B2
(45) Date of Patent: Oct. 13, 2015

(54) METHODS AND COMBINATION COMPRISING EUKARYOTIC CELLS AND RECOMBINANT SPIDER SILK PROTEIN

(75) Inventors: Jan Johansson, Stockholm (SE); Anna Rising, Uppsala (SE); My Hedhammar, Stockholm (SE); Ulrika Johansson, Uppsala (SE); Mona Widhe, Uppsala (SE)

(73) Assignee: SPIBER TECHNOLOGIES AB, Uppsala (SE)

( * ) Notice: Subject to any disclaimer, the term of this patent is extended or adjusted under 35 U.S.C. 154(b) by 0 days.

(21) Appl. No.: 13/639,763

(22) PCT Filed: Apr. 12, 2011

(86) PCT No.: PCT/SE2011/050448
§ 371 (c)(1),
(2), (4) Date: Jan. 17, 2013

(87) PCT Pub. No.: WO2011/129756
PCT Pub. Date: Oct. 20, 2011

(65) Prior Publication Data
US 2013/0115698 A1    May 9, 2013

Related U.S. Application Data

(60) Provisional application No. 61/323,226, filed on Apr. 12, 2010.

(30) Foreign Application Priority Data

Apr. 12, 2010   (EP) .................................... 10159694
Feb. 7, 2011    (EP) .................................... 11153543

(51) Int. Cl.
| | |
|---|---|
| C12N 5/00 | (2006.01) |
| C12N 5/071 | (2010.01) |
| A61L 27/22 | (2006.01) |
| A61L 27/38 | (2006.01) |
| A61L 27/56 | (2006.01) |
| C07K 14/005 | (2006.01) |
| C07K 14/435 | (2006.01) |
| D01F 4/02 | (2006.01) |
| C12N 5/0735 | (2010.01) |
| C12N 5/0797 | (2010.01) |
| C12N 5/0789 | (2010.01) |
| C12N 5/077 | (2010.01) |

(52) U.S. Cl.
CPC ............ *C12N 5/0691* (2013.01); *A61L 27/227* (2013.01); *A61L 27/3804* (2013.01); *A61L 27/3834* (2013.01); *A61L 27/56* (2013.01); *C07K 14/005* (2013.01); *C07K 14/43518* (2013.01); *C12N 5/0068* (2013.01); *C12N 5/0606* (2013.01); *C12N 5/067* (2013.01); *C12N 5/0623* (2013.01); *C12N 5/0629* (2013.01); *C12N 5/0647* (2013.01); *C12N 5/0656* (2013.01); *C12N 5/0676* (2013.01); *D01F 4/02* (2013.01); *C12N 2500/82* (2013.01); *C12N 2533/50* (2013.01); *C12N 2539/00* (2013.01)

(58) Field of Classification Search
IPC ......................................................... C12N 5/00
See application file for complete search history.

(56) References Cited

U.S. PATENT DOCUMENTS

2008/0293919 A1* 11/2008 Kaplan et al. ................. 530/356

FOREIGN PATENT DOCUMENTS

| WO | WO 2006/002827 A1 | 1/2006 |
|---|---|---|
| WO | WO 2007/078239 A2 | 7/2007 |
| WO | WO 2007/103135 A2 | 9/2007 |
| WO | WO 2008/154547 A2 | 12/2008 |

OTHER PUBLICATIONS

Fredriksson et al. Tissue Response to Subcutaneously Implanted Recombinant Spider Silk: An In Vivo Study; Materials, vol. 2 (2009) pp. 1908-1922.*
Hillerdal, C. O. Laminin Motifs Inserted Into a Recombinant Spider Drag-Line Silk Protein Increase the Proliferation of Human Dermal Fibroblasts; Swedish University of Agricultural Sciences (2009) downloaded from http://stud.epsilon.slu.se/835/1/hillerdal_1__100203.pdf.*
Stark et al. Macroscopic Fibers Self-Assembled From Recombinant Miniature Spider Silk Proteins; Biomacromolecules, vol. 8 (2007) pp. 1695-1701.*
Askarieh et al., "Self-assembly of spider silk proteins is controlled by a pH-sensitive relay", Nature, vol. 465, May 13, 2010, pp. 236-239.
Cheung et al., "Natural fibre-reinforced composites for bioengineering and environmental engineering applications", Composites: Part B 40, 2009, pp. 655-663.
Hardy et al., "Polymeric materials based on silk proteins", Polymer 49, 2008, pp. 4309-4327.

(Continued)

*Primary Examiner* — Sharmila G. Landau
*Assistant Examiner* — Paul Martin
(74) *Attorney, Agent, or Firm* — Birch, Stewart, Kolasch & Birch, LLP

(57) ABSTRACT

A method and a combination for the cultivation of eukaryotic cells are provided, as well as a method for preparation of eukaryotic cells. The methods comprise providing a sample of eukaryotic cells to be cultured, applying said sample to a cell scaffold material; and maintaining said cell scaffold material having cells applied thereto under conditions suitable for cell culture. The combination comprises eukaryotic cells and a cell scaffold material. The cell scaffold material comprises a polymer of a spider silk protein.

5 Claims, 59 Drawing Sheets

(56) References Cited

OTHER PUBLICATIONS

Hedhammar et al., "Sterilized Recombinant Spider Silk Fibers of Low Pyrogenicity", Biomacromolecules, 2009, 7 pages.
Hedhammar et al., "Structural Properties of Recombinant Nonrepetitive and Repetitive Parts of Major Ampullate Spidroin 1 from Euprosthenops australis: Implications for Fiber Formation", Biochemistry, 47(11), 2008, pp. 3407-3417.
International Search Report for PCT/SE2011/050448 dated Jul. 18, 2011.
Rising, "Spider Dragline Silk Molecular Properties and Recombinant Expression", Faculty of Veterinary Medicine and Animal Science Department of Biomedical Sciences and Veterinary Public Health and Department of Anatomy, Physiology and Biochemistry Uppsala, 2007, 52 pages.
SEQ ID No. 9 in WO2007/078239 A2, (2007).
Wang et al., "Fibrous proteins and tissue engineering", materialstoday, vol. 9, No. 12, Dec. 2006, pp. 44-53.
Wang et al., "In vitro cartilage tissue engineering with 3D porous aqueous-derived silk scaffolds and mesenchymal stem cells", Biomaterials 26, 2005, pp. 7082-7094.
Bini, E. et al, "RGD-Functionalized Bioengineered Spider Dragline Silk Biomaterial," Biomacromolecules, Nov. 1 2006, vol. 7, No. 11, pp. 3139-3145.
Extended European Search Report for Appl. No. 11769173.3 dated Sep. 23, 2013.
Grip, S. et al., "Engineered disulfides improve mechanical properties of recombinant spider silk," Protein Science, Jan. 1, 2009, vol. 18, pp. 1012-1022.
Hedhammer, M. et al, "Sterilized Recombinant Spider Silk Fibers of Low Pyrogenicity," Biomacromolecules, Mar. 17, 2010, vol. 11, No. 4, pp. 953-959.
Lewicka, M. et al, "Spider silk matrices for neural stem cell cultures," Abstracts of the Annual Meeting of the Society for Neuroscience, Nov. 25, 2011, vol. 41, pp. 1-2.
Morgan, A.W. et al, "Characterization and optimization of RGD-containing silk blends to support osteoblastic differentiation," Biomaterials, Mar. 5, 2008, vol. 29, No. 16, pp. 2556-2563.
Widhe, M. et al, "Invited Review: Current Progess and Limitations of Spider Silk for Biomedical Applications," Biopolymers, Jan. 1, 2012, vol. 97, No. 6, pp. 468-478.
Widhe, M. et al, "Recombinant spider silk as matrices for cell culture," Biomaterials, Aug. 24, 2010, vol. 31, No. 36, pp. 9575-9585.
Widhe, M. et al, "Recombinant spider silk with cell binding motifs for specific adherence of cells," Biomaterials, Nov. 1, 2013, vol. 34, No. 33, pp. 8223-8234.
European Office Action for Appl. No. 11769173.3 dated Aug. 11, 2015.
Meinel, L., "Engineering of bone and cartilage like tissue at the interface of drug delivery and biomaterials," XP 55205149, Aug. 1, 2006, http://e-collection.library.ethz.ch/eserv/eth:29782/eth-29782-01.pdf.
Wu. S. et al, "Spider silk for xeno-free long-term self-renewal and differentiation of human pluripotent stem cells," Biomaterials, Jul. 17, 2014, vol. 35, No. 30, pp. 8496-8502.

* cited by examiner

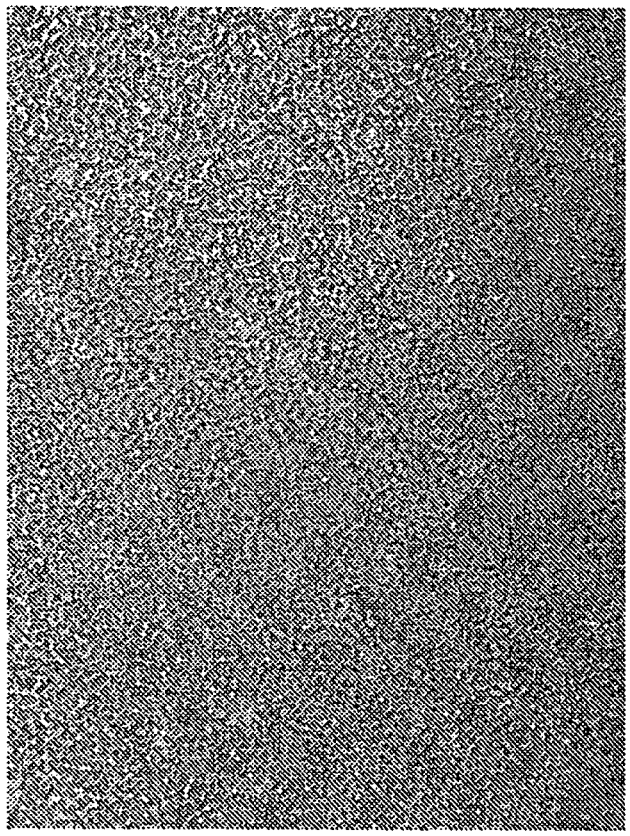
FIGURE 8

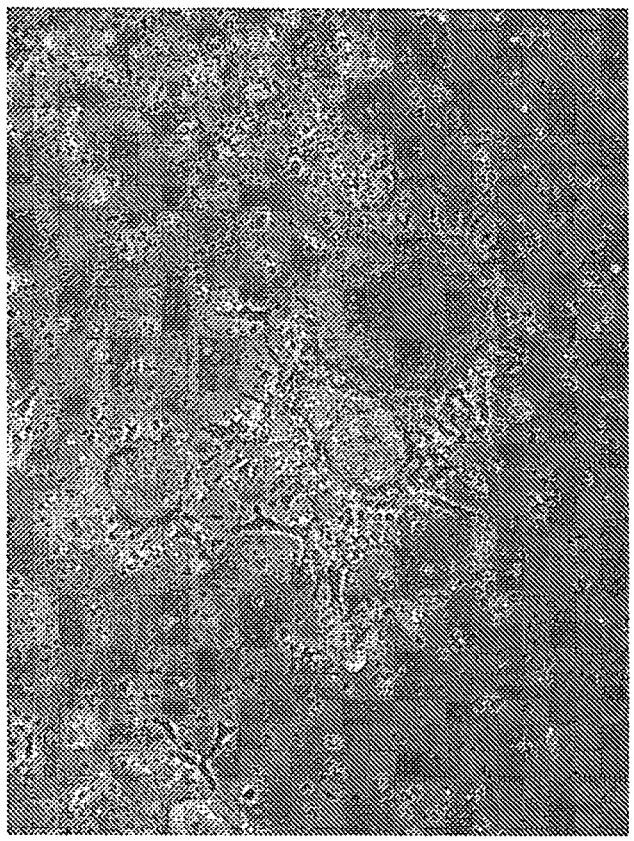
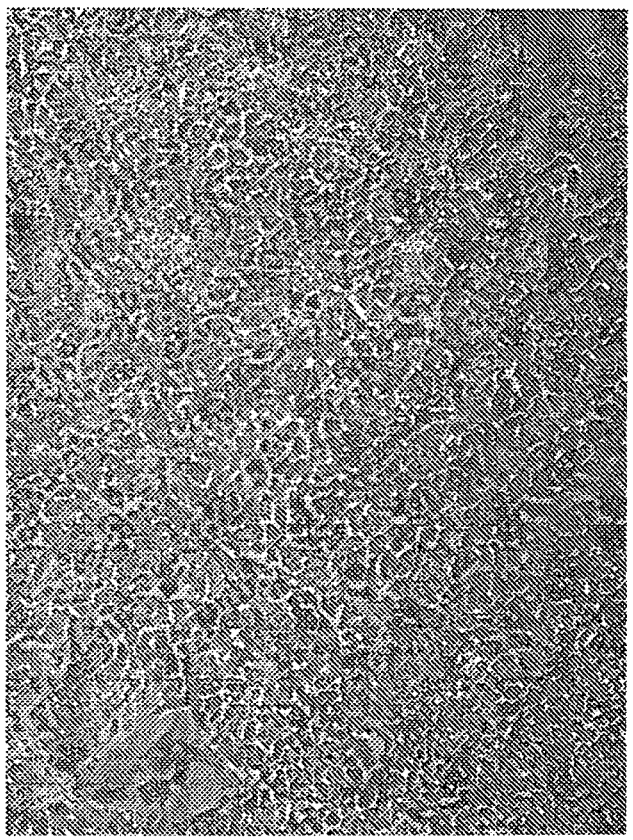
FIGURE 9

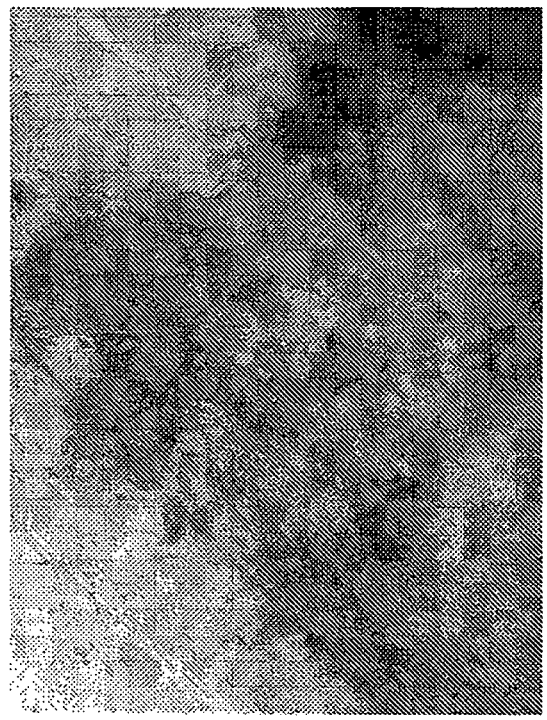
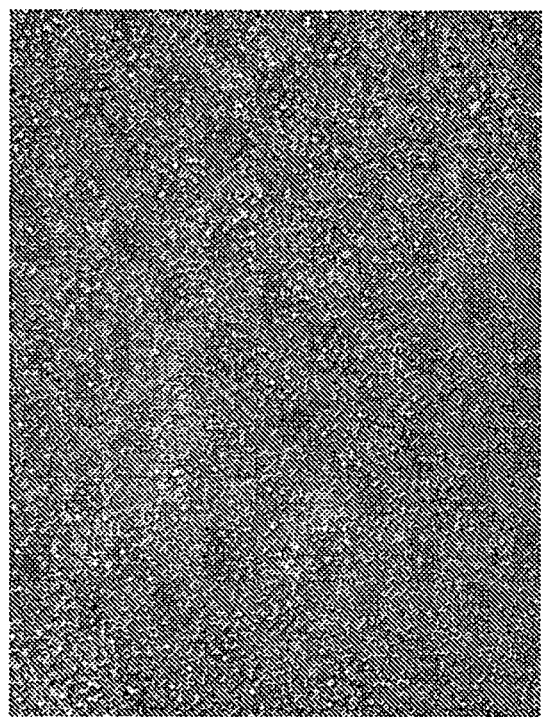
FIGURE 11

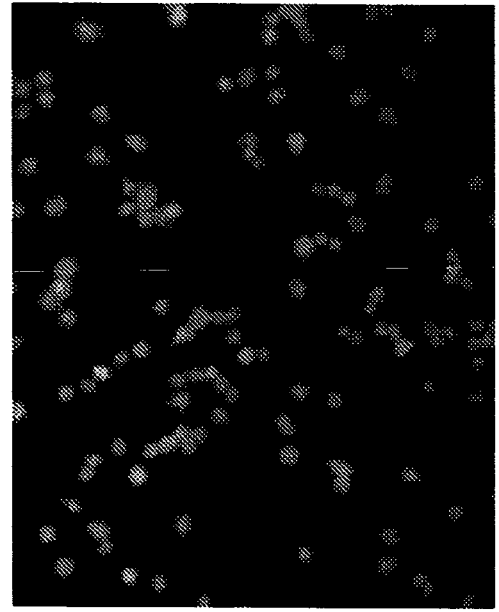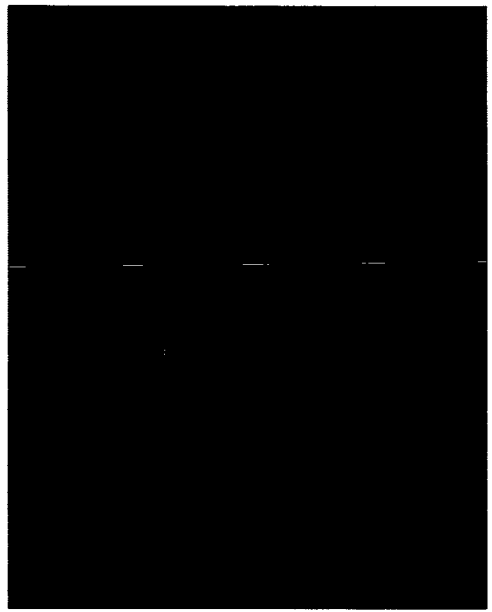
FIGURE 17

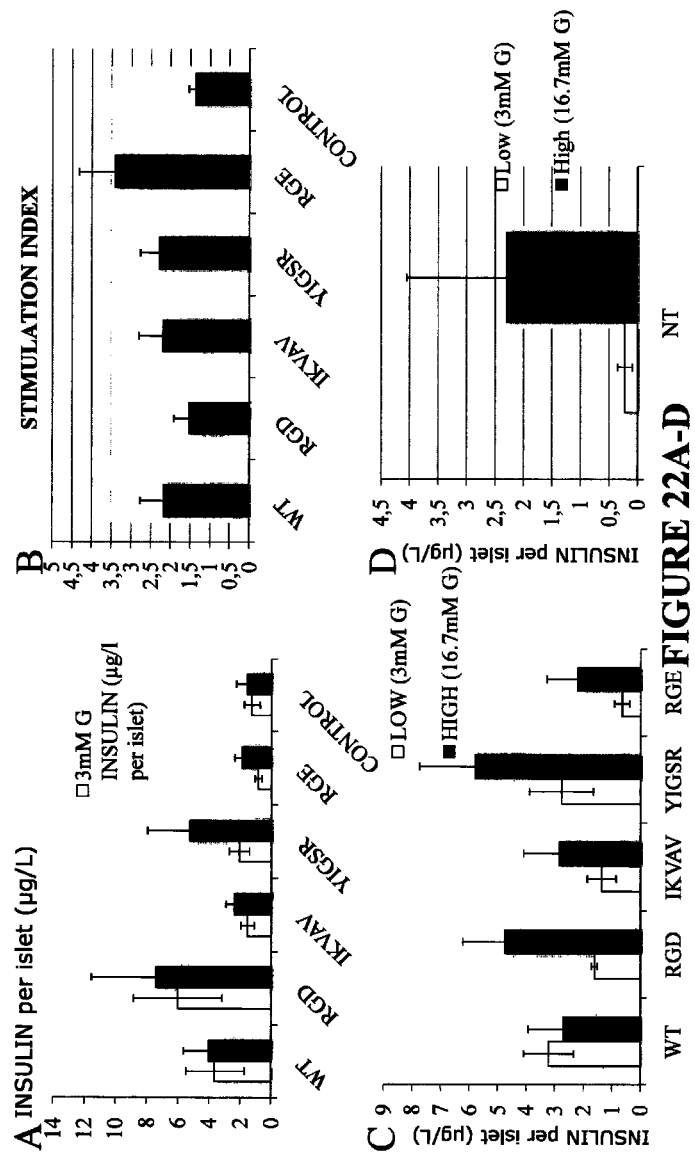
FIGURE 22A-D

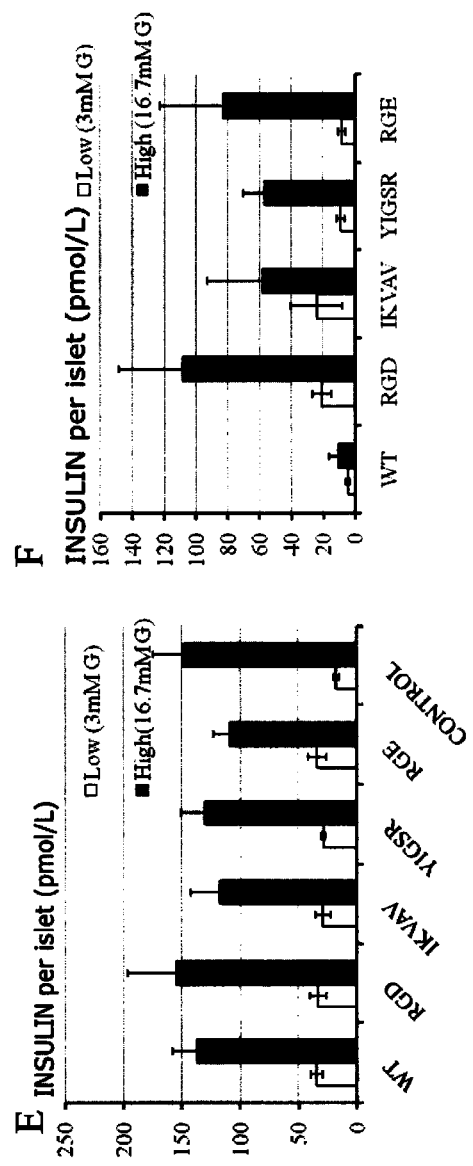
FIGURE 22E-F

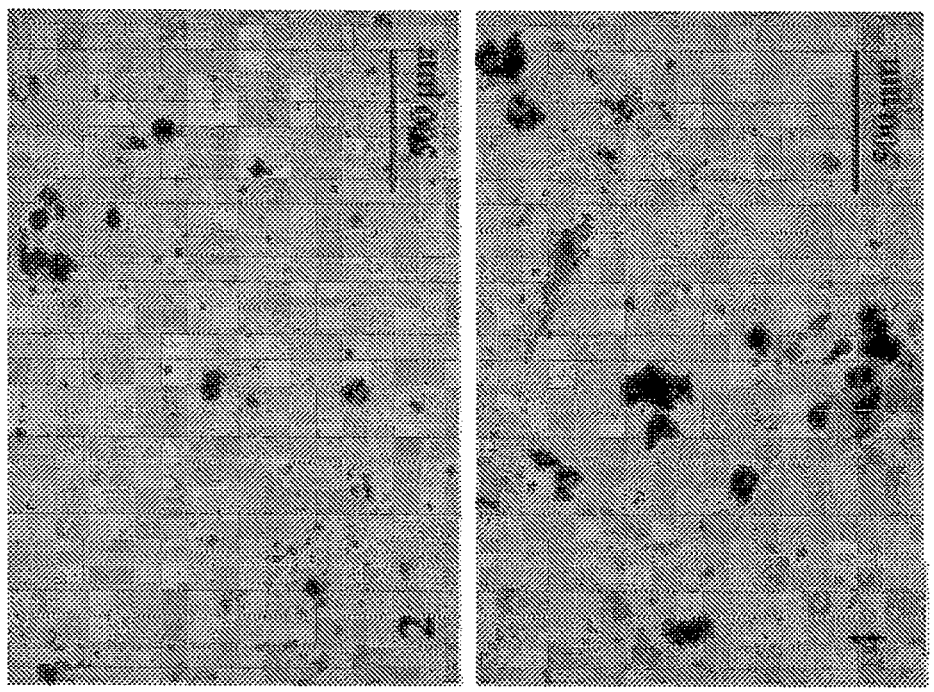
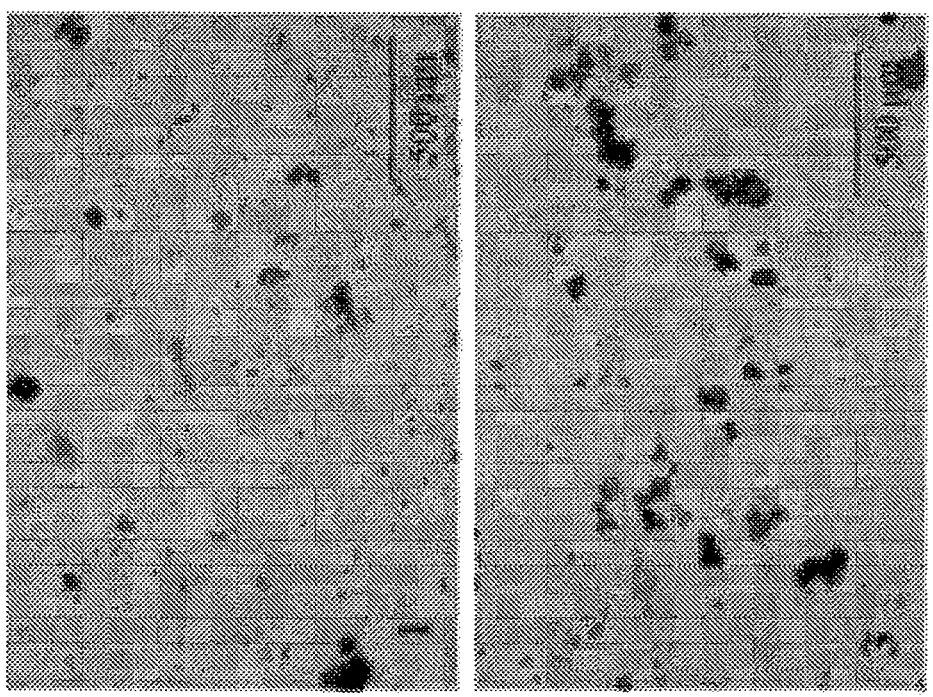
FIGURE 28A

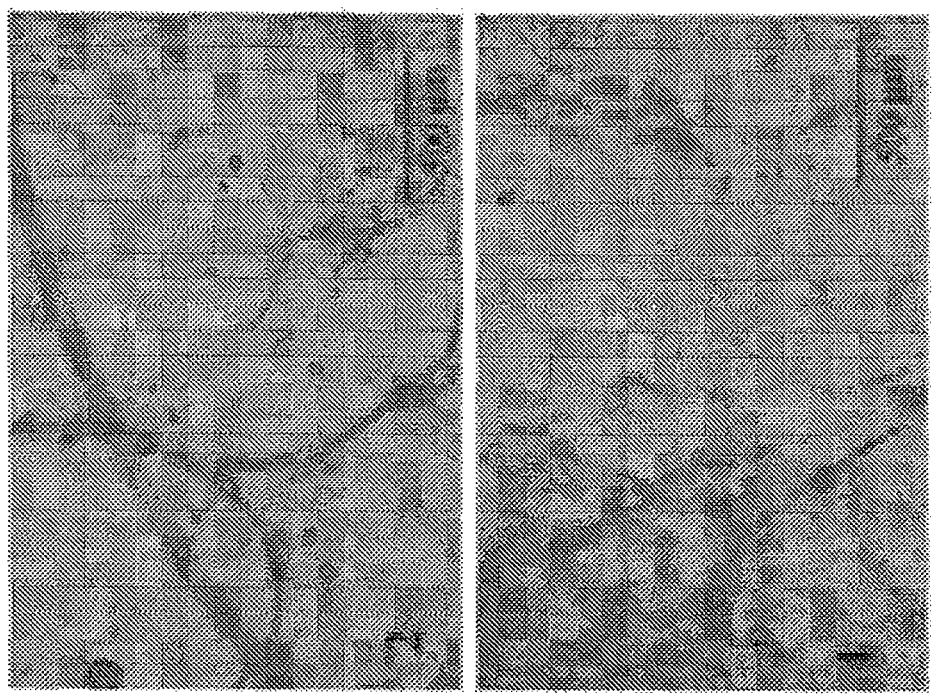
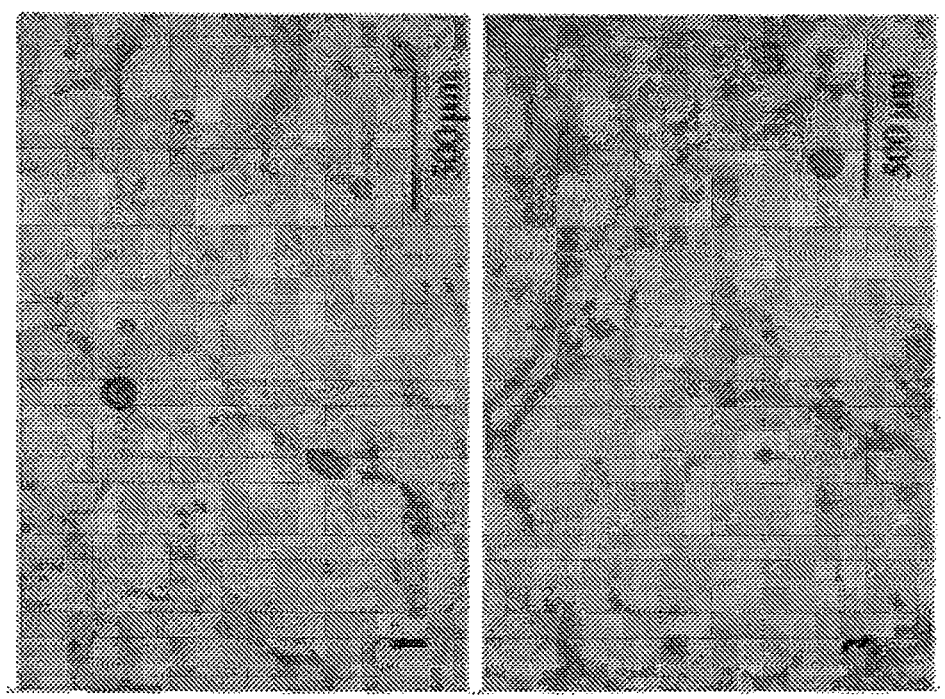
FIGURE 28B

FIGURE 29

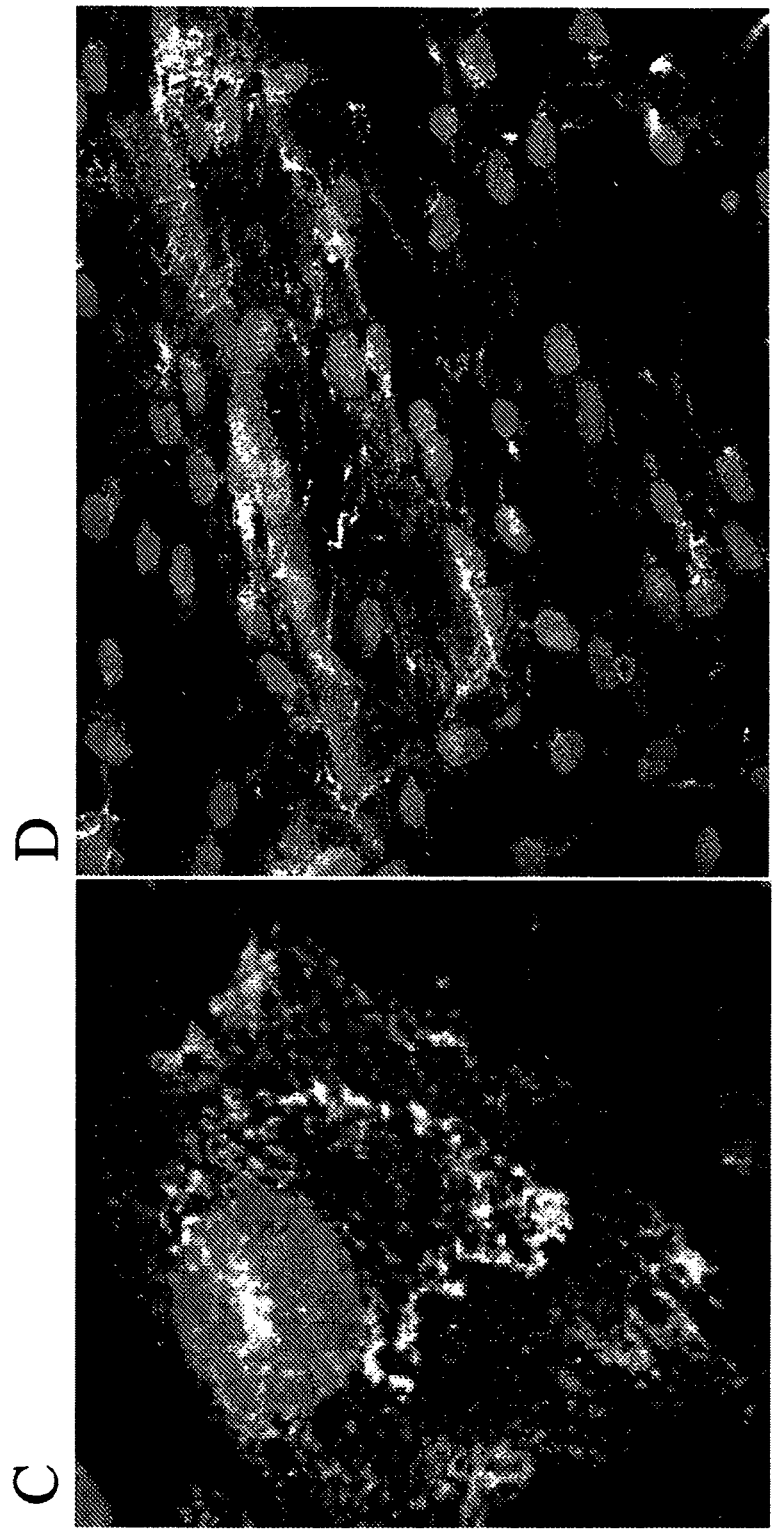
FIGURE 39C-D

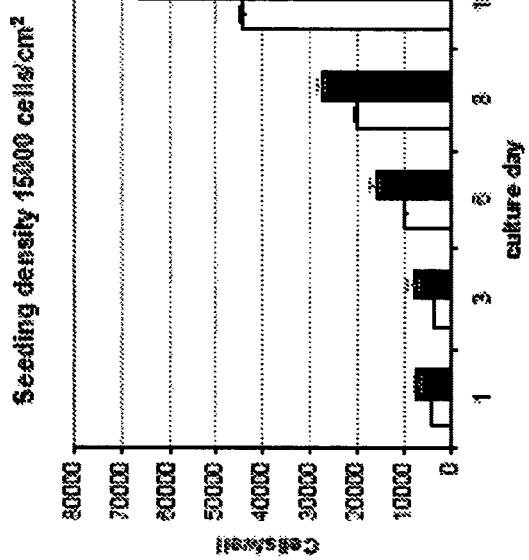
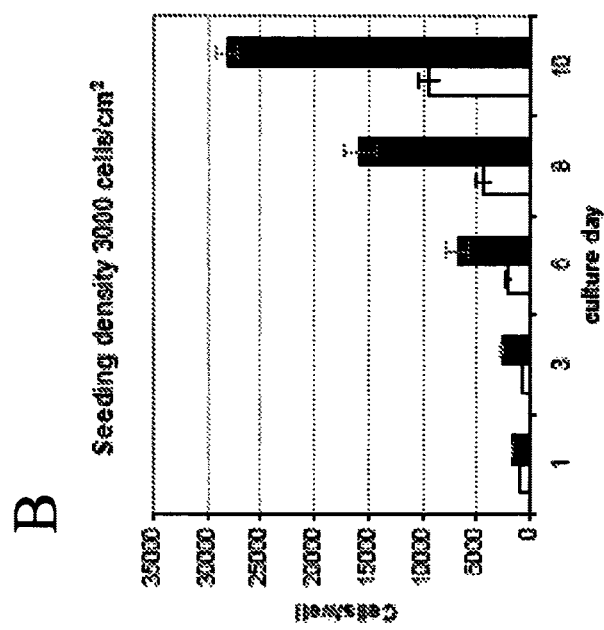
FIGURE 41B-C

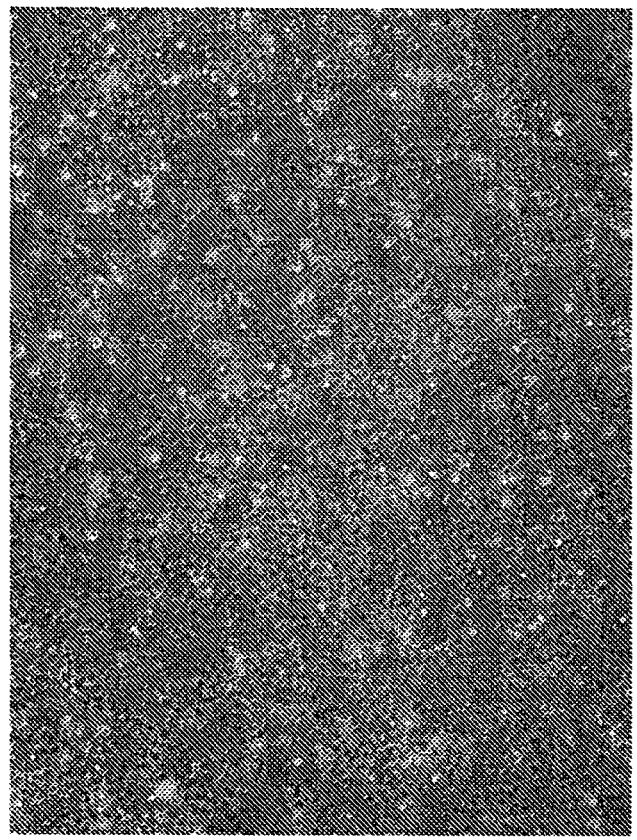
RCM-1 control on Cellstart after 192 h
RGD 16 days post seeding
FIGURE 48

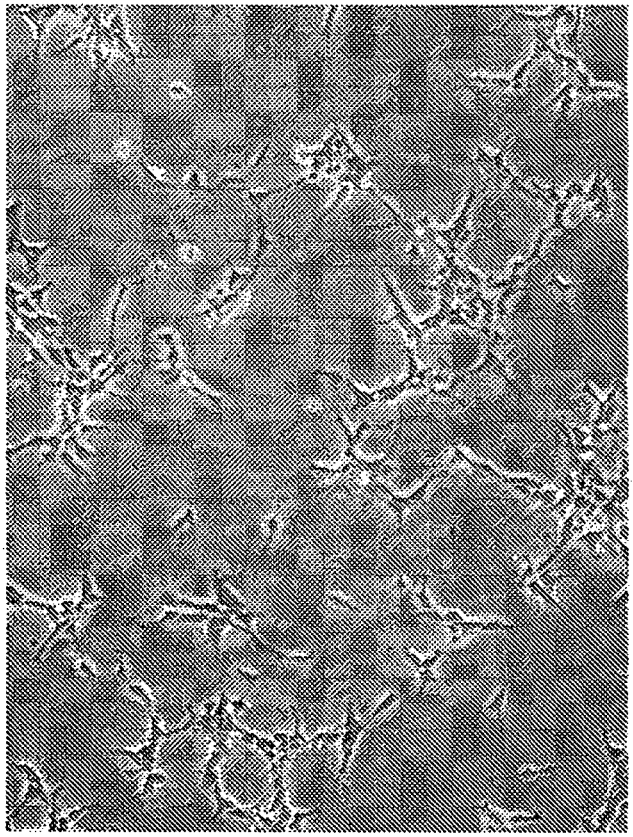
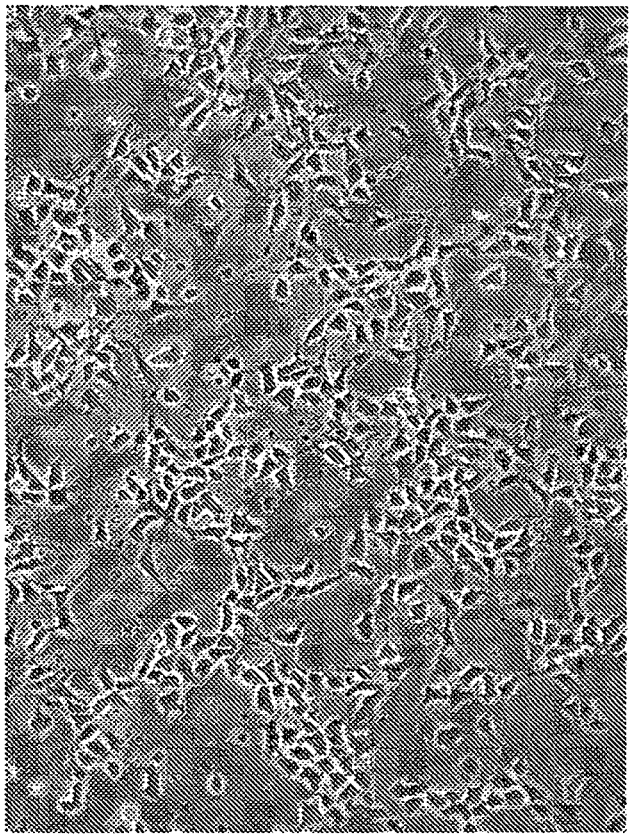
FIGURE 49

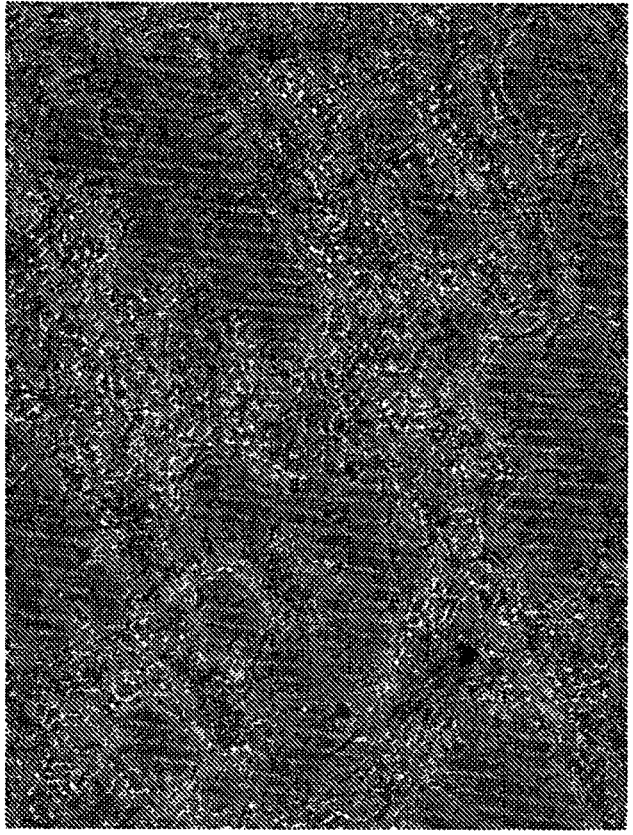
FIGURE 51

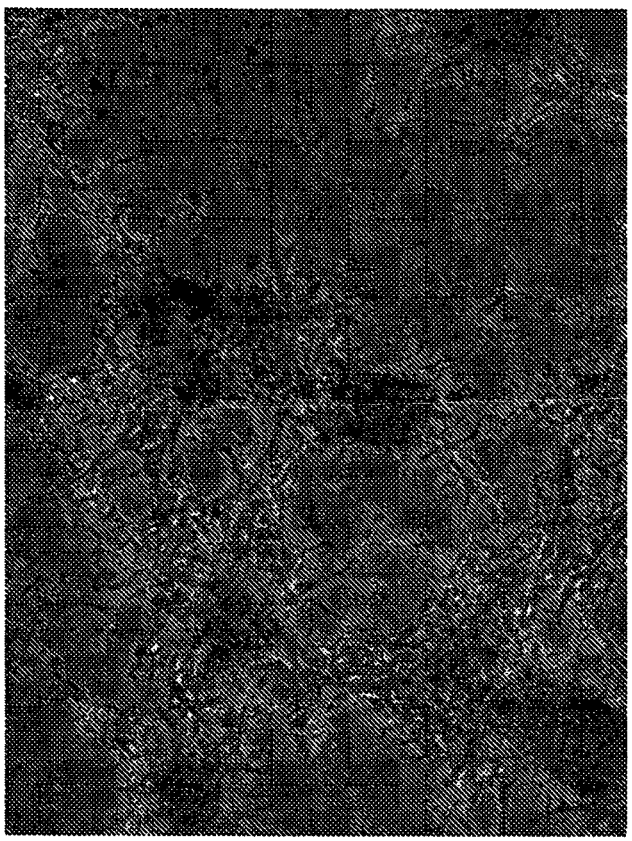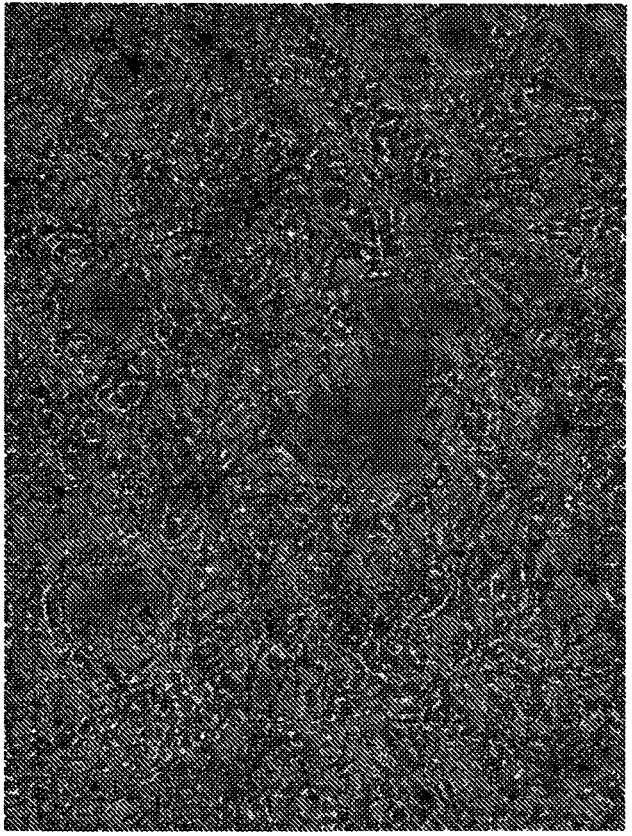
FIGURE 52

SEQUENCE LISTING

```
<160> NUMBER OF SEQ ID NOS: 26

<210> SEQ ID NO 1
<211> LENGTH: 149
<212> TYPE: PRT
<213> ORGANISM: Euprosthenops australis

<400> SEQUENCE: 1

Gly Ser Gly Asn Ser Gly Ile Gln Gly Gln Gly Gly Tyr Gly Gly Leu
1               5                   10                  15
```

```
Gly Gln Gly Gly Tyr Gly Gln Gly Ala Gly Ser Ser Ala Ala Ala
            20                  25                  30

Ala Ala Ala Ala Ala Ala Ala Gly Gly Gln Gly Gly Gln Gly Gln
            35                  40                  45

Gly Gly Tyr Gly Gln Gly Ser Gly Gly Ser Ala Ala Ala Ala Ala
            50                  55                  60

Ala Ala Ala Ala Ala Ala Ala Gly Arg Gly Gln Gly Gly Tyr
65                  70                  75                  80

Gly Gln Gly Ser Gly Gly Asn Ala Ala Ala Ala Ala Ala Ala Ala
            85                  90                  95

Ala Ala Ala Ala Ala Gly Gln Gly Gly Gln Gly Gly Tyr Gly Arg Gln
            100                 105                 110

Ser Gln Gly Ala Gly Ser Ala Ala Ala Ala Ala Ala Ala Ala Ala
            115                 120                 125

Ala Ala Ala Ala Gly Ser Gly Gln Gly Gly Tyr Gly Gln Gly Gln Gly
            130                 135                 140

Gly Tyr Gly Gln Ser
145
```

```
<210> SEQ ID NO 2
<211> LENGTH: 265
<212> TYPE: PRT
<213> ORGANISM: Euprosthenops australis
<220> FEATURE:
<221> NAME/KEY: DOMAIN
<222> LOCATION: (1)..(167)
<223> OTHER INFORMATION: REP fragment
<220> FEATURE:
<221> NAME/KEY: DOMAIN
<222> LOCATION: (168)..(265)
<223> OTHER INFORMATION: CT fragment

<400> SEQUENCE: 2

Gly Ser Gly Asn Ser Gly Ile Gln Gly Gln Gly Gly Tyr Gly Gly Leu
1               5                   10                  15

Gly Gln Gly Gly Tyr Gly Gln Gly Ala Gly Ser Ser Ala Ala Ala
            20                  25                  30

Ala Ala Ala Ala Ala Ala Ala Gly Gly Gln Gly Gly Gln Gly Gln
            35                  40                  45

Gly Gly Tyr Gly Gln Gly Ser Gly Gly Ser Ala Ala Ala Ala Ala
            50                  55                  60

Ala Ala Ala Ala Ala Ala Ala Gly Arg Gly Gln Gly Gly Tyr
65                  70                  75                  80

Gly Gln Gly Ser Gly Gly Asn Ala Ala Ala Ala Ala Ala Ala Ala
            85                  90                  95

Ala Ala Ala Ala Ala Gly Gln Gly Gly Gln Gly Gly Tyr Gly Arg Gln
            100                 105                 110

Ser Gln Gly Ala Gly Ser Ala Ala Ala Ala Ala Ala Ala Ala Ala
            115                 120                 125

Ala Ala Ala Ala Gly Ser Gly Gln Gly Gly Tyr Gly Gln Gly Gln Gly
            130                 135                 140

Gly Tyr Gly Gln Ser Ser Ala Ser Ala Ser Ala Ala Ser Ala Ala
145                 150                 155                 160

Ser Thr Val Ala Asn Ser Val Ser Arg Leu Ser Ser Pro Ser Ala Val
                    165                 170                 175

Ser Arg Val Ser Ser Ala Val Ser Ser Leu Val Ser Asn Gly Gln Val
            180                 185                 190
```

Asn Met Ala Ala Leu Pro Asn Ile Ile Ser Asn Ile Ser Ser Ser Val
            195                 200                 205

Ser Ala Ser Ala Pro Gly Ala Ser Gly Cys Glu Val Ile Val Gln Ala
            210                 215                 220

Leu Leu Glu Val Ile Thr Ala Leu Val Gln Ile Val Ser Ser Ser Ser
225                 230                 235                 240

Val Gly Tyr Ile Asn Pro Ser Ala Val Asn Gln Ile Thr Asn Val Val
            245                 250                 255

Ala Asn Ala Met Ala Gln Val Met Gly
            260                 265

<210> SEQ ID NO 3
<211> LENGTH: 296
<212> TYPE: PRT
<213> ORGANISM: Euprosthenops australis
<220> FEATURE:
<221> NAME/KEY: DOMAIN
<222> LOCATION: (1)..(137)
<223> OTHER INFORMATION: NT fragment
<220> FEATURE:
<221> NAME/KEY: DOMAIN
<222> LOCATION: (138)..(296)
<223> OTHER INFORMATION: REP fragment

<400> SEQUENCE: 3

Gly Ser Gly Asn Ser His Thr Thr Pro Trp Thr Asn Pro Gly Leu Ala
1               5                   10                  15

Glu Asn Phe Met Asn Ser Phe Met Gln Gly Leu Ser Ser Met Pro Gly
            20                  25                  30

Phe Thr Ala Ser Gln Leu Asp Asp Met Ser Thr Ile Ala Gln Ser Met
            35                  40                  45

Val Gln Ser Ile Gln Ser Leu Ala Ala Gln Gly Arg Thr Ser Pro Asn
    50                  55                  60

Lys Leu Gln Ala Leu Asn Met Ala Phe Ala Ser Ser Met Ala Glu Ile
65                  70                  75                  80

Ala Ala Ser Glu Glu Gly Gly Gly Ser Leu Ser Thr Lys Thr Ser Ser
            85                  90                  95

Ile Ala Ser Ala Met Ser Asn Ala Phe Leu Gln Thr Thr Gly Val Val
            100                 105                 110

Asn Gln Pro Phe Ile Asn Glu Ile Thr Gln Leu Val Ser Met Phe Ala
            115                 120                 125

Gln Ala Gly Met Asn Asp Val Ser Ala Ser Ala Ser Ala Gly Ala Ser
            130                 135                 140

Ala Ala Ala Ser Ala Gly Ala Ala Ser Gly Gln Gly Gly Tyr Gly Gly
145                 150                 155                 160

Leu Gly Gln Gly Gly Tyr Gly Gln Gly Ala Gly Ser Ser Ala Ala Ala
            165                 170                 175

Ala Ala Ala Ala Ala Ala Ala Ala Gly Gly Gln Gly Gly Gln Gly Gly
            180                 185                 190

Gln Gly Gly Tyr Gly Gln Gly Ser Gly Gly Ser Ala Ala Ala Ala Ala
            195                 200                 205

Ala Ala Ala Ala Ala Ala Ala Ala Ala Gly Arg Gly Gln Gly Gly Gly
            210                 215                 220

Tyr Gly Gln Gly Ser Gly Gly Asn Ala Ala Ala Ala Ala Ala Ala Ala
225                 230                 235                 240

Ala Ala Ala Ala Ala Ala Gly Gln Gly Gly Gln Gly Gly Tyr Gly
            245                 250                 255

```
Arg Gln Ser Gln Gly Ala Gly Ser Ala Ala Ala Ala Ala Ala
            260                 265                 270
Ala Ala Ala Ala Ala Gly Ser Gly Gln Gly Tyr Gly Gly Gln
        275                 280                 285
Gly Gln Gly Gly Tyr Gly Gln Ser
        290                 295

<210> SEQ ID NO 4
<211> LENGTH: 340
<212> TYPE: PRT
<213> ORGANISM: Euprosthenops australis
<220> FEATURE:
<221> NAME/KEY: DOMAIN
<222> LOCATION: (1)..(137)
<223> OTHER INFORMATION: NT fragment
<220> FEATURE:
<221> NAME/KEY: DOMAIN
<222> LOCATION: (138)..(340)
<223> OTHER INFORMATION: REP fragment

<400> SEQUENCE: 4

Gly Ser Gly Asn Ser His Thr Thr Pro Trp Thr Asn Pro Gly Leu Ala
1               5                   10                  15
Glu Asn Phe Met Asn Ser Phe Met Gln Gly Leu Ser Ser Met Pro Gly
            20                  25                  30
Phe Thr Ala Ser Gln Leu Asp Asp Met Ser Thr Ile Ala Gln Ser Met
        35                  40                  45
Val Gln Ser Ile Gln Ser Leu Ala Ala Gln Gly Arg Thr Ser Pro Asn
    50                  55                  60
Lys Leu Gln Ala Leu Asn Met Ala Phe Ala Ser Ser Met Ala Glu Ile
65                  70                  75                  80
Ala Ala Ser Glu Glu Gly Gly Gly Ser Leu Ser Thr Lys Thr Ser Ser
                85                  90                  95
Ile Ala Ser Ala Met Ser Asn Ala Phe Leu Gln Thr Thr Gly Val Val
            100                 105                 110
Asn Gln Pro Phe Ile Asn Glu Ile Thr Gln Leu Val Ser Met Phe Ala
        115                 120                 125
Gln Ala Gly Met Asn Asp Val Ser Ala Ser Ala Ser Gly Ala Ser
    130                 135                 140
Ala Ala Ala Ser Ala Gly Ala Pro Gly Tyr Ser Pro Ala Pro Ser Tyr
145                 150                 155                 160
Ser Ser Gly Gly Tyr Ala Ser Ser Ala Ala Ser Ala Ala Ala Ala Ala
                165                 170                 175
Gly Gln Gly Gly Pro Gly Gly Tyr Gly Pro Ala Pro Asn Gln Gly Ala
            180                 185                 190
Ser Ser Ala Ala Ala Ala Ala Gly Ser Gly Gln Gly Pro Ser Gly
        195                 200                 205
Pro Tyr Gly Thr Ser Tyr Gln Ile Ser Thr Gln Tyr Thr Gln Thr Thr
    210                 215                 220
Thr Ser Gln Gly Gln Gly Tyr Gly Ser Ser Ser Ala Gly Ala Ala Ala
225                 230                 235                 240
Ala Gly Ala Ala Gly Ala Gly Gln Gly Gly Tyr Gly Gly Gln Gly Gln
                245                 250                 255
Gly Gly Tyr Gly Gln Gly Ala Gly Gly Ala Ala Ala Ala Ala Ala
            260                 265                 270
Ala Ala Ala Ala Ala Ala Ala Gly Gln Gly Gln Gly Gly Gly
        275                 280                 285
```

```
Gly Tyr Gly Gln Gly Gly Gln Gly Gly Gln Gly Gln Gly
        290                 295                 300

Gly Tyr Gly Gln Gly Ala Gly Ser Ser Ala Ala Ala Ala Ala Ala
305                 310                 315                 320

Ala Ala Ala Ala Ala Ala Ala Gly Arg Gly Gln Gly Gly Tyr Gly Pro
                325                 330                 335

Gly Ser Gly Gly
            340

<210> SEQ ID NO 5
<211> LENGTH: 424
<212> TYPE: PRT
<213> ORGANISM: Euprosthenops australis
<220> FEATURE:
<221> NAME/KEY: DOMAIN
<222> LOCATION: (1)..(136)
<223> OTHER INFORMATION: NT fragment
<220> FEATURE:
<221> NAME/KEY: DOMAIN
<222> LOCATION: (137)..(313)
<223> OTHER INFORMATION: REP fragment
<220> FEATURE:
<221> NAME/KEY: DOMAIN
<222> LOCATION: (314)..(411)
<223> OTHER INFORMATION: CT fragment
<220> FEATURE:
<221> NAME/KEY: DOMAIN
<222> LOCATION: (412)..(424)
<223> OTHER INFORMATION: His tag

<400> SEQUENCE: 5

Met Lys Ala Ser His Thr Thr Pro Trp Thr Asn Pro Gly Leu Ala Glu
1               5                   10                  15

Asn Phe Met Asn Ser Phe Met Gln Gly Leu Ser Ser Met Pro Gly Phe
            20                  25                  30

Thr Ala Ser Gln Leu Asp Asp Met Ser Thr Ile Ala Gln Ser Met Val
        35                  40                  45

Gln Ser Ile Gln Ser Leu Ala Ala Gln Gly Arg Thr Ser Pro Asn Lys
    50                  55                  60

Leu Gln Ala Leu Asn Met Ala Phe Ala Ser Ser Met Ala Glu Ile Ala
65                  70                  75                  80

Ala Ser Glu Glu Gly Gly Gly Ser Leu Ser Thr Lys Thr Ser Ser Ile
                85                  90                  95

Ala Ser Ala Met Ser Asn Ala Phe Leu Gln Thr Thr Gly Val Val Asn
            100                 105                 110

Gln Pro Phe Ile Asn Glu Ile Thr Gln Leu Val Ser Met Phe Ala Gln
        115                 120                 125

Ala Gly Met Asn Asp Val Ser Ala Ser Ala Ser Ala Gly Ala Ser Ala
    130                 135                 140

Ala Ala Ser Ala Gly Ala Ala Ser Gly Gln Gly Gly Tyr Gly Gly Leu
145                 150                 155                 160

Gly Gln Gly Gly Tyr Gly Gln Gly Ala Gly Ser Ser Ala Ala Ala Ala
                165                 170                 175

Ala Ala Ala Ala Ala Ala Ala Gly Gly Gln Gly Gly Gln Gly Gln
            180                 185                 190

Gly Gly Tyr Gly Gln Gly Ser Gly Gly Ser Ala Ala Ala Ala Ala
        195                 200                 205

Ala Ala Ala Ala Ala Ala Ala Ala Gly Arg Gly Gln Gly Gly Tyr
    210                 215                 220

Gly Gln Gly Ser Gly Gly Asn Ala Ala Ala Ala Ala Ala Ala Ala Ala
```

```
225                 230                 235                 240
Ala Ala Ala Ala Ala Ala Gly Gln Gly Gly Gln Gly Gly Tyr Gly Arg
                245                 250                 255

Gln Ser Gln Gly Ala Gly Ser Ala Ala Ala Ala Ala Ala Ala Ala Ala
            260                 265                 270

Ala Ala Ala Ala Gly Ser Gly Gln Gly Gly Tyr Gly Gly Gln Gly
        275                 280                 285

Gln Gly Gly Tyr Gly Gln Ser Ser Ala Ser Ala Ser Ala Ala Ala Ser
    290                 295                 300

Ala Ala Ser Thr Val Ala Asn Ser Val Ser Arg Leu Ser Ser Pro Ser
305                 310                 315                 320

Ala Val Ser Arg Val Ser Ser Ala Val Ser Ser Leu Val Ser Asn Gly
                325                 330                 335

Gln Val Asn Met Ala Ala Leu Pro Asn Ile Ile Ser Asn Ile Ser Ser
            340                 345                 350

Ser Val Ser Ala Ser Ala Pro Gly Ala Ser Gly Cys Glu Val Ile Val
        355                 360                 365

Gln Ala Leu Leu Glu Val Ile Thr Ala Leu Val Gln Ile Val Ser Ser
    370                 375                 380

Ser Ser Val Gly Tyr Ile Asn Pro Ser Ala Val Asn Gln Ile Thr Asn
385                 390                 395                 400

Val Val Ala Asn Ala Met Ala Gln Val Met Gly Lys Leu Ala Ala Ala
                405                 410                 415

Leu Glu His His His His His His
            420

<210> SEQ ID NO 6
<211> LENGTH: 137
<212> TYPE: PRT
<213> ORGANISM: Euprosthenops australis
<220> FEATURE:
<221> NAME/KEY: VARIANT
<222> LOCATION: (6)..(6)
<223> OTHER INFORMATION: deletion (deltaHis)

<400> SEQUENCE: 6

Gly Ser Gly Asn Ser His Thr Thr Pro Trp Thr Asn Pro Gly Leu Ala
1               5                   10                  15

Glu Asn Phe Met Asn Ser Phe Met Gln Gly Leu Ser Ser Met Pro Gly
            20                  25                  30

Phe Thr Ala Ser Gln Leu Asp Asp Met Ser Thr Ile Ala Gln Ser Met
        35                  40                  45

Val Gln Ser Ile Gln Ser Leu Ala Ala Gln Gly Arg Thr Ser Pro Asn
    50                  55                  60

Lys Leu Gln Ala Leu Asn Met Ala Phe Ala Ser Ser Met Ala Glu Ile
65                  70                  75                  80

Ala Ala Ser Glu Glu Gly Gly Gly Ser Leu Ser Thr Lys Thr Ser Ser
                85                  90                  95

Ile Ala Ser Ala Met Ser Asn Ala Phe Leu Gln Thr Thr Gly Val Val
            100                 105                 110

Asn Gln Pro Phe Ile Asn Glu Ile Thr Gln Leu Val Ser Met Phe Ala
        115                 120                 125

Gln Ala Gly Met Asn Asp Val Ser Ala
    130                 135

<210> SEQ ID NO 7
```

```
<211> LENGTH: 98
<212> TYPE: PRT
<213> ORGANISM: Euprosthenops australis

<400> SEQUENCE: 7

Ser Arg Leu Ser Ser Pro Ser Ala Val Ser Arg Val Ser Ser Ala Val
1               5                   10                  15

Ser Ser Leu Val Ser Asn Gly Gln Val Asn Met Ala Ala Leu Pro Asn
            20                  25                  30

Ile Ile Ser Asn Ile Ser Ser Ser Val Ser Ala Ser Ala Pro Gly Ala
                35                  40                  45

Ser Gly Cys Glu Val Ile Val Gln Ala Leu Leu Glu Val Ile Thr Ala
50                  55                  60

Leu Val Gln Ile Val Ser Ser Ser Val Gly Tyr Ile Asn Pro Ser
65                  70                  75                  80

Ala Val Asn Gln Ile Thr Asn Val Val Ala Asn Ala Met Ala Gln Val
                85                  90                  95

Met Gly

<210> SEQ ID NO 8
<211> LENGTH: 131
<212> TYPE: PRT
<213> ORGANISM: Artificial Sequence
<220> FEATURE:
<223> OTHER INFORMATION: Consensus sequence derived from spidroin NT
      fragments
<220> FEATURE:
<221> NAME/KEY: VARIANT
<222> LOCATION: (20)..(20)
<223> OTHER INFORMATION: Leu
<220> FEATURE:
<221> NAME/KEY: VARIANT
<222> LOCATION: (42)..(42)
<223> OTHER INFORMATION: Asn
<220> FEATURE:
<221> NAME/KEY: VARIANT
<222> LOCATION: (42)..(42)
<223> OTHER INFORMATION: Gln
<220> FEATURE:
<221> NAME/KEY: VARIANT
<222> LOCATION: (50)..(50)
<223> OTHER INFORMATION: Ser
<220> FEATURE:
<221> NAME/KEY: VARIANT
<222> LOCATION: (50)..(50)
<223> OTHER INFORMATION: Lys
<220> FEATURE:
<221> NAME/KEY: VARIANT
<222> LOCATION: (56)..(56)
<223> OTHER INFORMATION: Arg
<220> FEATURE:
<221> NAME/KEY: VARIANT
<222> LOCATION: (84)..(84)
<223> OTHER INFORMATION: Leu
<220> FEATURE:
<221> NAME/KEY: VARIANT
<222> LOCATION: (114)..(114)
<223> OTHER INFORMATION: Ser
<220> FEATURE:
<221> NAME/KEY: VARIANT
<222> LOCATION: (121)..(121)
<223> OTHER INFORMATION: Asn
<220> FEATURE:
<221> NAME/KEY: VARIANT
<222> LOCATION: (123)..(123)
<223> OTHER INFORMATION: Leu
<220> FEATURE:
<221> NAME/KEY: VARIANT
<222> LOCATION: (124)..(124)
<223> OTHER INFORMATION: Ser
```

-continued

<400> SEQUENCE: 8

```
Gln Ala Asn Thr Pro Trp Ser Ser Pro Asn Leu Ala Asp Ala Phe Ile
1               5                   10                  15

Asn Ser Phe Met Ser Ala Ala Ser Ser Gly Ala Phe Ser Ala Asp
            20                  25                  30

Gln Leu Asp Asp Met Ser Thr Ile Gly Asp Thr Leu Met Ser Ala Met
        35                  40                  45

Asp Asn Met Gly Arg Ser Gly Lys Ser Thr Lys Ser Lys Leu Gln Ala
    50                  55                  60

Leu Asn Met Ala Phe Ala Ser Ser Met Ala Glu Ile Ala Ala Ala Glu
65                  70                  75                  80

Ser Gly Gly Gly Ser Val Gly Val Lys Thr Asn Ala Ile Ser Asp Ala
                85                  90                  95

Leu Ser Ser Ala Phe Tyr Gln Thr Thr Gly Ser Val Asn Pro Gln Phe
            100                 105                 110

Val Asn Glu Ile Arg Ser Leu Ile Gly Met Phe Ala Gln Ala Ser Ala
            115                 120                 125

Asn Glu Val
        130
```

<210> SEQ ID NO 9
<211> LENGTH: 100
<212> TYPE: PRT
<213> ORGANISM: Artificial Sequence
<220> FEATURE:
<223> OTHER INFORMATION: Consensus sequence derived from known MaSp1 and
      MaSp2 proteins
<220> FEATURE:
<221> NAME/KEY: MISC_FEATURE
<222> LOCATION: (1)..(71)
<223> OTHER INFORMATION: Sequence length present in known species
      variants
<220> FEATURE:
<221> NAME/KEY: VARIANT
<222> LOCATION: (7)..(7)
<223> OTHER INFORMATION: Glu

<400> SEQUENCE: 9

```
Ser Arg Leu Ser Ser Pro Gln Ala Ser Ser Arg Val Ser Ala Val
1               5                   10                  15

Ser Asn Leu Val Ser Ser Gly Pro Thr Asn Ser Ala Ala Leu Ser Asn
            20                  25                  30

Thr Ile Ser Asn Val Val Ser Gln Ile Ser Ala Ser Asn Pro Gly Leu
        35                  40                  45

Ser Gly Cys Asp Val Leu Val Gln Ala Leu Leu Glu Val Val Ser Ala
    50                  55                  60

Leu Val His Ile Leu Gly Ser Ser Ile Gly Gln Val Asn Tyr Gly
65                  70                  75                  80

Ser Ala Gly Gln Ala Thr Gln Ile Val Gly Gln Ser Val Ala Gln Ala
                85                  90                  95

Leu Gly Glu Phe
        100
```

<210> SEQ ID NO 10
<211> LENGTH: 1110
<212> TYPE: PRT
<213> ORGANISM: Euprosthenops australis
<220> FEATURE:
<221> NAME/KEY: REPEAT
<222> LOCATION: (7)..(19)
<220> FEATURE:

-continued

```
<221> NAME/KEY: REPEAT
<222> LOCATION: (20)..(42)
<220> FEATURE:
<221> NAME/KEY: REPEAT
<222> LOCATION: (43)..(56)
<220> FEATURE:
<221> NAME/KEY: REPEAT
<222> LOCATION: (57)..(70)
<220> FEATURE:
<221> NAME/KEY: REPEAT
<222> LOCATION: (71)..(83)
<220> FEATURE:
<221> NAME/KEY: REPEAT
<222> LOCATION: (84)..(106)
<220> FEATURE:
<221> NAME/KEY: REPEAT
<222> LOCATION: (107)..(120)
<220> FEATURE:
<221> NAME/KEY: REPEAT
<222> LOCATION: (121)..(134)
<220> FEATURE:
<221> NAME/KEY: REPEAT
<222> LOCATION: (135)..(147)
<220> FEATURE:
<221> NAME/KEY: REPEAT
<222> LOCATION: (148)..(170)
<220> FEATURE:
<221> NAME/KEY: REPEAT
<222> LOCATION: (171)..(183)
<220> FEATURE:
<221> NAME/KEY: REPEAT
<222> LOCATION: (184)..(197)
<220> FEATURE:
<221> NAME/KEY: REPEAT
<222> LOCATION: (198)..(211)
<220> FEATURE:
<221> NAME/KEY: REPEAT
<222> LOCATION: (212)..(234)
<220> FEATURE:
<221> NAME/KEY: REPEAT
<222> LOCATION: (235)..(248)
<220> FEATURE:
<221> NAME/KEY: REPEAT
<222> LOCATION: (249)..(265)
<220> FEATURE:
<221> NAME/KEY: REPEAT
<222> LOCATION: (266)..(279)
<220> FEATURE:
<221> NAME/KEY: REPEAT
<222> LOCATION: (280)..(293)
<220> FEATURE:
<221> NAME/KEY: REPEAT
<222> LOCATION: (294)..(306)
<220> FEATURE:
<221> NAME/KEY: REPEAT
<222> LOCATION: (307)..(329)
<220> FEATURE:
<221> NAME/KEY: REPEAT
<222> LOCATION: (330)..(342)
<220> FEATURE:
<221> NAME/KEY: REPEAT
<222> LOCATION: (343)..(356)
<220> FEATURE:
<221> NAME/KEY: REPEAT
<222> LOCATION: (357)..(370)
<220> FEATURE:
<221> NAME/KEY: REPEAT
<222> LOCATION: (371)..(393)
<220> FEATURE:
<221> NAME/KEY: REPEAT
<222> LOCATION: (394)..(406)
<220> FEATURE:
<221> NAME/KEY: REPEAT
<222> LOCATION: (407)..(420)
<220> FEATURE:
<221> NAME/KEY: REPEAT
<222> LOCATION: (421)..(434)
<220> FEATURE:
<221> NAME/KEY: REPEAT
```

```
<222> LOCATION: (435)..(457)
<220> FEATURE:
<221> NAME/KEY: REPEAT
<222> LOCATION: (458)..(470)
<220> FEATURE:
<221> NAME/KEY: REPEAT
<222> LOCATION: (471)..(488)
<220> FEATURE:
<221> NAME/KEY: REPEAT
<222> LOCATION: (489)..(502)
<220> FEATURE:
<221> NAME/KEY: REPEAT
<222> LOCATION: (503)..(516)
<220> FEATURE:
<221> NAME/KEY: REPEAT
<222> LOCATION: (517)..(529)
<220> FEATURE:
<221> NAME/KEY: REPEAT
<222> LOCATION: (530)..(552)
<220> FEATURE:
<221> NAME/KEY: REPEAT
<222> LOCATION: (553)..(566)
<220> FEATURE:
<221> NAME/KEY: REPEAT
<222> LOCATION: (567)..(580)
<220> FEATURE:
<221> NAME/KEY: REPEAT
<222> LOCATION: (581)..(594)
<220> FEATURE:
<221> NAME/KEY: REPEAT
<222> LOCATION: (595)..(617)
<220> FEATURE:
<221> NAME/KEY: REPEAT
<222> LOCATION: (618)..(630)
<220> FEATURE:
<221> NAME/KEY: REPEAT
<222> LOCATION: (631)..(647)
<220> FEATURE:
<221> NAME/KEY: REPEAT
<222> LOCATION: (648)..(661)
<220> FEATURE:
<221> NAME/KEY: REPEAT
<222> LOCATION: (662)..(675)
<220> FEATURE:
<221> NAME/KEY: REPEAT
<222> LOCATION: (676)..(688)
<220> FEATURE:
<221> NAME/KEY: REPEAT
<222> LOCATION: (689)..(711)
<220> FEATURE:
<221> NAME/KEY: REPEAT
<222> LOCATION: (712)..(725)
<220> FEATURE:
<221> NAME/KEY: REPEAT
<222> LOCATION: (726)..(739)
<220> FEATURE:
<221> NAME/KEY: REPEAT
<222> LOCATION: (740)..(752)
<220> FEATURE:
<221> NAME/KEY: REPEAT
<222> LOCATION: (753)..(775)
<220> FEATURE:
<221> NAME/KEY: REPEAT
<222> LOCATION: (776)..(789)
<220> FEATURE:
<221> NAME/KEY: REPEAT
<222> LOCATION: (790)..(803)
<220> FEATURE:
<221> NAME/KEY: REPEAT
<222> LOCATION: (804)..(816)
<220> FEATURE:
<221> NAME/KEY: REPEAT
<222> LOCATION: (817)..(839)
<220> FEATURE:
<221> NAME/KEY: REPEAT
<222> LOCATION: (840)..(853)
<220> FEATURE:
<221> NAME/KEY: REPEAT
<222> LOCATION: (854)..(867)
```

```
<220> FEATURE:
<221> NAME/KEY: REPEAT
<222> LOCATION: (868)..(880)
<220> FEATURE:
<221> NAME/KEY: REPEAT
<222> LOCATION: (881)..(903)
<220> FEATURE:
<221> NAME/KEY: REPEAT
<222> LOCATION: (904)..(917)
<220> FEATURE:
<221> NAME/KEY: REPEAT
<222> LOCATION: (918)..(931)
<220> FEATURE:
<221> NAME/KEY: REPEAT
<222> LOCATION: (932)..(945)
<220> FEATURE:
<221> NAME/KEY: REPEAT
<222> LOCATION: (946)..(968)
<220> FEATURE:
<221> NAME/KEY: REPEAT
<222> LOCATION: (969)..(981)
<220> FEATURE:
<221> NAME/KEY: REPEAT
<222> LOCATION: (982)..(998)
<220> FEATURE:
<221> NAME/KEY: REPEAT
<222> LOCATION: (999)..(1013)
<220> FEATURE:
<221> NAME/KEY: REPEAT
<222> LOCATION: (1014)..(1027)
<220> FEATURE:
<221> NAME/KEY: REPEAT
<222> LOCATION: (1028)..(1042)
<220> FEATURE:
<221> NAME/KEY: REPEAT
<222> LOCATION: (1043)..(1059)
<220> FEATURE:
<221> NAME/KEY: REPEAT
<222> LOCATION: (1060)..(1073)
<220> FEATURE:
<221> NAME/KEY: REPEAT
<222> LOCATION: (1074)..(1092)

<400> SEQUENCE: 10

Gln Gly Ala Gly Gly Asn Ala Ala Ala Ala Ala Ala Ala Ala Ala
1               5                   10                  15

Ala Ala Ala Gly Gln Gly Gly Gln Gly Gly Tyr Gly Gly Leu Gly Gln
            20                  25                  30

Gly Gly Tyr Gly Gln Gly Ala Gly Ser Ser Ala Ala Ala Ala Ala
        35                  40                  45

Ala Ala Ala Ala Ala Ala Ala Gly Arg Gly Gln Gly Gly Tyr Gly
    50                  55                  60

Gln Gly Ser Gly Gly Asn Ala Ala Ala Ala Ala Ala Ala Ala
65                  70                  75                  80

Ala Ala Ser Gly Gln Gly Gly Gln Gly Gly Gln Gly Gly Gln Gly Gln
                85                  90                  95

Gly Gly Tyr Gly Gln Gly Ala Gly Ser Ser Ala Ala Ala Ala Ala
        100                 105                 110

Ala Ala Ala Ala Ala Ala Ala Gly Gln Gly Gln Gly Arg Tyr Gly
    115                 120                 125

Gln Gly Ala Gly Gly Asn Ala Ala Ala Ala Ala Ala Ala Ala
    130                 135                 140

Ala Ala Ala Gly Gln Gly Gly Gln Gly Gly Gly Gly Leu Gly Gln
145                 150                 155                 160

Gly Gly Tyr Gly Gln Gly Ala Gly Ser Ser Ala Ala Ala Ala Ala
        165                 170                 175

Ser Ala Ala Ala Ala Ala Ala Gly Arg Gly Gln Gly Gly Tyr Gly Gln
```

```
            180             185             190
Gly Ala Gly Gly Asn Ala Ala Ala Ala Ala Ala Ala Ala
        195             200             205
Ala Ala Ala Gly Gln Gly Gly Gln Gly Gly Tyr Gly Gln
    210             215             220
Gly Gly Tyr Gly Gln Gly Ala Gly Ser Ser Ala Ala Ala
225             230             235             240
Ala Ala Ala Ala Ala Ala Gly Gly Gln Gly Gly Gln Gly
            245             250             255
Arg Tyr Gly Gln Gly Ala Gly Ser Ser Ala Ala Ala Ala
            260             265             270
Ala Ala Ala Ala Ala Ala Gly Gln Gly Gln Gly Tyr Gly Gln
        275             280             285
Gly Ala Gly Gly Asn Ala Ala Ala Ala Ala Ala Ala Ala
    290             295             300
Ala Ala Gly Gln Gly Gly Gln Gly Gly Gln Gly Leu Gly Gln Gly
305             310             315             320
Gly Tyr Gly Gln Gly Ala Gly Ser Ser Ala Ala Ala Ala
            325             330             335
Ala Ala Ala Ala Ala Gly Arg Gly Gln Gly Tyr Gly Gln Gly
            340             345             350
Ala Gly Gly Asn Ala Ala Ala Ala Ala Ala Glu Ala Ala
        355             360             365
Ala Ala Gly Gln Gly Gly Gln Gly Gly Tyr Gly Gly Leu Gly Gln Gly
    370             375             380
Gly Tyr Gly Gln Gly Ala Gly Ser Ser Ala Ala Ala Ala
385             390             395             400
Ala Ala Ala Ala Ala Ala Gly Arg Gly Gln Gly Tyr Gly Gln Gly
            405             410             415
Ala Gly Gly Asn Ala Ala Ala Ala Ala Ala Ala Ala Ala
        420             425             430
Ala Ala Gly Gln Gly Gly Gln Gly Gly Tyr Gly Gly Leu Gly Gln Gly
            435             440             445
Gly Tyr Gly Gln Gly Ala Gly Ser Ser Ala Ala Ala Ala
    450             455             460
Ala Ala Ala Ala Ala Ala Gly Gly Gln Gly Gly Gln Gly Gln Gly Arg
465             470             475             480
Tyr Gly Gln Gly Ala Gly Ser Ser Ala Ala Ala Ala Ala
            485             490             495
Ala Ala Ala Ala Ala Ala Gly Arg Gly Gln Gly Tyr Gly Gln Gly
        500             505             510
Ser Gly Gly Asn Ala Ala Ala Ala Ala Ala Ala Ala Ala
        515             520             525
Ser Gly Gln Gly Ser Gln Gly Gly Gln Gly Gln Gly Gly
    530             535             540
Tyr Gly Gln Gly Ala Gly Ser Ser Ala Ala Ala Ala Ala
545             550             555             560
Ala Ala Ala Ala Ala Ser Gly Arg Gly Gln Gly Tyr Gly Gln Gly
            565             570             575
Ala Gly Gly Asn Ala Ala Ala Ala Ala Ala Ala Ala Ala
        580             585             590
Ala Ala Gly Gln Gly Gly Gln Gly Gly Tyr Gly Gly Leu Gly Gln Gly
            595             600             605
```

Gly Tyr Gly Gln Gly Ala Gly Ser Ser Ala Ala Ala Ala Ala Ala
            610             615                 620

Ala Ala Ala Ala Ala Gly Gln Gly Gly Gln Gly Gln Gly Gly Tyr
625                 630                 635                 640

Gly Gln Gly Ala Gly Ser Ser Ala Ala Ala Ala Ala Ala Ala Ala
                645                 650                 655

Ala Ala Ala Ala Ala Gly Arg Gly Gln Gly Gly Tyr Gly Gln Gly Ser
            660                 665                 670

Gly Gly Asn Ala Ala Ala Ala Ala Ala Ala Ala Ala Ala Ala Ser
        675                 680                 685

Gly Gln Gly Gly Gln Gly Gln Gly Gly Gln Gly Gln Gly Gly Tyr
    690                 695                 700

Gly Gln Gly Ala Gly Ser Ser Ala Ala Ala Ala Ala Ala Ala Ala
705                 710                 715                 720

Ala Ala Ala Ala Ala Gly Gln Gly Gln Gly Gly Tyr Gly Gln Gly Ala
            725                 730                 735

Gly Gly Asn Ala Ala Ala Ala Ala Ala Ala Ala Ala Ala Ala Ala
        740                 745                 750

Gly Gln Gly Gly Gln Gly Gly Gln Gly Gly Leu Gly Gln Gly Gly Tyr
    755                 760                 765

Gly Gln Gly Ala Gly Ser Ser Ala Ala Ala Ala Ala Ala Ala Ala
    770                 775                 780

Ala Ala Ala Ala Ala Gly Arg Gly Gln Gly Gly Tyr Gly Gln Gly Val
785                 790                 795                 800

Gly Gly Asn Ala Ala Ala Ala Ala Ala Ala Ala Ala Ala Ala Ala
        805                 810                 815

Gly Gln Gly Gly Gln Gly Gly Gln Gly Gly Leu Gly Gln Gly Gly Tyr
    820                 825                 830

Gly Gln Gly Ala Gly Ser Ser Ala Ala Ala Ala Ala Ala Ala Ala
    835                 840                 845

Ala Ala Ala Ala Ala Gly Arg Gly Gln Gly Gly Tyr Gly Gln Gly Ser
850                 855                 860

Gly Gly Asn Ala Ala Ala Ala Ala Ala Ala Ala Ala Ala Ala Ser
865                 870                 875                 880

Gly Gln Gly Ser Gln Gly Gly Gln Gly Gly Gln Gly Gln Gly Gly Tyr
            885                 890                 895

Gly Gln Gly Ala Gly Ser Ser Ala Ala Ala Ala Ala Ala Ala Ala
        900                 905                 910

Ala Ala Ala Ala Ser Gly Arg Gly Gln Gly Gly Tyr Gly Gln Gly Ala
            915                 920                 925

Gly Gly Asn Ala Ala Ala Ala Ala Ala Ala Ala Ala Ala Ala Ala
        930                 935                 940

Ala Gly Gln Gly Gly Gln Gly Gly Tyr Gly Gly Leu Gly Gln Gly Gly
945                 950                 955                 960

Tyr Gly Gln Gly Ala Gly Ser Ser Ala Ala Ala Ala Ala Ala Ala
            965                 970                 975

Ala Ala Ala Ala Gly Gly Gln Gly Gly Gln Gly Gln Gly Gly Tyr Gly
            980                 985                 990

Gln Gly Ser Gly Gly Ser Ala Ala Ala Ala Ala Ala Ala Ala Ala
    995                 1000                1005

Ala Ala Ala Ala Ala Gly Arg Gly Gln Gly Gly Tyr Gly Gln Gly
    1010                1015                1020

```
Ser Gly Gly Asn Ala Ala Ala Ala Ala Ala Ala Ala Ala
    1025                1030                1035

Ala Ala Ala Ala Gly Gln Gly Gly Gln Gly Gly Tyr Gly Arg Gln
    1040                1045                1050

Ser Gln Gly Ala Gly Ser Ala Ala Ala Ala Ala Ala Ala Ala
    1055                1060                1065

Ala Ala Ala Ala Ala Gly Ser Gly Gln Gly Gly Tyr Gly Gly Gln
    1070                1075                1080

Gly Gln Gly Gly Tyr Gly Gln Ser Ser Ala Ser Ala Ser Ala Ala
    1085                1090                1095

Ala Ser Ala Ala Ser Thr Val Ala Asn Ser Val Ser
    1100                1105                1110

<210> SEQ ID NO 11
<211> LENGTH: 23
<212> TYPE: PRT
<213> ORGANISM: Artificial Sequence
<220> FEATURE:
<223> OTHER INFORMATION: Consensus sequence derived from internal
      repeats of Euprosthenops australis MaSp1
<220> FEATURE:
<221> NAME/KEY: VARIANT
<222> LOCATION: (4)..(4)
<223> OTHER INFORMATION: Ser
<220> FEATURE:
<221> NAME/KEY: VARIANT
<222> LOCATION: (8)..(8)
<223> OTHER INFORMATION: Tyr
<220> FEATURE:
<221> NAME/KEY: VARIANT
<222> LOCATION: (11)..(11)
<223> OTHER INFORMATION: Gln

<400> SEQUENCE: 11

Gly Gln Gly Gly Gln Gly Gly Gln Gly Gly Leu Gly Gln Gly Gly Tyr
1               5                   10                  15

Gly Gln Gly Ala Gly Ser Ser
            20

<210> SEQ ID NO 12
<211> LENGTH: 17
<212> TYPE: PRT
<213> ORGANISM: Artificial Sequence
<220> FEATURE:
<223> OTHER INFORMATION: Consensus sequence derived from internal
      repeats of Euprosthenops australis MaSp1
<220> FEATURE:
<221> NAME/KEY: VARIANT
<222> LOCATION: (9)..(9)
<223> OTHER INFORMATION: Arg
<220> FEATURE:
<221> NAME/KEY: VARIANT
<222> LOCATION: (14)..(14)
<223> OTHER INFORMATION: Ser
<220> FEATURE:
<221> NAME/KEY: VARIANT
<222> LOCATION: (16)..(16)
<223> OTHER INFORMATION: Gly

<400> SEQUENCE: 12

Gly Gln Gly Gly Gln Gly Gln Gly Gly Tyr Gly Gln Gly Ala Gly Ser
1               5                   10                  15

Ser

<210> SEQ ID NO 13
<211> LENGTH: 14
<212> TYPE: PRT
```

```
<213> ORGANISM: Artificial Sequence
<220> FEATURE:
<223> OTHER INFORMATION: Consensus sequence derived from internal
      repeats of Euprosthenops australis MaSp1
<220> FEATURE:
<221> NAME/KEY: VARIANT
<222> LOCATION: (2)..(2)
<223> OTHER INFORMATION: Gln
<220> FEATURE:
<221> NAME/KEY: VARIANT
<222> LOCATION: (6)..(6)
<223> OTHER INFORMATION: Arg
<220> FEATURE:
<221> NAME/KEY: VARIANT
<222> LOCATION: (11)..(11)
<223> OTHER INFORMATION: Ser
<220> FEATURE:
<221> NAME/KEY: VARIANT
<222> LOCATION: (11)..(11)
<223> OTHER INFORMATION: Val

<400> SEQUENCE: 13

Gly Arg Gly Gln Gly Gly Tyr Gly Gln Gly Ala Gly Gly Asn
 1               5                  10

<210> SEQ ID NO 14
<211> LENGTH: 287
<212> TYPE: PRT
<213> ORGANISM: Euprosthenops australis

<400> SEQUENCE: 14

Asn Ser Gly Tyr Gly Gln Gly Ala Gly Gly Asn Ala Ala Ala Ala
 1               5                  10                  15

Ala Ala Ala Ala Ala Ala Ala Ala Gly Gln Gly Gly Gln Gly Gly
                20                  25                  30

Tyr Gly Gly Leu Gly Gln Gly Gly Tyr Gly Gln Gly Ala Gly Ser Ser
            35                  40                  45

Ala Ala Ala Ala Ala Ala Ala Ala Ala Ala Ala Gly Gly Gln Gly
         50                  55                  60

Gly Gln Gly Gly Gln Gly Gly Tyr Gly Gln Gly Ser Gly Gly Ser Ala Ala
 65                  70                  75                  80

Ala Ala Ala Ala Ala Ala Ala Ala Ala Ala Ala Ala Gly Arg Gly
                 85                  90                  95

Gln Gly Gly Tyr Gly Gln Gly Ser Gly Gly Asn Ala Ala Ala Ala
                100                 105                 110

Ala Ala Ala Ala Ala Ala Ala Ala Gly Gln Gly Gly Gln Gly
            115                 120                 125

Gly Tyr Gly Arg Gln Ser Gln Gly Ala Gly Ser Ala Ala Ala Ala
            130                 135                 140

Ala Ala Ala Ala Ala Ala Ala Gly Ser Gly Gln Gly Gly Tyr
145                 150                 155                 160

Gly Gly Gln Gly Gln Gly Gly Tyr Gly Gln Ser Ser Ala Ser Ala Ser
                165                 170                 175

Ala Ala Ala Ser Ala Ala Ser Thr Val Ala Asn Ser Val Ser Arg Leu
            180                 185                 190

Ser Ser Pro Ser Ala Val Ser Arg Val Ser Ser Ala Val Ser Ser Leu
            195                 200                 205

Val Ser Asn Gly Gln Val Asn Met Ala Ala Leu Pro Asn Ile Ile Ser
            210                 215                 220

Asn Ile Ser Ser Ser Val Ser Ala Ser Ala Pro Gly Ala Ser Gly Cys
225                 230                 235                 240
```

Glu Val Ile Val Gln Ala Leu Leu Glu Val Ile Thr Ala Leu Val Gln
                    245                 250                 255

Ile Val Ser Ser Ser Val Gly Tyr Ile Asn Pro Ser Ala Val Asn
        260                 265                 270

Gln Ile Thr Asn Val Val Ala Asn Ala Met Ala Gln Val Met Gly
            275                 280                 285

<210> SEQ ID NO 15
<211> LENGTH: 382
<212> TYPE: PRT
<213> ORGANISM: Euprosthenops australis

<400> SEQUENCE: 15

Gly Ser Gly Asn Ser Gly Tyr Gly Gln Gly Ala Gly Ser Ser Ala Ala
1               5                   10                  15

Ala Ala Ala Ala Ala Ala Ala Ala Ala Ala Ala Gly Arg Gly Gln
            20                  25                  30

Gly Gly Tyr Gly Gln Gly Ser Gly Gly Asn Ala Ala Ala Ala Ala
        35                  40                  45

Ala Ala Ala Ala Ala Ser Gly Gln Gly Ser Gln Gly Gly Gln Gly
    50                  55                  60

Gly Gln Gly Gln Gly Gly Tyr Gly Gln Gly Ala Gly Ser Ser Ala Ala
65                  70                  75                  80

Ala Ala Ala Ala Ala Ala Ala Ala Ala Ser Gly Arg Gly Gln
            85                  90                  95

Gly Gly Tyr Gly Gln Gly Ala Gly Gly Asn Ala Ala Ala Ala Ala
        100                 105                 110

Ala Ala Ala Ala Ala Ala Ala Gly Gln Gly Gly Gln Gly Gly Tyr
    115                 120                 125

Gly Gly Leu Gly Gln Gly Gly Tyr Gly Gln Gly Ala Gly Ser Ser Ala
        130                 135                 140

Ala Ala Ala Ala Ala Ala Ala Ala Ala Gly Gly Gln Gly Gly
145                 150                 155                 160

Gln Gly Gln Gly Gly Tyr Gly Gln Gly Ser Gly Gly Ser Ala Ala Ala
            165                 170                 175

Ala Ala Ala Ala Ala Ala Ala Ala Ala Ala Gly Arg Gly Gln
        180                 185                 190

Gly Gly Tyr Gly Gln Gly Ser Gly Gly Asn Ala Ala Ala Ala Ala
    195                 200                 205

Ala Ala Ala Ala Ala Ala Ala Ala Gly Gln Gly Gly Gln Gly Gly
210                 215                 220

Tyr Gly Arg Gln Ser Gln Gly Ala Gly Ser Ala Ala Ala Ala Ala
225                 230                 235                 240

Ala Ala Ala Ala Ala Ala Ala Gly Ser Gly Gln Gly Gly Tyr Gly
            245                 250                 255

Gly Gln Gly Gln Gly Gly Tyr Gly Gln Ser Ser Ala Ser Ala Ser Ala
        260                 265                 270

Ala Ala Ser Ala Ala Ser Thr Val Ala Asn Ser Val Ser Arg Leu Ser
    275                 280                 285

Ser Pro Ser Ala Val Ser Arg Val Ser Ser Ala Val Ser Ser Leu Val
        290                 295                 300

Ser Asn Gly Gln Val Asn Met Ala Ala Leu Pro Asn Ile Ile Ser Asn
305                 310                 315                 320

Ile Ser Ser Ser Val Ser Ala Ser Ala Pro Gly Ala Ser Gly Cys Glu
            325                 330                 335

Val Ile Val Gln Ala Leu Leu Glu Val Ile Thr Ala Leu Val Gln Ile
                340                 345                 350

Val Ser Ser Ser Val Gly Tyr Ile Asn Pro Ser Ala Val Asn Gln
            355                 360                 365

Ile Thr Asn Val Val Ala Asn Ala Met Ala Gln Val Met Gly
        370                 375                 380

<210> SEQ ID NO 16
<211> LENGTH: 270
<212> TYPE: PRT
<213> ORGANISM: Euprosthenops australis

<400> SEQUENCE: 16

Gly Ser Gly Asn Ser Gly Gln Gly Gly Phe Ser Gln Gly Ala
1               5                   10                  15

Gly Gly Asn Ala Ala Ala Ala Ala Ala Ala Ala Ala Ala Ala
            20                  25                  30

Ala Ala Gln Gln Gly Gly Gln Gly Gly Phe Gly Arg Gly Gln Gly
        35                  40                  45

Gly Phe Gly Pro Gly Ala Gly Ser Ser Ala Ala Ala Ala Ala Ala
    50                  55                  60

Thr Ala Ala Ala Gly Gln Gly Gly Gln Gly Arg Gly Gly Phe Gly Gln
65                  70                  75                  80

Gly Ala Gly Ser Asn Ala Ala Ala Ala Ala Ala Ala Ala Ala Ala
                85                  90                  95

Ala Ala Ala Ala Gly Gln Gly Gly Gln Gly Gln Gly Phe Gly Gln
            100                 105                 110

Gly Thr Val Gly Asn Ala Ala Ala Ala Ala Ala Ala Ala Ala Ala
            115                 120                 125

Ala Ala Ala Gln Gln Gly Gly Gln Gly Gly Phe Gly Gly Gln Gly Gln
130                 135                 140

Arg Gly Phe Gly Gln Arg Ala Ala Ser Ala Val Ala Ser Ala Ala Ser
145                 150                 155                 160

Ala Ala Asp Val Gly Asn Thr Val Ala Asn Thr Val Ser Arg Leu Ser
                165                 170                 175

Ser Pro Ser Ala Ala Ser Arg Val Ser Ser Ala Val Ala Asn Leu Val
            180                 185                 190

Ser Asn Gly Gln Leu Asn Met Ala Ala Leu Pro Tyr Ile Ile Ser Asn
        195                 200                 205

Ile Ser Ser Ser Val Ser Ala Ser Val Pro Gly Ala Ser Gly Cys Glu
    210                 215                 220

Val Ile Val Gln Ala Leu Leu Glu Val Val Ala Ala Leu Cys Gln Ile
225                 230                 235                 240

Val Ser Ser Ser Asn Val Gly Tyr Ile Asn Pro Ser Ala Val Asn Asp
                245                 250                 255

Ile Thr Asn Val Val Ala Asn Ala Met Ala Gln Val Met Gly
            260                 265                 270

<210> SEQ ID NO 17
<211> LENGTH: 513
<212> TYPE: PRT
<213> ORGANISM: Euprosthenops australis

<400> SEQUENCE: 17

Met Lys Ala Ser His Thr Thr Pro Trp Thr Asn Pro Gly Leu Ala Glu
1               5                   10                  15

```
Asn Phe Met Asn Ser Phe Met Gln Gly Leu Ser Ser Met Pro Gly Phe
                20                  25                  30

Thr Ala Ser Gln Leu Asp Asp Met Ser Thr Ile Ala Gln Ser Met Val
            35                  40                  45

Gln Ser Ile Gln Ser Leu Ala Ala Gln Gly Arg Thr Ser Pro Asn Lys
 50                  55                  60

Leu Gln Ala Leu Asn Met Ala Phe Ala Ser Ser Met Ala Glu Ile Ala
 65                  70                  75                  80

Ala Ser Glu Glu Gly Gly Ser Leu Ser Thr Lys Thr Ser Ser Ile
                85                  90                  95

Ala Ser Ala Met Ser Asn Ala Phe Leu Gln Thr Gly Val Val Asn
                100                 105                 110

Gln Pro Phe Ile Asn Glu Ile Thr Gln Leu Val Ser Met Phe Ala Gln
            115                 120                 125

Ala Gly Met Asn Asp Val Ser Ala Gly Tyr Gly Gln Gly Ala Gly Ser
 130                 135                 140

Ser Ala Ala Ala Ala Ala Ala Ala Ala Ala Ala Ala Ala Ala Ala Gly
 145                 150                 155                 160

Arg Gly Gln Gly Gly Tyr Gly Gln Gly Ser Gly Gly Asn Ala Ala Ala
                165                 170                 175

Ala Ala Ala Ala Ala Ala Ala Ala Ala Ser Gly Gln Gly Ser Gln Gly
                180                 185                 190

Gly Gln Gly Gly Gln Gly Gln Gly Gly Tyr Gly Gln Gly Ala Gly Ser
                195                 200                 205

Ser Ala Ala Ala Ala Ala Ala Ala Ala Ala Ala Ala Ala Ala Ser Gly
 210                 215                 220

Arg Gly Gln Gly Gly Tyr Gly Gln Gly Ala Gly Gly Asn Ala Ala Ala
225                 230                 235                 240

Ala Ala Ala Ala Ala Ala Ala Ala Ala Gly Gln Gly Gly Gln
                245                 250                 255

Gly Gly Tyr Gly Gly Leu Gly Gln Gly Gly Tyr Gly Gln Gly Ala Gly
                260                 265                 270

Ser Ser Ala Ala Ala Ala Ala Ala Ala Ala Ala Ala Ala Gly Gly
 275                 280                 285

Gln Gly Gly Gln Gly Gln Gly Gly Tyr Gly Gln Gly Ser Gly Gly Ser
 290                 295                 300

Ala Ala Ala Ala Ala Ala Ala Ala Ala Ala Ala Ala Ala Ala Ala Gly
 305                 310                 315                 320

Arg Gly Gln Gly Gly Tyr Gly Gln Gly Ser Gly Gly Asn Ala Ala Ala
                325                 330                 335

Ala Ala Ala Ala Ala Ala Ala Ala Ala Ala Gly Gln Gly Gly
                340                 345                 350

Gln Gly Gly Tyr Gly Arg Gln Ser Gln Gly Ala Gly Ser Ala Ala Ala
                355                 360                 365

Ala Ala Ala Ala Ala Ala Ala Ala Ala Ala Gly Ser Gly Gln Gly
                370                 375                 380

Gly Tyr Gly Gly Gln Gly Gln Gly Gly Tyr Gly Gln Ser Ser Ala Ser
 385                 390                 395                 400

Ala Ser Ala Ala Ala Ser Ala Ala Ser Thr Val Ala Asn Ser Val Ser
                405                 410                 415

Arg Leu Ser Ser Pro Ser Ala Val Ser Arg Val Ser Ser Ala Val Ser
                420                 425                 430
```

```
Ser Leu Val Ser Asn Gly Gln Val Asn Met Ala Ala Leu Pro Asn Ile
            435                 440                 445

Ile Ser Asn Ile Ser Ser Val Ser Ala Ser Ala Pro Gly Ala Ser
    450                 455                 460

Gly Cys Glu Val Ile Val Gln Ala Leu Leu Glu Val Ile Thr Ala Leu
465                 470                 475                 480

Val Gln Ile Val Ser Ser Ser Val Gly Tyr Ile Asn Pro Ser Ala
                485                 490                 495

Val Asn Gln Ile Thr Asn Val Val Ala Asn Ala Met Ala Gln Val Met
                500                 505                 510

Gly

<210> SEQ ID NO 18
<211> LENGTH: 640
<212> TYPE: PRT
<213> ORGANISM: Euprosthenops australis

<400> SEQUENCE: 18

Ser His Thr Thr Pro Trp Thr Asn Pro Gly Leu Ala Glu Asn Phe Met
1               5                   10                  15

Asn Ser Phe Met Gln Gly Leu Ser Ser Met Pro Gly Phe Thr Ala Ser
                20                  25                  30

Gln Leu Asp Asp Met Ser Thr Ile Ala Gln Ser Met Val Gln Ser Ile
            35                  40                  45

Gln Ser Leu Ala Ala Gln Gly Arg Thr Ser Pro Asn Lys Leu Gln Ala
    50                  55                  60

Leu Asn Met Ala Phe Ala Ser Ser Met Ala Glu Ile Ala Ala Ser Glu
65                  70                  75                  80

Glu Gly Gly Gly Ser Leu Ser Thr Lys Thr Ser Ser Ile Ala Ser Ala
                85                  90                  95

Met Ser Asn Ala Phe Leu Gln Thr Thr Gly Val Val Asn Gln Pro Phe
            100                 105                 110

Ile Asn Glu Ile Thr Gln Leu Val Ser Met Phe Ala Gln Ala Gly Met
        115                 120                 125

Asn Asp Gly Gly Gly Thr Pro Trp Thr Asn Pro Gly Leu Ala Glu Asn
    130                 135                 140

Phe Met Asn Ser Phe Met Gln Gly Leu Ser Ser Met Pro Gly Phe Thr
145                 150                 155                 160

Ala Ser Gln Leu Asp Asp Met Ser Thr Ile Ala Gln Ser Met Val Gln
                165                 170                 175

Ser Ile Gln Ser Leu Ala Ala Gln Gly Arg Thr Ser Pro Asn Lys Leu
            180                 185                 190

Gln Ala Leu Asn Met Ala Phe Ala Ser Ser Met Ala Glu Ile Ala Ala
        195                 200                 205

Ser Glu Glu Gly Gly Gly Ser Leu Ser Thr Lys Thr Ser Ser Ile Ala
    210                 215                 220

Ser Ala Met Ser Asn Ala Phe Leu Gln Thr Thr Gly Val Val Asn Gln
225                 230                 235                 240

Pro Phe Ile Asn Glu Ile Thr Gln Leu Val Ser Met Phe Ala Gln Ala
                245                 250                 255

Gly Met Asn Asp Val Ser Ala Gly Tyr Gly Gln Gly Ala Gly Ser Ser
            260                 265                 270

Ala Ala Ala Ala Ala Ala Ala Ala Ala Ala Ala Ala Ala Gly Arg
        275                 280                 285
```

```
Gly Gln Gly Gly Tyr Gly Gln Gly Ser Gly Gly Asn Ala Ala Ala
    290                 295                 300
Ala Ala Ala Ala Ala Ala Ala Ala Ser Gly Gln Gly Ser Gln Gly Gly
305                 310                 315                 320
Gln Gly Gly Gln Gly Gln Gly Gly Tyr Gly Gln Gly Ala Gly Ser Ser
                325                 330                 335
Ala Ala Ala Ala Ala Ala Ala Ala Ala Ala Ala Ala Ala Ser Gly Arg
                340                 345                 350
Gly Gln Gly Gly Tyr Gly Gln Gly Ala Gly Gly Asn Ala Ala Ala
                355                 360                 365
Ala Ala Ala Ala Ala Ala Ala Ala Ala Ala Gly Gln Gly Gly Gln Gly
            370                 375                 380
Gly Tyr Gly Gly Leu Gly Gln Gly Gly Tyr Gly Gln Gly Ala Gly Ser
385                 390                 395                 400
Ser Ala Ala Ala Ala Ala Ala Ala Ala Ala Ala Ala Ala Gly Gly Gln
                405                 410                 415
Gly Gly Gln Gly Gln Gly Gly Tyr Gly Gln Gly Ser Gly Gly Ser Ala
                420                 425                 430
Ala Ala Ala Ala Ala Ala Ala Ala Ala Ala Ala Ala Ala Ala Gly Arg
            435                 440                 445
Gly Gln Gly Gly Tyr Gly Gln Gly Ser Gly Gly Asn Ala Ala Ala Ala
            450                 455                 460
Ala Ala Ala Ala Ala Ala Ala Ala Ala Gly Gln Gly Gly Gln
465                 470                 475                 480
Gly Gly Tyr Gly Arg Gln Ser Gln Gly Ala Gly Ser Ala Ala Ala Ala
                485                 490                 495
Ala Ala Ala Ala Ala Ala Ala Ala Ala Gly Ser Gly Gln Gly Gly
            500                 505                 510
Tyr Gly Gly Gln Gly Gln Gly Gly Tyr Gly Gln Ser Ser Ala Ser Ala
            515                 520                 525
Ser Ala Ala Ala Ser Ala Ala Ser Thr Val Ala Asn Ser Val Ser Arg
            530                 535                 540
Leu Ser Ser Pro Ser Ala Val Ser Arg Val Ser Ser Ala Val Ser Ser
545                 550                 555                 560
Leu Val Ser Asn Gly Gln Val Asn Met Ala Ala Leu Pro Asn Ile Ile
                565                 570                 575
Ser Asn Ile Ser Ser Ser Val Ser Ala Ser Ala Pro Gly Ala Ser Gly
            580                 585                 590
Cys Glu Val Ile Val Gln Ala Leu Leu Glu Val Ile Thr Ala Leu Val
            595                 600                 605
Gln Ile Val Ser Ser Ser Val Gly Tyr Ile Asn Pro Ser Ala Val
            610                 615                 620
Asn Gln Ile Thr Asn Val Val Ala Asn Ala Met Ala Gln Val Met Gly
625                 630                 635                 640

<210> SEQ ID NO 19
<211> LENGTH: 270
<212> TYPE: PRT
<213> ORGANISM: Artificial Sequence
<220> FEATURE:
<223> OTHER INFORMATION: Engineered 4RepCT variant

<400> SEQUENCE: 19

Gly Pro Asn Ser Arg Gly Asp Ala Gly Ala Ala Ser Gly Gln Gly Gly
1               5                   10                  15
```

Tyr Gly Gly Leu Gly Gln Gly Gly Tyr Gly Gln Gly Ala Gly Ser Ser
            20                  25                  30

Ala Ala Ala Ala Ala Ala Ala Ala Ala Ala Gly Gln Gly Gly
        35                  40                  45

Gln Gly Gln Gly Gly Tyr Gly Gln Gly Ser Gly Gly Ser Ala Ala Ala
        50                  55                  60

Ala Ala Ala Ala Ala Ala Ala Ala Ala Ala Gly Arg Gly Gln
65                  70                  75                  80

Gly Gly Tyr Gly Gln Gly Ser Gly Gly Asn Ala Ala Ala Ala Ala
                85                  90                  95

Ala Ala Ala Ala Ala Ala Ala Ala Gly Gln Gly Gly Gln Gly Gly
            100                 105                 110

Tyr Gly Arg Gln Ser Gln Gly Ala Gly Ser Ala Ala Ala Ala Ala
            115                 120                 125

Ala Ala Ala Ala Ala Ala Ala Gly Ser Gly Gln Gly Gly Tyr Gly
            130                 135                 140

Gly Gln Gly Gln Gly Gly Tyr Gly Gln Ser Ser Ala Ser Ala Ser Ala
145                 150                 155                 160

Ala Ala Ser Ala Ala Ser Thr Val Ala Asn Ser Val Ser Arg Leu Ser
            165                 170                 175

Ser Pro Ser Ala Val Ser Arg Val Ser Ser Ala Val Ser Ser Leu Val
            180                 185                 190

Ser Asn Gly Gln Val Asn Met Ala Ala Leu Pro Asn Ile Ile Ser Asn
            195                 200                 205

Ile Ser Ser Ser Val Ser Ala Ser Ala Pro Gly Ala Ser Gly Cys Glu
210                 215                 220

Val Ile Val Gln Ala Leu Leu Glu Val Ile Thr Ala Leu Val Gln Ile
225                 230                 235                 240

Val Ser Ser Ser Ser Val Gly Tyr Ile Asn Pro Ser Ala Val Asn Gln
            245                 250                 255

Ile Thr Asn Val Val Ala Asn Ala Met Ala Gln Val Met Gly
            260                 265                 270

<210> SEQ ID NO 20
<211> LENGTH: 270
<212> TYPE: PRT
<213> ORGANISM: Artificial Sequence
<220> FEATURE:
<223> OTHER INFORMATION: Engineered 4RepCT variant

<400> SEQUENCE: 20

Gly Pro Asn Ser Arg Gly Glu Ala Gly Ala Ala Ser Gly Gln Gly Gly
1               5                   10                  15

Tyr Gly Gly Leu Gly Gln Gly Gly Tyr Gly Gln Gly Ala Gly Ser Ser
            20                  25                  30

Ala Ala Ala Ala Ala Ala Ala Ala Ala Ala Gly Gln Gly Gly
        35                  40                  45

Gln Gly Gln Gly Gly Tyr Gly Gln Gly Ser Gly Gly Ser Ala Ala Ala
        50                  55                  60

Ala Ala Ala Ala Ala Ala Ala Ala Ala Ala Gly Arg Gly Gln
65                  70                  75                  80

Gly Gly Tyr Gly Gln Gly Ser Gly Gly Asn Ala Ala Ala Ala Ala
                85                  90                  95

Ala Ala Ala Ala Ala Ala Ala Ala Gly Gln Gly Gly Gln Gly Gly
            100                 105                 110

```
Tyr Gly Arg Gln Ser Gln Gly Ala Gly Ser Ala Ala Ala Ala Ala
            115                 120                 125

Ala Ala Ala Ala Ala Ala Ala Gly Ser Gly Gln Gly Gly Tyr Gly
        130                 135                 140

Gly Gln Gly Gln Gly Gly Tyr Gly Gln Ser Ser Ala Ser Ala Ser Ala
145                 150                 155                 160

Ala Ala Ser Ala Ala Ser Thr Val Ala Asn Ser Val Ser Arg Leu Ser
                165                 170                 175

Ser Pro Ser Ala Val Ser Arg Val Ser Ser Ala Val Ser Ser Leu Val
                180                 185                 190

Ser Asn Gly Gln Val Asn Met Ala Ala Leu Pro Asn Ile Ile Ser Asn
        195                 200                 205

Ile Ser Ser Ser Val Ser Ala Ser Ala Pro Gly Ala Ser Gly Cys Glu
    210                 215                 220

Val Ile Val Gln Ala Leu Leu Glu Val Ile Thr Ala Leu Val Gln Ile
225                 230                 235                 240

Val Ser Ser Ser Ser Val Gly Tyr Ile Asn Pro Ser Ala Val Asn Gln
                245                 250                 255

Ile Thr Asn Val Val Ala Asn Ala Met Ala Gln Val Met Gly
            260                 265                 270

<210> SEQ ID NO 21
<211> LENGTH: 272
<212> TYPE: PRT
<213> ORGANISM: Artificial Sequence
<220> FEATURE:
<223> OTHER INFORMATION: Engineered 4RepCT variant

<400> SEQUENCE: 21

Gly Pro Asn Ser Ile Lys Val Ala Val Ala Gly Ala Arg Ser Gly Gln
1               5                   10                  15

Gly Gly Tyr Gly Gly Leu Gly Gln Gly Gly Tyr Gly Gln Gly Ala Gly
            20                  25                  30

Ser Ser Ala Ala Ala Ala Ala Ala Ala Ala Ala Ala Ala Gly Gln
        35                  40                  45

Gly Gly Gln Gly Gln Gly Gly Tyr Gly Gln Gly Ser Gly Gly Ser Ala
    50                  55                  60

Ala Ala Ala Ala Ala Ala Ala Ala Ala Ala Ala Ala Ala Ala Gly Arg
65                  70                  75                  80

Gly Gln Gly Gly Tyr Gly Gln Gly Ser Gly Gly Asn Ala Ala Ala
                85                  90                  95

Ala Ala Ala Ala Ala Ala Ala Ala Ala Gly Gln Gly Gly Gln
            100                 105                 110

Gly Gly Tyr Gly Arg Gln Ser Gln Gly Ala Gly Ser Ala Ala Ala Ala
            115                 120                 125

Ala Ala Ala Ala Ala Ala Ala Ala Gly Ser Gly Gln Gly Gly
        130                 135                 140

Tyr Gly Gly Gln Gly Gln Gly Gly Tyr Gly Gln Ser Ser Ala Ser Ala
145                 150                 155                 160

Ser Ala Ala Ala Ser Ala Ala Ser Thr Val Ala Asn Ser Val Ser Arg
                165                 170                 175

Leu Ser Ser Pro Ser Ala Val Ser Arg Val Ser Ser Ala Val Ser Ser
                180                 185                 190

Leu Val Ser Asn Gly Gln Val Asn Met Ala Ala Leu Pro Asn Ile Ile
            195                 200                 205
```

Ser Asn Ile Ser Ser Ser Val Ser Ala Ser Ala Pro Gly Ala Ser Gly
    210                 215                 220

Cys Glu Val Ile Val Gln Ala Leu Leu Glu Val Ile Thr Ala Leu Val
225                 230                 235                 240

Gln Ile Val Ser Ser Ser Val Gly Tyr Ile Asn Pro Ser Ala Val
            245                 250                 255

Asn Gln Ile Thr Asn Val Val Ala Asn Ala Met Ala Gln Val Met Gly
            260                 265                 270

<210> SEQ ID NO 22
<211> LENGTH: 267
<212> TYPE: PRT
<213> ORGANISM: Artificial Sequence
<220> FEATURE:
<223> OTHER INFORMATION: Engineered 4RepCT variant

<400> SEQUENCE: 22

Gly Pro Asn Ser Tyr Ile Gly Ser Arg Gly Gln Gly Gly Tyr Gly Gly
1               5                   10                  15

Leu Gly Gln Gly Gly Tyr Gly Gln Gly Ala Gly Ser Ser Ala Ala Ala
            20                  25                  30

Ala Ala Ala Ala Ala Ala Ala Ala Ala Gly Gln Gly Gly Gln Gly Gln
            35                  40                  45

Gly Gly Tyr Gly Gln Gly Ser Gly Ser Ala Ala Ala Ala Ala
    50                  55                  60

Ala Ala Ala Ala Ala Ala Ala Ala Gly Arg Gly Gln Gly Gly Tyr
65                  70                  75                  80

Gly Gln Gly Ser Gly Gly Asn Ala Ala Ala Ala Ala Ala Ala Ala
            85                  90                  95

Ala Ala Ala Ala Ala Ala Gly Gln Gly Gly Gln Gly Tyr Gly Arg
            100                 105                 110

Gln Ser Gln Gly Ala Gly Ser Ala Ala Ala Ala Ala Ala Ala Ala
        115                 120                 125

Ala Ala Ala Ala Ala Gly Ser Gly Gln Gly Gly Tyr Gly Gln Gly
        130                 135                 140

Gln Gly Gly Tyr Gly Gln Ser Ser Ala Ser Ala Ser Ala Ala Ser
145                 150                 155                 160

Ala Ala Ser Thr Val Ala Asn Ser Val Ser Arg Leu Ser Ser Pro Ser
            165                 170                 175

Ala Val Ser Arg Val Ser Ser Ala Val Ser Ser Leu Val Ser Asn Gly
            180                 185                 190

Gln Val Asn Met Ala Ala Leu Pro Asn Ile Ile Ser Asn Ile Ser Ser
        195                 200                 205

Ser Val Ser Ala Ser Ala Pro Gly Ala Ser Gly Cys Glu Val Ile Val
    210                 215                 220

Gln Ala Leu Leu Glu Val Ile Thr Ala Leu Val Gln Ile Val Ser Ser
225                 230                 235                 240

Ser Ser Val Gly Tyr Ile Asn Pro Ser Ala Val Asn Gln Ile Thr Asn
            245                 250                 255

Val Val Ala Asn Ala Met Ala Gln Val Met Gly
            260                 265

<210> SEQ ID NO 23
<211> LENGTH: 5
<212> TYPE: PRT
<213> ORGANISM: Artificial Sequence
<220> FEATURE:

```
<223> OTHER INFORMATION: Cell-binding motif

<400> SEQUENCE: 23

Ile Lys Val Ala Val
1               5

<210> SEQ ID NO 24
<211> LENGTH: 5
<212> TYPE: PRT
<213> ORGANISM: Artificial Sequence
<220> FEATURE:
<223> OTHER INFORMATION: Cell-binding motif

<400> SEQUENCE: 24

Tyr Ile Gly Ser Arg
1               5

<210> SEQ ID NO 25
<211> LENGTH: 5
<212> TYPE: PRT
<213> ORGANISM: Artificial Sequence
<220> FEATURE:
<223> OTHER INFORMATION: Cell-binding motif

<400> SEQUENCE: 25

Glu Pro Asp Ile Met
1               5

<210> SEQ ID NO 26
<211> LENGTH: 5
<212> TYPE: PRT
<213> ORGANISM: Artificial Sequence
<220> FEATURE:
<223> OTHER INFORMATION: Cell-binding motif

<400> SEQUENCE: 26

Asn Lys Asp Ile Leu
1               5
```

METHODS AND COMBINATION COMPRISING EUKARYOTIC CELLS AND RECOMBINANT SPIDER SILK PROTEIN

CROSS REFERENCE TO RELATED APPLICATIONS

This application is the National Phase of PCT/SE2011/050448 filed on Apr. 12, 2011, which claims priority under 35 U.S.C. 119(e) to U.S. Provisional Application No. 61/323,226 filed on Apr. 12, 2010 and under 35 U.S.C. 119(a) to Patent Application Nos. 10159694.8 filed in Europe on Apr. 12, 2010 and 11153543.1 filed in Europe on Feb. 7, 2011, all of which are hereby expressly incorporated by reference into the present application.

FIELD OF THE INVENTION

The present invention relates to the fields of eukaryotic cell culture and tissue engineering, and provides methods and a combination for eukaryotic cell culture and preparation, wherein a polymer of a spider silk protein is used as a cell scaffold material.

BACKGROUND

Spider silks are nature's high-performance polymers, obtaining extraordinary toughness due to a combination of strength and elasticity. Spiders have up to seven different glands which produce a variety of silk types with different mechanical properties and functions. Dragline silk, produced by the major ampullate gland, is the toughest fiber, and on a weight basis it outperforms man-made materials, such as tensile steel. The properties of dragline silk are attractive in development of new materials for medical or technical purposes.

Dragline silk consists of two main polypeptides, mostly referred to as major ampullate spidroin (MaSp) 1 and 2, but e.g. as ADF-3 and ADF-4 in *Araneus diadematus*. These proteins have molecular masses in the range of 200-720 kDa. The genes coding for dragline proteins of *Latrodectus hesperus* are the only ones that have been completely characterized, and the MaSp1 and MaSp2 genes encode 3129 and 3779 amino acids, respectively (Ayoub N A et al. PLoS ONE 2(6): e514, 2007). The properties of dragline silk polypeptides are discussed in Huemmerich, D. et al. Curr. Biol. 14, 2070-2074 (2004).

Spider dragline silk proteins, or MaSps, have a tripartite composition; a non-repetitive N-terminal domain, a central repetitive region comprised of many iterated poly-Ala/Gly segments, and a non-repetitive C-terminal domain. It is generally believed that the repetitive region forms intermolecular contacts in the silk fibers, while the precise functions of the terminal domains are less clear. It is also believed that in association with fiber formation, the repetitive region undergoes a structural conversion from random coil and α-helical conformation to β-sheet structure. The C-terminal region of spidroins is generally conserved between spider species and silk types. The N-terminal domain of spider silks is the most conserved region (Rising, A. et al. Biomacromolecules 7, 3120-3124 (2006)).

WO03/057727 discloses expression of soluble recombinant silk polypeptides in mammalian cell lines and animals. The obtained silk polypeptides exhibit poor solubility in aqueous media and/or form precipitates. Since the obtained silk polypeptides do not polymerise spontaneously, spinning is required to obtain polymers or fibers.

WO07/078239 and Stark, M. et al. Biomacromolecules 8, 1695-1701, (2007) disclose a miniature spider silk protein consisting of a repetitive fragment with a high content of Ala and Gly and a C-terminal fragment of a protein, as well as soluble fusion proteins comprising the spider silk protein. Fibers of the spider silk protein are obtained spontaneously upon liberation of the spider silk protein from its fusion partner. The small fusion unit is sufficient and necessary for the fiber formation.

Hedhammar, M. et al. Biochemistry 47, 3407-3417, (2008) study the thermal, pH and salt effects on the structure and aggregation and/or polymerisation of recombinant N- and C-terminal spidroin domains and a repetitive spidroin domain containing four poly-Ala and Gly rich co-blocks.

In vitro studies on the biocompatibility of recombinant spider silk are so far few, and the materials studied vary a lot in amino acid sequence, mode of production and format.

DESCRIPTION OF THE INVENTION

In a first aspect, the invention provides a method for the cultivation of eukaryotic cells, comprising
  providing a sample of eukaryotic cells to be cultured;
  applying said sample to a cell scaffold material; and
  maintaining said cell scaffold material having cells applied thereto under conditions suitable for cell culture. The cell scaffold material comprises a polymer of a spider silk protein.

In a second aspect, the invention provides a method for the preparation of eukaryotic cells, comprising:
  providing a sample of eukaryotic cells;
  applying said sample to a cell scaffold material;
  maintaining said cell scaffold material having cells applied thereto under conditions suitable for cell culture; and
  preparing a sample of cells from said cell scaffold material. The cell scaffold material comprises a polymer of a spider silk protein.

It has been found by the present inventors that a cell scaffold material comprising a polymer of a spider silk protein provides a beneficial environment for the cultivation of eukaryotic cells in a variety of different settings. Furthermore, this environment enables the establishment of cultures of cells that are otherwise very difficult, very costly or even impossible to culture in a laboratory, and for the establishment of cell-containing materials useful for tissue engineering and/or transplantation.

In some embodiments thereof, the cultivation or preparation methods may be performed in conditions comprising maintaining the cell scaffold material having cells applied thereto in a serum-free medium. The possibility to culture cells in a serum-free medium affords a cost-efficient and controlled alternative to the use of serum-containing media and/or media containing specific growth factors or extracellular matrix (ECM) components. This type of culture media is often very expensive, sometimes even prohibitively so, and heterogeneous.

In a third aspect, the invention provides a combination of eukaryotic cells and a cell scaffold material comprising a polymer of a spider silk protein. Such a combination according to the invention may be presented in a variety of different formats, and tailored to suit the needs of a specific situation. It is contemplated, for example, that the inventive combination may be useful as a cell-containing implant for the replacement of cells in damaged or diseased tissue.

In some embodiments of the methods and combination presented herein, the eukaryotic cells are mammalian cells, for example human cells. In other embodiments, the eukaryotic cells are non-mammalian cells, such as insect or yeast cells.

Non-limiting examples of mammalian cells that may be cultivated or prepared by the methods or included in the combination according to the invention are listed in the following multi-level listing:

Cells of the Integumentary System
    Keratinizing Epithelial Cells
    Epidermal keratinocyte (differentiating epidermal cell)
    Epidermal basal cell (stem cell)
    Keratinocyte of fingernails and toenails
    Nail bed basal cell (stem cell)
    Medullary hair shaft cell
    Cortical hair shaft cell
    Cuticular hair shaft cell
    Cuticular hair root sheath cell
    Hair root sheath cell of Huxley's layer
    Hair root sheath cell of Henle's layer
    External hair root sheath cell
    Hair matrix cell (stem cell)
    Wet Stratified Barrier Epithelial Cells
    Surface epithelial cell of stratified squamous epithelium of cornea, tongue, oral cavity, esophagus, anal canal, distal urethra and vagina
    Basal cell (stem cell) of epithelia of cornea, tongue, oral cavity, esophagus, anal canal, distal urethra and vagina
    Urinary epithelium cell (lining urinary bladder and urinary ducts)

Gland Cells
    Exocrine Secretory Epithelial Cells
    Salivary gland mucous cell (polysaccharide-rich secretion)
    Salivary gland serous cell (glycoprotein enzyme-rich secretion)
    von Ebner's gland cell in tongue (washes taste buds)
    Mammary gland cell (milk secretion)
    Lacrimal gland cell (tear secretion)
    Ceruminous gland cell in ear (wax secretion)
    Eccrine sweat gland dark cell (glycoprotein secretion)
    Eccrine sweat gland clear cell (small molecule secretion)
    Apocrine sweat gland cell (odoriferous secretion, sex-hormone sensitive)
    Gland of Moll cell in eyelid (specialized sweat gland)
    Sebaceous gland cell (lipid-rich sebum secretion)
    Bowman's gland cell in nose (washes olfactory epithelium)
    Brunner's gland cell in duodenum (enzymes and alkaline mucus)
    Seminal vesicle cell (secretes seminal fluid components, including fructose for swimming sperm)
    Prostate gland cell (secretes seminal fluid components)
    Bulbourethral gland cell (mucus secretion)
    Bartholin's gland cell (vaginal lubricant secretion)
    Gland of Littre cell (mucus secretion)
    Uterus endometrium cell (carbohydrate secretion)
    Isolated goblet cell of respiratory and digestive tracts (mucus secretion)
    Stomach lining mucous cell (mucus secretion)
    Gastric gland zymogenic cell (pepsinogen secretion)
    Gastric gland oxyntic cell, parietal cell (hydrochloric acid secretion)
    Enterochromaffin like (ECL) cells (release histamine)
    Pancreatic acinar cell (bicarbonate and digestive enzyme secretion)
    Paneth cell of small intestine (lysozyme secretion)
    Type II pneumocyte of lung (surfactant secretion)
    Clara cell of lung Hormone Secreting Cells
    Anterior pituitary cells
        Somatotropes
        Lactotropes
        Thyrotropes
        Gonadotropes
        Corticotropes
    Intermediate pituitary cell, secreting melanocyte-stimulating hormone
    Magnocellular neurosecretory cells
        secreting oxytocin
        secreting vasopressin
    Gut and respiratory tract cells
        Cells included in Islets of Langerhans:
            Alpha cells (produce glucagon), beta cells (insulin producing cells), delta cells (somatostatin producing cells), pp cells (produce pancreatic polypeptide), epsilon cells (produce ghrelin)
        secreting serotonin
        secreting endorphin
        secreting gastrin
        secreting secretin
        secreting cholecystokinin
        secreting bombesin
    Thyroid gland cells
        Thyroid epithelial cell
        Parafollicular cell
    Parathyroid gland cells
        Parathyroid chief cell
        Oxyphil cell
    Adrenal gland cells
        Chromaffin cells
        secreting steroid hormones (mineralcorticoids, androgens and gluco corticoids)
    Leydig cell of testes secreting testosterone
    Theca interna cell of ovarian follicle secreting estrogen
    Corpus luteum cell of ruptured ovarian follicle secreting progesterone
        Granulosa lutein cells
        Theca lutein cells
    Juxtaglomerular cell (renin secretion)
    Macula densa cell of kidney
    Peripolar cell of kidney
    Mesangial cell of kidney Metabolism and Storage Cells
    Hepatocyte (liver cell)
    White fat cell (adipocytes/blasts)
    Brown fat cell
    Liver lipocyte Barrier Function Cells (Lung, Gut, Exocrine Glands and Urogenital Tract)
    Kidney
    Kidney glomerulus parietal cell
    Kidney glomerulus podocyte
    Kidney proximal tubule brush border cell
    Loop of Henle thin segment cell
    Kidney distal tubule cell
    Kidney collecting duct cell
    Other
    Type I pneumocyte (lining air space of lung)
    Pancreatic duct cell (centroacinar cell)

Nonstriated duct cell (of sweat gland, salivary gland, mammary gland, etc.)
  Principal cell
  Intercalated cell
Duct cell (of seminal vesicle, prostate gland, etc.)
Intestinal brush border cell (with microvilli)
Exocrine gland striated duct cell
Gall bladder epithelial cell
Ductulus efferens nonciliated cell
Epididymal principal cell
Epididymal basal cell
Epithelial Cells Lining Closed Internal Body Cavities
  Microvascular endothelial cells
  Blood vessel and lymphatic vascular endothelial fenestrated cell
  Blood vessel and lymphatic vascular endothelial continuous cell
  Blood vessel and lymphatic vascular endothelial splenic cell
  Synovial cell (lining joint cavities, hyaluronic acid secretion)
  Serosal cell (lining peritoneal, pleural, and pericardial cavities)
  Squamous cell (lining perilymphatic space of ear)
  Squamous cell (lining endolymphatic space of ear)
  Columnar cell of endolymphatic sac with microvilli (lining endolymphatic space of ear)
  Columnar cell of endolymphatic sac without microvilli (lining endolymphatic space of ear)
  Dark cell (lining endolymphatic space of ear)
  Vestibular membrane cell (lining endolymphatic space of ear)
  Stria vascularis basal cell (lining endolymphatic space of ear)
  Stria vascularis marginal cell (lining endolymphatic space of ear)
  Cell of Claudius (lining endolymphatic space of ear)
  Cell of Boettcher (lining endolymphatic space of ear)
  Choroid plexus cell (cerebrospinal fluid secretion)
  Pia-arachnoid squamous cell
  Pigmented ciliary epithelium cell of eye
  Nonpigmented ciliary epithelium cell of eye
  Corneal endothelial cell
  Peg cell (of Fallopian tube)
Ciliated Cells with Propulsive Function
  Respiratory tract ciliated cell
  Oviduct ciliated cell (in female)
  Uterine endometrial ciliated cell (in female)
  Rete testis ciliated cell (in male)
  Ductulus efferens ciliated cell (in male)
  Ciliated ependymal cell of central nervous system (lining brain cavities)
Extracellular Matrix Secretion Cells
  Ameloblast epithelial cell (tooth enamel secretion)
  Planum semilunatum epithelial cell of vestibular apparatus of ear (proteoglycan secretion)
  Organ of Corti interdental epithelial cell (secreting tectorial membrane covering hair cells)
  Loose connective tissue fibroblasts
  Corneal fibroblasts (corneal keratocytes)
  Tendon fibroblasts
  Bone marrow reticular tissue fibroblasts
  Other nonepithelial fibroblasts
  Pericyte
  Nucleus pulposus cell of intervertebral disc
  Cementoblast/cementocyte (tooth root bonelike cementum secretion)
  Odontoblast/odontocyte (tooth dentin secretion)
  Hyaline cartilage chondrocyte
  Fibrocartilage chondrocyte
  Elastic cartilage chondrocyte
  Osteoblast/osteocyte
  Osteoprogenitor cell (stem cell of osteoblasts)
  Hyalocyte of vitreous body of eye
  Stellate cell of perilymphatic space of ear
  Hepatic stellate cell (Ito cell)
  Pancreatic stellate cell
Contractile Cells
  Skeletal muscle cells
    Red skeletal muscle cell (slow)
    White skeletal muscle cell (fast)
    Intermediate skeletal muscle cell
    Nuclear bag cell of muscle spindle
    Nuclear chain cell of muscle spindle
  Satellite cell (stem cell)
  Heart muscle cells
    Ordinary heart muscle cell
    Nodal heart muscle cell
    Purkinje fiber cell
  Smooth muscle cell (various types)
  Myoepithelial cell of iris
  Myoepithelial cell of exocrine glands
Blood and Immune System Cells
  Megakaryocyte (platelet precursor)
  Monocyte
  Connective tissue macrophage (various types)
  Epidermal Langerhans cell
  Osteoclast (in bone)
  Dendritic cell (in lymphoid tissues)
  Microglial cell (in central nervous system)
  Neutrophil granulocyte
  Eosinophil granulocyte
  Basophil granulocyte
  Mast cell
  Helper T cell
  Suppressor T cell
  Cytotoxic T cell
  Natural Killer T cell
  B cell
  Natural killer cell
  Reticulocyte
  Committed progenitors for the blood and immune system (various types, e.g. megakaryocyte, myeloblast)
Cells of the Nervous System
  Sensory Transducer Cells
    Auditory inner hair cell of organ of Corti
    Auditory outer hair cell of organ of Corti
    Basal cell of olfactory epithelium (stem cell for olfactory neurons)
    Cold-sensitive primary sensory neurons
    Heat-sensitive primary sensory neurons
    Merkel cell of epidermis (touch sensor)
    Olfactory receptor neuron
    Pain-sensitive primary sensory neurons (various types)
    Photoreceptor cells of retina in eye:
      Photoreceptor rod cells
      Photoreceptor blue-sensitive cone cell of eye
      Photoreceptor green-sensitive cone cell of eye
      Photoreceptor red-sensitive cone cell of eye
    Proprioceptive primary sensory neurons (various types)
    Touch-sensitive primary sensory neurons (various types)
    Type I carotid body cell (blood pH sensor)
    Type II carotid body cell (blood pH sensor)

Type I hair cell of vestibular apparatus of ear (acceleration and gravity)
Type II hair cell of vestibular apparatus of ear (acceleration and gravity)
Type I taste bud cell
Autonomic Neuron Cells
  Cholinergic neural cell (various types)
  Adrenergic neural cell (various types)
  Peptidergic neural cell (various types)
Sense Organ and Peripheral Neuron Supporting Cells
  Inner pillar cell of organ of Corti
  Outer pillar cell of organ of Corti
  Inner phalangeal cell of organ of Corti
  Outer phalangeal cell of organ of Corti
  Border cell of organ of Corti
  Hensen cell of organ of Corti
  Vestibular apparatus supporting cell
  Taste bud supporting cell
  Olfactory epithelium supporting cell
  Schwann cell
  Satellite cell (encapsulating peripheral nerve cell bodies)
  Enteric glial cell
Central Nervous System Neurons and Glial Cells
  Astrocyte (various types)
  Neuron cells (large variety of types, still poorly classified)
  Oligodendrocyte
  Spindle neuron
Pineocyte (produce melatonin)
Lens Cells
  Anterior lens epithelial cell
  Crystallin-containing lens fiber cell
Pigment Cells
  Melanocyte
  Retinal pigmented epithelial cell
Germ Cells
  Oogonium/Oocyte
  Spermatid
  Spermatocyte
  Spermatogonium cell (stem cell for spermatocyte)
  Spermatozoon
Nurse Cells
  Ovarian follicle cell
  Sertoli cell (in testis)
  Thymus epithelial cell
Stem Cells and Progenitor Cells
  Embryonic stem cells
  Adult stem cells (e.g., hematopoietic stem cells, endothelial stem cells, epithelial stem cells, neural stem cells, mesenchymal stem cells) Progenitor cells (neural progenitor cells, lymphoid progenitor cells, satellite cells, endothelial progenitor cells, periosteal progenitor, pancreatic progenitor cells, satellite cells in muscles, hematopoietic progenitor cells)
  Amniotic stem cells (multipotent and can differentiate to cells of adipogenic, osteogenic, myogenic, endothelial, hepatic and also neuronal lines)
  Induced pluripotent stem cells In organs, there is usually a main tissue and sporadic tissues. The main tissue is the one that is unique for the specific organ. In an embodiment of the invention, it is contemplated that the cells for use in the methods or combination disclosed herein are main tissue cells, i.e. cells that contribute to the function of organs in their natural environment. Furthermore, in an embodiment, cells forming sporadic tissue, in particular connective tissue, are not included, since the role of connective tissue is considered to be fulfilled by the spider silk protein in this embodiment.

For example, the main tissue of the heart is the myocardium, while sporadic are the nerves, blood, connective etc. Below follows a non-limiting listing of examples of organ systems, whose main tissue cells may be useful in the methods or combination disclosed herein.

Circulatory system: pumping and channeling blood to and from the body and lungs with heart, blood and blood vessels.

Digestive system: digestion and processing food with salivary glands, esophagus, stomach, liver, gallbladder, pancreas, intestines, rectum and anus.

Endocrine system: communication within the body using hormones made by endocrine glands such as the hypothalamus, pituitary or pituitary gland, pineal body or pineal gland, pancreas, thyroid, parathyroids and adrenals, i.e., adrenal glands.

Excretory system: kidneys, ureters, bladder and urethra involved in fluid balance, electrolyte balance and excretion of urine.

Integumentary system: skin, hair and nails.

Lymphatic system: structures involved in the transfer of lymph between tissues and the blood stream, the lymph and the nodes and vessels that transport it including the endothelium.

Immune system: defending against disease-causing agents with leukocytes, tonsils, adenoids, thymus and spleen.

Muscular system: movement with muscles.

Nervous system: collecting, transferring and processing information with brain, spinal cord, peripheral nerves and nerves.

Reproductive system: the sex organs, such as ovaries, fallopian tubes, uterus, vagina, mammary glands, testes, vas deferens, seminal vesicles, prostate and penis.

Respiratory system: the organs used for breathing, the pharynx, larynx, trachea, bronchi, lungs and diaphragm.

Skeletal system: structural support and protection with bones, cartilage, ligaments and tendons.

Various different embodiments of the methods or combination disclosed herein may employ any sub-group or sub-listing of cells, or even individual cell types, from the above general listings of cell types and organ and tissue systems.

In a more specific embodiment, said mammalian cells are selected from the group consisting of stem cells and cells from islets of Langerhans (e.g. beta cells).

In a more specific embodiment, said cells are selected from embryonic stem cells, adult stem cells, induced pluripotent stem cells, amniotic stem cells and progenitor cells, and may in particular be selected from embryonic stem cells, adult stem cells and induced pluripotent stem cells.

In yet a specific embodiment, said cells are embryonic stem cells.

In yet a specific embodiment, said cells are adult stem cells selected from the group consisting of hematopoietic, neural, mesenchymal, mammary, endothelial, epithelial and olfactory stem cells, in particular selected from the group consisting of hematopoietic, neural and mesenchymal stem cells.

In yet a specific embodiment, said cells are progenitor cells selected from the group consisting of neural progenitor cells, mesenchymal progenitor cells and hematopoietic progenitor cells.

In yet a specific embodiment, the mammalian cells are neural stem cells (interchangeably denoted neural cortical stem cells), which may be provided as single cells or in the form of at least one neurosphere.

In yet a specific embodiment, the mammalian cells are insulin-producing beta cells, which may be provided as single cells or in the form of at least one islet of Langerhans.

In yet a specific embodiment, the mammalian cells are somatic cells, for example selected from the group consisting of hepatocytes, fibroblasts, keratinocytes and endothelial cells.

The cell scaffold material used in the context of the present disclosure comprises a polymer of a spider silk protein or polypeptide, also denoted "spidroin".

In one of the embodiments of the cell scaffold material, said spidroin consists of from 140 to 600 amino acid residues and comprises a repetitive fragment of from 70 to 300 amino acid residues derived from the repetitive fragment of a spider silk protein;

a C-terminal fragment of from 70 to 120 amino acid residues derived from the C-terminal fragment of a spider silk protein; and optionally an N-terminal fragment of from 100 to 160 amino acid residues derived from the N-terminal fragment of a spider silk protein.

The spidroin consists of from 140 to 600 amino acid residues, preferably from 280 to 600 amino acid residues, such as from 300 to 400 amino acid residues, more preferably from 340 to 380 amino acid residues. The small size is advantageous because longer spider silk proteins tend to form amorphous aggregates, which require use of harsh solvents for solubilisation and polymerisation. The protein fragments are covalently coupled, typically via a peptide bond.

In specific preferred embodiments, the spidroin for use in the cell scaffold material is selected from the group of proteins defined by the formulas NT-REP-CT and REP-CT.

The (optional) NT fragment has a high degree of similarity to the N-terminal amino acid sequence of spider silk proteins. As shown in FIG. 1, this amino acid sequence is well conserved among various species and spider silk proteins, including MaSp1 and MaSp2. See also the following Table 1:

TABLE 1

Spidroin NT fragments

| Code | Species and spidroin | GenBank acc. no. |
|---|---|---|
| Ea MaSp1 | *Euprosthenops australis* MaSp 1 | AM259067 |
| Lg MaSp1 | *Latrodectus geometricus* MaSp 1 | ABY67420 |
| Lh MaSp1 | *Latrodectus hesperus* MaSp 1 | ABY67414 |
| Nc MaSp1 | *Nephila clavipes* MaSp 1 | ACF19411 |
| At MaSp2 | *Argiope trifasciata* MaSp 2 | AAZ15371 |
| Lg MaSp2 | *Latrodectus geometricus* MaSp 2 | ABY67417 |
| Lh MaSp2 | *Latrodectus hesperus* MaSp 2 | ABR68855 |
| Nim MaSp2 | *Nephila inaurata madagascariensis* MaSp 2 | AAZ15322 |
| Nc MaSp2 | *Nephila clavipes* MaSp 2 | ACF19413 |
| Ab CySp1 | *Argiope bruennichi* cylindriform spidroin 1 | BAE86855 |
| Ncl CySp1 | *Nephila clavata* cylindriform spidroin 1 | BAE54451 |
| Lh TuSp1 | *Latrodectus hesperus* tubuliform spidroin | ABD24296 |
| Nc Flag | *Nephila clavipes* flagelliform silk protein | AF027972 |
| Nim Flag | *Nephila inaurata madagascariensis* flagelliform silk protein | AF218623 (translated) |

It is not critical which, if any, specific NT fragment is present in the spidroin of the cell scaffold material disclosed herein. Thus, the NT fragment according to the invention can be selected from any of the amino acid sequences shown in FIG. 1 or sequences with a high degree of similarity. A wide variety of N-terminal sequences can be used as spidroin in the cell scaffold material disclosed herein. Based on the homologous sequences of FIG. 1, the following sequence constitutes a consensus NT amino acid sequence:

(SEQ ID NO: 8)
QANTPWSSPNLADAFINSF(M/L)SA(A/I)SSSGAFSADQLDDMSTIG
(D/N/Q)TLMSAMD(N/S/K)MGRSG(K/R)STKSKLQALNMAFASSMA
EIAAAESGG(G/Q)SVGVKTNAISDALSSAFYQTTGSVNPQFV(N/S)E
IRSLI(G/N)M(F/L)(A/S)QASANEV.

The sequence of the NT fragment has at least 50% identity, preferably at least 60% identity, to the consensus amino acid sequence SEQ ID NO:8, which is based on the amino acid sequences of FIG. 1. In a preferred embodiment, the sequence of the NT fragment has at least 65% identity, preferably at least 70% identity, to the consensus amino acid sequence SEQ ID NO:8. In preferred embodiments, the NT fragment has furthermore 70%, preferably 80%, similarity to the consensus amino acid sequence SEQ ID NO:8.

A representative NT fragment in a protein for use in the cell scaffold material disclosed herein is the *Euprosthenops australis* sequence SEQ ID NO:6. According to an embodiment, the NT fragment has at least 80% identity to SEQ ID NO:6 or any individual amino acid sequence in FIG. 1. For example, the NT fragment has at least 90%, such as at least 95% identity, to SEQ ID NO:6 or any individual amino acid sequence in FIG. 1. The NT fragment may be identical to SEQ ID NO:6 or any individual amino acid sequence in FIG. 1, in particular to Ea MaSp1.

The NT fragment contains from 100 to 160 amino acid residues. It is preferred that the NT fragment contains at least 100, or more than 110, preferably more than 120, amino acid residues. It is also preferred that the NT fragment contains at most 160, or less than 140 amino acid residues. A typical NT fragment contains approximately 130-140 amino acid residues.

The REP fragment has a repetitive character, alternating between alanine-rich stretches and glycine-rich stretches. The REP fragment generally contains more than 70, such as more than 140, and less than 300, preferably less than 240, such as less than 200, amino acid residues, and can itself be divided into several L (linker) segments, A (alanine-rich) segments and G (glycine-rich) segments, as will be explained in more detail below. Typically, said linker segments, which are optional, are located at the REP fragment terminals, while the remaining segments are in turn alanine-rich and glycine-rich. Thus, the REP fragment can generally have either of the following structures, wherein n is an integer:

L(AG)$_n$L, such as L$A_1G_1A_2G_2A_3G_3A_4G_4A_5G_5$L;
L(AG)$_n$AL, such as L$A_1G_1A_2G_2A_3G_3A_4G_4A_5G_5A_6$L;
L(GA)$_n$L, such as L$G_1A_1G_2A_2G_3A_3G_4A_4G_5A_5$L; or
L(GA)$_n$GL, such as L$G_1A_1G_2A_2G_3A_3G_4A_4G_5A_5G_6$L.

It follows that it is not critical whether an alanine-rich or a glycine-rich segment is adjacent to the N-terminal or C-terminal linker segments. It is preferred that n is an integer from 2 to 10, preferably from 2 to 8, also preferably from 4 to 8, more preferred from 4 to 6, i.e. n=4, n=5 or n=6.

In some embodiments, the alanine content of the REP fragment is above 20%, preferably above 25%, more preferably above 30%, and below 50%, preferably below 40%, more preferably below 35%. It is contemplated that a higher alanine content provides a stiffer and/or stronger and/or less extendible fiber.

In certain embodiments, the REP fragment is void of proline residues, i.e. there are no Pro residues in the REP fragment.

Turning now to the segments that constitute the REP fragment, it is emphasized that each segment is individual, i.e. any two A segments, any two G segments or any two L segments of a specific REP fragment may be identical or may not be identical. Thus, it is not a general feature of the spidroin that each type of segment is identical within a specific REP fragment. Rather, the following disclosure provides the skilled person with guidelines how to design individual segments and gather them into a REP fragment, which is a part of a functional spider silk protein useful in a cell scaffold material.

Each individual A segment is an amino acid sequence having from 8 to 18 amino acid residues. It is preferred that each individual A segment contains from 13 to 15 amino acid residues. It is also possible that a majority, or more than two, of the A segments contain from 13 to 15 amino acid residues, and that a minority, such as one or two, of the A segments contain from 8 to 18 amino acid residues, such as 8-12 or 16-18 amino acid residues. A vast majority of these amino acid residues are alanine residues. More specifically, from 0 to 3 of the amino acid residues are not alanine residues, and the remaining amino acid residues are alanine residues. Thus, all amino acid residues in each individual A segment are alanine residues, with no exception or with the exception of one, two or three amino acid residues, which can be any amino acid. It is preferred that the alanine-replacing amino acid(s) is (are) natural amino acids, preferably individually selected from the group of serine, glutamic acid, cysteine and glycine, more preferably serine. Of course, it is possible that one or more of the A segments are all-alanine segments, while the remaining A segments contain 1-3 non-alanine residues, such as serine, glutamic acid, cysteine or glycine.

In an embodiment, each A segment contains 13-15 amino acid residues, including 10-15 alanine residues and 0-3 non-alanine residues as described above. In a more preferred embodiment, each A segment contains 13-15 amino acid residues, including 12-15 alanine residues and 0-1 non-alanine residues as described above.

It is preferred that each individual A segment has at least 80%, preferably at least 90%, more preferably 95%, most preferably 100% identity to an amino acid sequence selected from the group of amino acid residues 7-19, 43-56, 71-83, 107-120, 135-147, 171-183, 198-211, 235-248, 266-279, 294-306, 330-342, 357-370, 394-406, 421-434, 458-470, 489-502, 517-529, 553-566, 581-594, 618-630, 648-661, 676-688, 712-725, 740-752, 776-789, 804-816, 840-853, 868-880, 904-917, 932-945, 969-981, 999-1013, 1028-1042 and 1060-1073 of SEQ ID NO:10. Each sequence of this group corresponds to a segment of the naturally occurring sequence of *Euprosthenops australis* MaSp1 protein, which is deduced from cloning of the corresponding cDNA, see WO2007/078239. Alternatively, each individual A segment has at least 80%, preferably at least 90%, more preferably 95%, most preferably 100% identity to an amino acid sequence selected from the group of amino acid residues 143-152, 174-186, 204-218, 233-247 and 265-278 of SEQ ID NO:3. Each sequence of this group corresponds to a segment of expressed, non-natural spider silk proteins, which proteins have the capacity to form silk fibers under appropriate conditions. Thus, in certain embodiments of the spidroin, each individual A segment is identical to an amino acid sequence selected from the above-mentioned amino acid segments. Without wishing to be bound by any particular theory, it is envisaged that A segments according to the invention form helical structures or beta sheets.

Furthermore, it has been concluded from experimental data that each individual G segment is an amino acid sequence of from 12 to 30 amino acid residues. It is preferred that each individual G segment consists of from 14 to 23 amino acid residues. At least 40% of the amino acid residues of each G segment are glycine residues. Typically the glycine content of each individual G segment is in the range of 40-60%.

It is preferred that each individual G segment has at least 80%, preferably at least 90%, more preferably 95%, most preferably 100% identity to an amino acid sequence selected from the group of amino acid residues 20-42, 57-70, 84-106, 121-134, 148-170, 184-197, 212-234, 249-265, 280-293, 307-329, 343-356, 371-393, 407-420, 435-457, 471-488, 503-516, 530-552, 567-580, 595-617, 631-647, 662-675, 689-711, 726-739, 753-775, 790-803, 817-839, 854-867, 881-903, 918-931, 946-968, 982-998, 1014-1027, 1043-1059 and 1074-1092 of SEQ ID NO:10. Each sequence of this group corresponds to a segment of the naturally occurring sequence of *Euprosthenops australis* MaSp1 protein, which is deduced from cloning of the corresponding cDNA, see WO2007/078239. Alternatively, each individual G segment has at least 80%, preferably at least 90%, more preferably 95%, most preferably 100% identity to an amino acid sequence selected from the group of amino acid residues 153-173, 187-203, 219-232, 248-264 and 279-296 of SEQ ID NO:3. Each sequence of this group corresponds to a segment of expressed, non-natural spider silk proteins, which proteins have the capacity to form silk fibers under appropriate conditions. Thus, in certain embodiments of the spidroin in the cell scaffold material, each individual G segment is identical to an amino acid sequence selected from the above-mentioned amino acid segments.

In certain embodiments, the first two amino acid residues of each G segment are not -Gln-Gln-.

There are the three subtypes of the G segment. This classification is based upon careful analysis of the *Euprosthenops australis* MaSp1 protein sequence (see WO2007/078239), and the information has been employed and verified in the construction of novel, non-natural spider silk proteins.

The first subtype of the G segment is represented by the amino acid one letter consensus sequence GQG(G/S)QGG(Q/Y)GG (L/Q)GQGGYGQGA GSS (SEQ ID NO:11). This first, and generally the longest, G segment subtype typically contains 23 amino acid residues, but may contain as little as 17 amino acid residues, and lacks charged residues or contain one charged residue. Thus, it is preferred that this first G segment subtype contains 17-23 amino acid residues, but it is contemplated that it may contain as few as 12 or as many as 30 amino acid residues. Without wishing to be bound by any particular theory, it is envisaged that this subtype forms coil structures or $3_1$-helix structures. Representative G segments of this first subtype are amino acid residues 20-42, 84-106, 148-170, 212-234, 307-329, 371-393, 435-457, 530-552, 595-617, 689-711, 753-775, 817-839, 881-903, 946-968, 1043-1059 and 1074-1092 of SEQ ID NO:10. In certain embodiments, the first two amino acid residues of each G segment of this first subtype according to the invention are not -Gln-Gln-.

The second subtype of the G segment is represented by the amino acid one letter consensus sequence GQGGQGQG(G/R)Y GQG(A/S)G(S/G)S (SEQ ID NO:12). This second, generally mid-sized, G segment subtype typically contains 17 amino acid residues and lacks charged residues or contain one charged residue. It is preferred that this second G segment subtype contains 14-20 amino acid residues, but it is contemplated that it may contain as few as 12 or as many as 30 amino acid residues. Without wishing to be bound by any particular theory, it is envisaged that this subtype forms coil structures. Representative G segments of this second subtype are amino acid residues 249-265, 471-488, 631-647 and 982-998 of SEQ ID NO:10; and amino acid residues 187-203 of SEQ ID NO:3.

The third subtype of the G segment is represented by the amino acid one letter consensus sequence G(R/Q)GQG(G/R)YGQG (A/S/V)GGN (SEQ ID NO:13). This third G segment subtype typically contains 14 amino acid residues, and is generally the shortest of the G segment subtypes. It is preferred that this third G segment subtype contains 12-17 amino acid residues, but it is contemplated that it may contain as many as 23 amino acid residues. Without wishing to be bound by any particular theory, it is envisaged that this subtype forms turn structures. Representative G segments of this third subtype are amino acid residues 57-70, 121-134, 184-197, 280-293, 343-356, 407-420, 503-516, 567-580, 662-675, 726-739, 790-803, 854-867, 918-931, 1014-1027 of SEQ ID NO:10; and amino acid residues 219-232 of SEQ ID NO:3.

Thus, in preferred embodiments of the spidroin in the cell scaffold material, each individual G segment has at least 80%, preferably 90%, more preferably 95%, identity to an amino acid sequence selected from SEQ ID NO:11, SEQ ID NO:12 and SEQ ID NO:13.

In an embodiment of the alternating sequence of A and G segments of the REP fragment, every second G segment is of the first subtype, while the remaining G segments are of the third subtype, e.g. . . . $A_1G_{short}A_2G_{long}A_3G_{short}A_4G_{long}A_5G_{short}$ . . . . In another embodiment of the REP fragment, one G segment of the second subtype interrupts the G segment regularity via an insertion, e.g. . . . $A_1G_{short}A_2G_{long}A_3G_{short}A_4G_{short}A_5G_{long}$ . . . .

Each individual L segment represents an optional linker amino acid sequence, which may contain from 0 to 20 amino acid residues, such as from 0 to 10 amino acid residues. While this segment is optional and not critical for the function of the spider silk protein, its presence still allows for fully functional spider silk proteins and polymers thereof which form fibers, films, foams and other structures. There are also linker amino acid sequences present in the repetitive part (SEQ ID NO:10) of the deduced amino acid sequence of the MaSp1 protein from *Euprosthenops australis*. In particular, the amino acid sequence of a linker segment may resemble any of the described A or G segments, but usually not sufficiently to meet their criteria as defined herein.

As shown in WO2007/078239, a linker segment arranged at the C-terminal part of the REP fragment can be represented by the amino acid one letter consensus sequences ASASAAASAA STVANSVS and ASAASAAA, which are rich in alanine. In fact, the second sequence can be considered to be an A segment according to the definition herein, whereas the first sequence has a high degree of similarity to A segments according to this definition. Another example of a linker segment has the one letter amino acid sequence GSAMGQGS, which is rich in glycine and has a high degree of similarity to G segments according to the definition herein. Another example of a linker segment is SASAG.

Representative L segments are amino acid residues 1-6 and 1093-1110 of SEQ ID NO:10; and amino acid residues 138-142 of SEQ ID NO:3, but the skilled person will readily recognize that there are many suitable alternative amino acid sequences for these segments. In one embodiment of the REP fragment, one of the L segments contains 0 amino acids, i.e. one of the L segments is void. In another embodiment of the REP fragment, both L segments contain 0 amino acids, i.e. both L segments are void. Thus, these embodiments of the REP fragments according to the invention may be schematically represented as follows: $(AG)_nL$, $(AG)_nAL$, $(GA)_nL$, $(GA)_nGL$; $L(AG)_n$, $L(AG)_nA$, $L(GA)_n$, $L(GA)_nG$; and $(AG)_n$, $(AG)_nA$, $(GA)_n$, $(GA)_nG$. Any of these REP fragments are suitable for use with any CT fragment as defined below.

The CT fragment of the spidroin in the cell scaffold material has a high degree of similarity to the C-terminal amino acid sequence of spider silk proteins. As shown in WO2007/078239, this amino acid sequence is well conserved among various species and spider silk proteins, including MaSp1 and MaSp2. A consensus sequence of the C-terminal regions of MaSp1 and MaSp2 is provided as SEQ ID NO:9. In FIG. 2, the following MaSp proteins are aligned, denoted with GenBank accession entries where applicable:

TABLE 2

Spidroin CT fragments

| Species and spidroin | Entry |
|---|---|
| *Euprosthenops* sp MaSp1 (Pouchkina-Stantcheva, N N & McQueen-Mason, S J, ibid) | Cthyb_Esp |
| *Euprosthenops australis* MaSp1 | CTnat_Eau |
| *Argiope trifasciata* MaSp1 | AF350266_At1 |
| *Cyrtophora moluccensis* Sp1 | AY666062_Cm1 |
| *Latrodectus geometricus* MaSp1 | AF350273_Lg1 |
| *Latrodectus hesperus* MaSp1 | AY953074_Lh1 |
| *Macrothele holsti* Sp1 | AY666068_Mh1 |
| *Nephila clavipes* MaSp1 | U20329_Nc1 |
| *Nephila pilipes* MaSp1 | AY666076_Np1 |
| *Nephila madagascariensis* MaSp1 | AF350277_Nm1 |
| *Nephila senegalensis* MaSp1 | AF350279_Ns1 |
| *Octonoba varians* Sp1 | AY666057_Ov1 |
| *Psechrus sinensis* Sp1 | AY666064_Ps1 |
| *Tetragnatha kauaiensis* MaSp1 | AF350285_Tk1 |
| *Tetragnatha versicolor* MaSp1 | AF350286_Tv1 |
| *Araneus bicentenarius* Sp2 | ABU20328_Ab2 |
| *Argiope amoena* MaSp2 | AY365016_Aam2 |
| *Argiope aurantia* MaSp2 | AF350263_Aau2 |
| *Argiope trifasciata* MaSp2 | AF350267_At2 |
| *Gasteracantha mammosa* MaSp2 | AF350272_Gm2 |
| *Latrodectus geometricus* MaSp2 | AF350275_Lg2 |
| *Latrodectus hesperus* MaSp2 | AY953075_Lh2 |
| *Nephila clavipes* MaSp2 | AY654293_Nc2 |
| *Nephila madagascariensis* MaSp2 | AF350278_Nm2 |
| *Nephila senegalensis* MaSp2 | AF350280_Ns2 |
| *Dolomedes tenebrosus* Fb1 | AF350269_DtFb1 |
| *Dolomedes tenebrosus* Fb2 | AF350270_DtFb2 |
| *Araneus diadematus* ADF-1 | U47853_ADF1 |
| *Araneus diadematus* ADF-2 | U47854_ADF2 |
| *Araneus diadematus* ADF-3 | U47855_ADF3 |
| *Araneus diadematus* ADF-4 | U47856_ADF4 |

It is not critical which specific CT fragment is present in the spider silk protein in the cell scaffold material. Thus, the CT fragment can be selected from any of the amino acid sequences shown in FIG. 2 and Table 2 or sequences with a high degree of similarity. A wide variety of C-terminal sequences can be used in the spider silk protein.

The sequence of the CT fragment has at least 50% identity, preferably at least 60%, more preferably at least 65% identity, or even at least 70% identity, to the consensus amino acid sequence SEQ ID NO:9, which is based on the amino acid sequences of FIG. 2.

A representative CT fragment is the *Euprosthenops australis* sequence SEQ ID NO:7. Thus, in one embodiment, the CT fragment has at least 80%, preferably at least 90%, such as at least 95%, identity to SEQ ID NO:7 or any individual amino acid sequence of FIG. 2 and Table 2. For example, the CT fragment may be identical to SEQ ID NO:7 or any individual amino acid sequence of FIG. 2 and Table 2.

The CT fragment typically consists of from 70 to 120 amino acid residues. It is preferred that the CT fragment contains at least 70, or more than 80, preferably more than 90, amino acid residues. It is also preferred that the CT fragment contains at most 120, or less than 110 amino acid residues. A typical CT fragment contains approximately 100 amino acid residues.

The term "% identity", as used herein, is calculated as follows. The query sequence is aligned to the target sequence using the CLUSTAL W algorithm (Thompson et al, Nucleic Acids Research, 22:4673-4680 (1994)). A comparison is made over the window corresponding to the shortest of the aligned sequences. The amino acid residues at each position are compared, and the percentage of positions in the query sequence that have identical correspondences in the target sequence is reported as % identity.

The term "% similarity", as used herein, is calculated as described above for "% identity", with the exception that the hydrophobic residues Ala, Val, Phe, Pro, Leu, Ile, Trp, Met and Cys are similar; the basic residues Lys, Arg and His are similar; the acidic residues Glu and Asp are similar; and the hydrophilic, uncharged residues Gln, Asn, Ser, Thr and Tyr are similar. The remaining natural amino acid Gly is not similar to any other amino acid in this context.

Throughout this description, alternative embodiments according to the invention fulfill, instead of the specified percentage of identity, the corresponding percentage of similarity. Other alternative embodiments fulfill the specified percentage of identity as well as another, higher percentage of similarity, selected from the group of preferred percentages of identity for each sequence. For example, a sequence may be 70% similar to another sequence; or it may be 70% identical to another sequence; or it may be 70% identical and 90% similar to another sequence.

In some more specific embodiments of the methods or combination disclosed herein, the spider silk protein of the cell scaffold material comprises a spidroin selected from the group consisting of 4RepCT, RGD-4RepCT, RGE-4RepCT, IKVAV-4RepCT, YIGSR-4RepCT, NT4RepCTHis, 5RepCT, 8RepCT, 4RepCTMa2, NT8RepCT and NTNT8RepCT (see list of appended sequences below). In an even more specific embodiment, the spidroin is 4RepCT (SEQ ID NO:2)

List of Appended Sequences

| SEQ ID NO: | |
|---|---|
| 1 | 4Rep |
| 2 | 4RepCT |
| 3 | NT4Rep |
| 4 | NT5Rep |
| 5 | NT4RepCTHis |
| 6 | NT |
| 7 | CT |
| 8 | consensus NT sequence |
| 9 | consensus CT sequence |
| 10 | repetitive sequence from *Euprosthenops australis* MaSp1 |
| 11 | consensus G segment sequence 1 |
| 12 | consensus G segment sequence 2 |
| 13 | consensus G segment sequence 3 |
| 14 | 5RepCT |
| 15 | 8RepCT |
| 16 | 4RepCTMa2 |
| 17 | NT8RepCT |
| 18 | NTNT8RepCT |
| 19 | RGD-4RepCT |
| 20 | RGE-4RepCT |
| 21 | IKVAV-4RepCT |
| 22 | YIGSR-4RepCT |

In one embodiment of the methods or combination as disclosed herein, said spider silk protein comprises a cell-binding motif. In connection with the cultivation of certain cells in certain situations, the presence of a cell-binding motif has been observed to improve or maintain cell viability, and the inclusion of such a motif into the cell scaffold material as a part of the spider silk protein is thought to provide additional benefits.

In some embodiments, the cell-binding motif is an oligopeptide coupled to the rest of the spider silk protein via at least one peptide bond. For example, it may be coupled to the N-terminal or the C-terminal of the rest of the spider silk protein, or at any position within the amino acid sequence of the rest of the spider silk protein. With regard to the selection of oligopeptidic cell-binding motifs, the skilled person is aware of several alternatives. Said oligopeptide may for example comprise an amino acid sequence selected from the group consisting of RGD, RGE, IKVAV (SEQ ID NO:23), YIGSR (SEQ ID NO:24), EPDIM (SEQ ID NO:25) and NKDIL (SEQ ID NO:26). RGD, IKVAV and YIGSR are general cell-binding motifs, whereas EPDIM and NKDIL are known as keratinocyte-specific motifs that may be particularly useful in the context of cultivation of keratinocytes. The coupling of an oligopeptide cell-binding motif to the rest of the spider silk protein is readily accomplished by the skilled person using standard genetic engineering or chemical coupling techniques. Thus, in some embodiments, the cell-binding motif is introduced via genetic engineering, i.e. forming part of a genetic fusion between nucleic acid encoding the "wild-type" spider silk protein and the cell-binding motif. As an additional beneficial characteristic of such embodiments, the cell-binding motif will be present in a 1:1 ratio to the monomers of spider silk protein in the polymer making up the cell scaffold material.

The polymer in the cell scaffold material used in the methods or combination described herein may adopt a variety of physical forms, and use of a specific physical form may offer additional advantages in different specific situations. For example, in an embodiment of the methods or combination, said cell scaffold material is in a physical form selected from the group consisting of film, foam, fiber and fiber-mesh.

In the context of the present invention, the terms "cultivation" of cells, "cell culture" etc are to be interpreted broadly, such that they encompass for example situations in which cells divide and/or proliferate, situations in which cells are maintained in a differentiated state with retention of at least one functional characteristic exhibited by the cell type when present in its natural environment, and situations in which stem cells are maintained in an undifferentiated state.

Furthermore, as is evident from the above disclosure, it is contemplated that cells may be provided in the form of single cells, or as part of a cellular structure or "micro-organ". Cultivation of cells in the form of a cellular structure or "micro-organ" may entail maintenance of the entire structure in combination with the cell scaffold material.

ITEMIZED LISTING OF EMBODIMENTS

1. Method for the cultivation of eukaryotic cells, comprising providing a sample of eukaryotic cells to be cultured;
applying said sample to a cell scaffold material; and
maintaining said cell scaffold material having cells applied thereto under conditions suitable for cell culture;

characterized in that said cell scaffold material comprises a polymer of a spider silk protein consisting of from 140 to 600 amino acid residues and comprising a repetitive fragment of from 70 to 300 amino acid residues derived from the repetitive fragment of a spider silk protein;

a C-terminal fragment of from 70 to 120 amino acid residues derived from the C-terminal fragment of a spider silk protein; and optionally an N-terminal fragment of from 100 to 160 amino acid residues derived from the N-terminal fragment of a spider silk protein.

2. Method for the preparation of eukaryotic cells, comprising:
providing a sample of eukaryotic cells;
applying said sample to a cell scaffold material;
maintaining said cell scaffold material having cells applied thereto under conditions suitable for cell culture; and
preparing a sample of cells from said cell scaffold material;
characterized in that
said cell scaffold material comprises a polymer of a spider silk protein consisting of from 140 to 600 amino acid residues and comprising
a repetitive fragment of from 70 to 300 amino acid residues derived from the repetitive fragment of a spider silk protein;
a C-terminal fragment of from 70 to 120 amino acid residues derived from the C-terminal fragment of a spider silk protein; and optionally
an N-terminal fragment of from 100 to 160 amino acid residues derived from the N-terminal fragment of a spider silk protein.

3. Method according to item 1 or 2, wherein said conditions comprise maintaining the cell scaffold material having cells applied thereto in a serum-free medium.

4. Method according to any preceding item, wherein said eukaryotic cells are mammalian cells.

5. Method according to item 4, wherein said mammalian cells are derived from organ main tissue.

6. Method according to item 4 or 5, wherein said mammalian cells are selected from the group consisting of stem cells and cells from islets of Langerhans including beta cells.

7. Method according to item 6, wherein said cells are stem cells selected from embryonic stem cells, adult stem cells, induced pluripotent stem cells, amniotic stem cells and progenitor cells, in particular selected from embryonic stem cells, adult stem cells and induced pluripotent stem cells.

8. Method according to item 7, wherein said cells are embryonic stem cells.

9. Method according to item 7, wherein said cells are progenitor cells selected from the group consisting of neural progenitor cells, mesenchymal progenitor cells and hematopoietic progenitor cells.

10. Method according to item 7, wherein said cells are adult stem cells selected from the group consisting of hematopoietic, neural, mesenchymal, mammary, endothelial, epithelial and olfactory stem cells, in particular selected from the group consisting of hematopoietic, neural and mesenchymal stem cells.

11. Method according to item 6, wherein said cells are cells from islets of Langerhans, for example beta cells.

12. Method according to any preceding item, wherein said eukaryotic cells are provided as single cells.

13. Method according to item 10, wherein said mammalian cells are neural stem cells provided as at least one neurosphere.

14. Method according to item 11, wherein said mammalian cells are beta cells provided as at least one islet of Langerhans.

15. Method according to any one of items 1-5, wherein said mammalian cells are somatic cells, for example selected from the group consisting of hepatocytes, fibroblasts, keratinocytes and endothelial cells.

16. Method according to any preceding item, wherein said cells are human cells.

17. Method according to any preceding item, wherein said spider silk protein is selected from the group of proteins defined by the formulas REP-CT and NT-REP-CT, wherein NT is a protein fragment having from 100 to 160 amino acid residues, which fragment is a N-terminal fragment derived from a spider silk protein;
REP is a protein fragment having from 70 to 300 amino acid residues, wherein said fragment is selected from the group consisting of $L(AG)_nL$, $L(AG)_nAL$, $L(GA)_nL$, and $L(GA)_nGL$, wherein
n is an integer from 2 to 10;
each individual A segment is an amino acid sequence of from 8 to 18 amino acid residues, wherein from 0 to 3 of the amino acid residues are not Ala, and the remaining amino acid residues are Ala;
each individual G segment is an amino acid sequence of from 12 to 30 amino acid residues, wherein at least 40% of the amino acid residues are Gly; and
each individual L segment is a linker amino acid sequence of from 0 to 20 amino acid residues; and
CT is a protein fragment having from 70 to 120 amino acid residues, which fragment is a C-terminal fragment derived from a spider silk protein.

18. Method according to item 17, wherein said spider silk protein is selected from the group consisting of 4RepCT, NT4RepCTHis, 5RepCT, 8RepCT, 4RepCTMa2, NT8RepCT and NTNT8RepCT.

19. Method according to any preceding item, wherein said spider silk protein comprises a cell-binding motif.

20. Method according to item 19, wherein said cell-binding motif is an oligopeptide coupled to the remainder of the spider silk protein via at least one peptide bond.

21. Method according to item 20, wherein said oligopeptide is coupled to the N-terminal of the remainder of the spider silk protein.

22. Method according to any one of items 20-21, wherein said oligopeptide comprises an amino acid sequence selected from the group consisting of RGD, RGE, IKVAV, YIGSR, EPDIM and NKDIL.

23. Method according to any preceding item, wherein said cell scaffold material is in a physical form selected from the group consisting of film, foam, fiber and fiber-mesh.

24. Combination of
eukaryotic cells; and
a cell scaffold material;
characterized in that
said cell scaffold material comprises a polymer of a spider silk protein consisting of from 140 to 600 amino acid residues and comprising
a repetitive fragment of from 70 to 300 amino acid residues derived from the repetitive fragment of a spider silk protein;
a C-terminal fragment of from 70 to 120 amino acid residues derived from the C-terminal fragment of a spider silk protein; and optionally
an N-terminal fragment of from 100 to 160 amino acid residues derived from the N-terminal fragment of a spider silk protein.

25. Combination according item 24, wherein said eukaryotic cells are mammalian cells.

26. Combination according to item 25, wherein said mammalian cells are derived from organ main tissue.

27. Combination according to item 25 or 26, wherein said mammalian cells are selected from the group consisting of stem cells and cells from islets of Langerhans including beta cells.

28. Combination according to item 27, wherein said cells are stem cells selected from embryonic stem cells, adult stem cells, induced pluripotent stem cells, amniotic stem cells and progenitor cells, in particular selected from embryonic stem cells, adult stem cells and induced pluripotent stem cells.

29. Combination according to item 28, wherein said cells are embryonic stem cells.

30. Combination according to item 28, wherein said cells are progenitor cells selected from the group consisting of neural progenitor cells, mesenchymal progenitor cells and hematopoietic progenitor cells.

31. Combination according to item 28, wherein said cells are adult stem cells selected from the group consisting of hematopoietic, neural, mesenchymal, mammary, endothelial, epithelial and olfactory stem cells, in particular selected from the group consisting of hematopoietic, neural and mesenchymal stem cells.

32. Combination according to item 27, wherein said cells are cells from islets of Langerhans, for example beta cells.

33. Combination according to any preceding item, wherein said eukaryotic cells are provided as single cells.

34. Combination according to item 31, wherein said mammalian cells are neural stem cells provided as at least one neurosphere.

35. Combination according to item 30, wherein said mammalian cells are beta cells provided as at least one islet of Langerhans.

36. Combination according to any one of items 24-26, wherein said mammalian cells are somatic cells, for example selected from the group consisting of hepatocytes, fibroblasts, keratinocytes and endothelial cells.

37. Combination according to any one of items 24-36, wherein said cells are human cells.

38. Combination according to any one of items 24-37, wherein said spider silk protein is selected from the group of proteins defined by the formulas REP-CT and NT-REP-CT, wherein NT is a protein fragment having from 100 to 160 amino acid residues, which fragment is a N-terminal fragment derived from a spider silk protein;

REP is a protein fragment having from 70 to 300 amino acid residues, wherein said fragment is selected from the group consisting of $L(AG)_nL$, $L(AG)_nAL$, $L(GA)_nL$, and $L(GA)_nGL$, wherein n is an integer from 2 to 10;

each individual A segment is an amino acid sequence of from 8 to 18 amino acid residues, wherein from 0 to 3 of the amino acid residues are not Ala, and the remaining amino acid residues are Ala;

each individual G segment is an amino acid sequence of from 12 to 30 amino acid residues, wherein at least 40% of the amino acid residues are Gly; and each individual L segment is a linker amino acid sequence of from 0 to 20 amino acid residues; and CT is a protein fragment having from 70 to 120 amino acid residues, which fragment is a C-terminal fragment derived from a spider silk protein.

39. Combination according to item 38, wherein said spider silk protein is selected from the group consisting of 4RepCT, NT4RepCTHis, 5RepCT, 8RepCT, 4RepCTMa2, NT8RepCT and NTNT8RepCT.

40. Combination according to any one of items 24-39, wherein said spider silk protein comprises a cell-binding motif.

41. Combination according to item 40, wherein said cell-binding motif is an oligopeptide coupled to the remainder of the spider silk protein via at least one peptide bond.

42. Combination according to item 41, wherein said oligopeptide is coupled to the N-terminal of the remainder of the spider silk protein.

43. Combination according to any one of items 41-42, wherein said oligopeptide comprises an amino acid sequence selected from the group consisting of RGD, RGE, IKVAV, YIGSR, EPDIM and NKDIL.

44. Combination according to any one of items 24-43, wherein said cell scaffold material is in a physical form selected from the group consisting of film, foam, fiber and fiber-mesh.

45. Method or combination according to any preceding item, in which said spider silk protein is selected from the group consisting of 4RepCT, NT4RepCTHis, RGD-4RepCT, RGE-4RepCT, IKVAV-4RepCT and YIGSR-4RepCT.

BRIEF DESCRIPTION OF THE DRAWINGS

FIG. 1 shows a sequence alignment of spidroin N-terminal domains.

Figure 2:
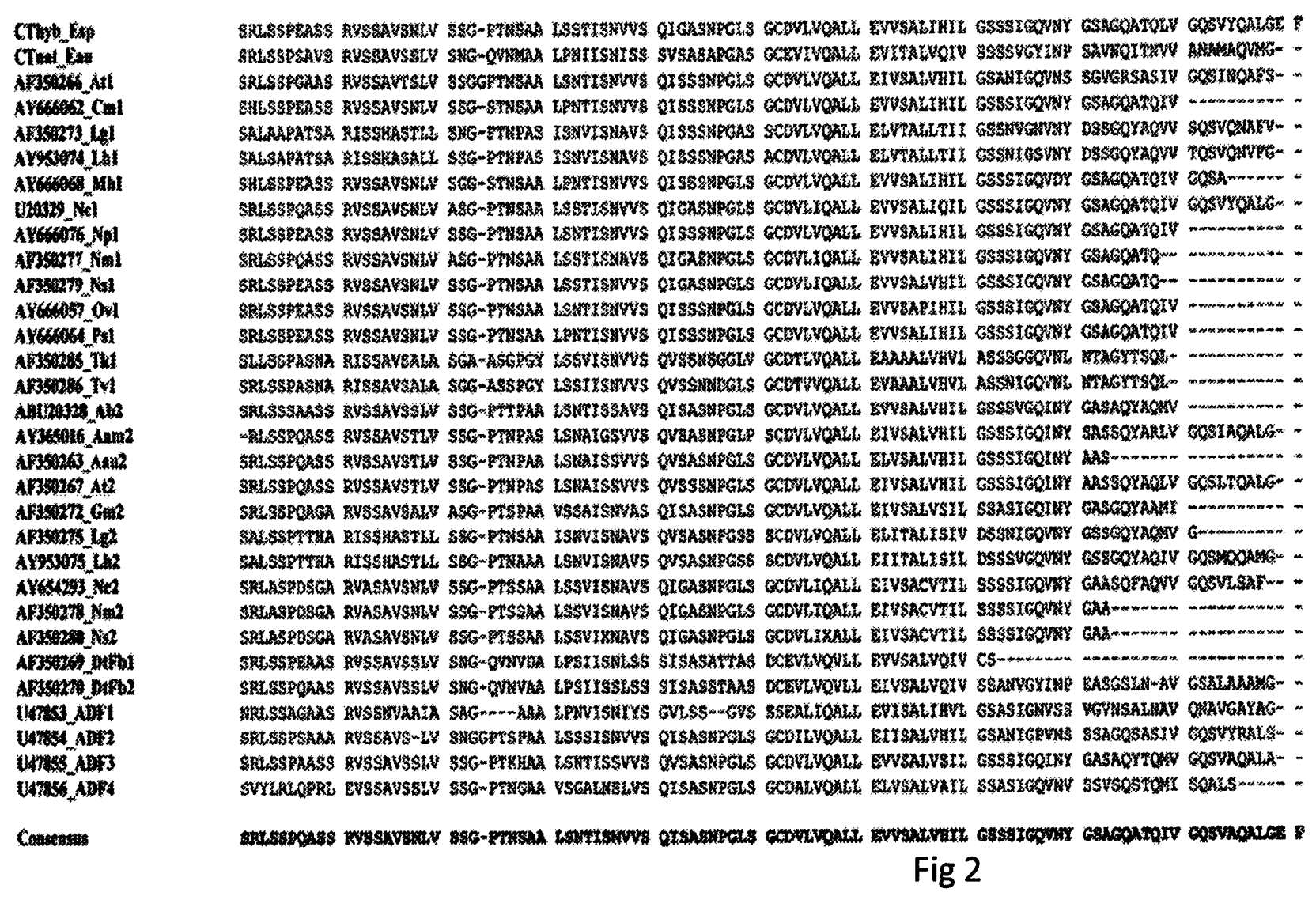

FIG. 2 shows a sequence alignment of spidroin C-terminal domains.

FIG. 8 is a pair of photographs at A) 4× and B) 10× magnification of the RCM-1 hESC cells prior to the experiments described in Example 2.

FIG. 9 is a pair of photographs at 10× magnification showing RCM-1 hESC cultures after culturing for 48 hours on A) CELLstart™ CTS™ and B) RGD-4RepCT.

FIG. 11 is a pair of photographs at 10× magnification showing the result of alkaline phosphatase staining of RCM-1 hESC cultures on A) CELLstart™ CTS™, and B) RGD-4RepCT as described in Example 2.

FIG. 17 shows Live/Dead staining of NSCs growing on 4RepCT film on the left (at 72 h post seeding) and PORN on the right (at 48 h post seeding). Each column of pictures represents the same area, showing live and dead cells respectively.

FIG. 22 is a series of diagrams showing insulin release upon glucose stimulation of islets cultured for 5 days in wells with 4RepCT without (WT) and with different peptide motifs as indicated; A: Insulin release from all mouse islets cultured with 4RepCT without (WT) and with different peptide motifs as indicated, for 5 days; B: Stimulation index of mouse islets cultured with 4RepCT without (WT) and with different peptide motifs for 5 days; C: Insulin release from adhered mouse islets cultured with 4RepCT without (WT) and with different peptide motifs for 5 days (n=2, experiments done in duplicate); D: Insulin release from adhered mouse islets cultured with NT4RepCT scaffolds (NT) for 2 days; E: Insulin release from all human islets cultured with 4RepCT without (WT) and with different peptide motifs for 5 days; F: Insulin release from adhered human islets cultured with 4RepCT without (WT) and with different peptide motifs for 5 days (n=1, experiments done in triplicates).

FIG. 29 is a pair of photographs at the indicated magnification, showing adherence and growth of mesenchymal stem cells (MSC) on foam scaffolds 4RepCT (WT) and RGD-4RepCT (RGD) as indicated. MSC (gray) could readily adhere to the foam structure (light gray, exemplified by arrow) and continued to proliferate over time thereon (day 7, n=2).

FIGS. 39A-D show the production of collagen type I by cells growing on different 4RepCT scaffolds as indicated. A is a diagram showing the concentration of C peptide in the cell culture medium secreted during the first 5 days of culture (not accumulated). B is a diagram showing the amount of C-peptide secreted/cell growing on the different scaffolds during the same culture period. C-peptide concentration was determined by EIA. Error bars show standard deviation of duplicates. C and D are photographs showing intracellular collagen type I (appears as white dots) present in cells growing on film (C) and fiber-mesh (D), stained with immunofluorescence. Nuclei appear as light grey.

FIGS. 41A-C are diagrams showing the number of live HDFn growing on 4RepCT scaffolds of fiber-mesh (A) and film (B-C) with or without the integrin binding motif RGD as indicated. Assayed with Alamar blue. Error bars show standard deviation of hexaplicates.

FIG. 48 is a pair of photographs showing the appearance of hESC grown on RGD-4RepCT film (RGD) for 16 days (left) and hESCs grown on control coating (Cellstart) for 192 hours (right). The cells are in the first passage of the experiment described in Example 12.

FIG. 49 is a pair of photographs showing the appearance of hESC 24 hours post seeding in the second passage of the experiment described in Example 12 on respective coating. Left: Cellstart coating (control); Right: RGD-4RepCT film (RGD).

FIG. 51 is a pair of photographs showing the appearance of AP-stained hESC 24 hours post seeding in the third passage of the experiment described in Example 12 on respective coating. Left: cells grown on RGD-4repCT film (RGD); Right: cells grown on RGE-4RepCT film (RGE). Positive AP staining appears in brown color (dark grey in picture).

FIG. 52 is a pair of photographs showing the appearance of AP-stained hESC 24 hours post seeding in the third passage of the experiment described in Example 12 on respective coating. Left: cells grown on IKVAV-4repCT film (IKVAV); Right: cells grown on NT4RepCTHis film (NRC). Positive AP staining appears in brown color (dark grey in picture).

EXAMPLES

Example 1

Figure 3:
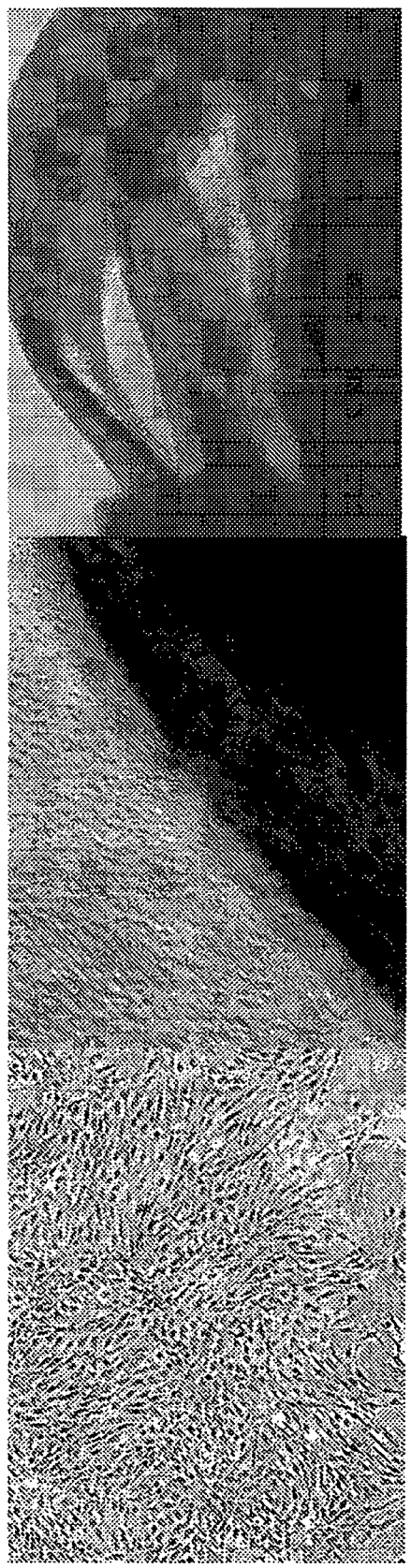
FIG. 3 is a series of photographs showing murine mesenchymal stem cells cultured on 4RepCT fibers.

Hematopoietic and Mesenchymal Stem Cells on Recombinant Spider Silk

Hematopoietic stem cells (HSC), which are known to be extremely sensitive to unfavorable influences from their direct microenvironment, and mesenchymal stem cells (MSC), which have been shown to adhere and grow on a variety of biodegradable natural and synthetic scaffolds, were cultured on recombinant spider silk matrices comprising 4RepCT as described above. HSC could be cultured on 4RepCT foam and maintained their ability to differentiate as well as their phenotype when compared to HSC:s cultured on Falcon 1008 plastic and retronectin-coated plates. MSC showed similar cell count and differentiation as compared to controls when grown on 4RepCT fibers, and retained their ability to differentiate into cells of mesodermal lineage, such as bone, cartilage and fatty cells, when grown on 4RepCT films and foams.

Materials and Methods
Expression of Recombinant Spider Silk Proteins

The recombinant spider silk protein 4RepCT (SEQ ID NO:2) was produced as previously described (Hedhammar et al (2008), supra). Briefly, *Escherichia coli* BL21(DE3) cells (Merck Biosciences) with the vector for 4RepCT expression were grown at 30° C. in Luria-Bertani medium containing kanamycin to an OD$_{600}$ of 0.8-1 and then induced with isopropyl 13-D-thiogalactopyranoside and further incubated for up to 3 h at room temperature. Thereafter, cells were harvested and resuspended in 20 mM Tris-HCl (pH 8.0) supplemented with lysozyme and DNaseI. After complete lysis, the supernatants from centrifugation at 15,000 g were loaded onto a column packed with Ni SEPHAROSE™ (GE Healthcare, Uppsala, Sweden). The column was washed extensively before elution of bound proteins with 300 mM imidazole. Fractions containing the target proteins were pooled and dialyzed against 20 mM Tris-HCl (pH 8.0). 4RepCT was released from the tags by proteolytic cleavage using a thrombin:fusion protein ratio of 1:1000 (w/w) at room temperature for 1-2 h. To remove the released HisTrxHis tag, the cleavage mixture was loaded onto a second Ni SEPHAROSE™ column and the flowthrough was collected. The protein content was determined from the absorbance at 280 nm.

Scaffold Preparation

Purified 4RepCT proteins were allowed to self-assemble into fibers as described in Stark et al (2007), supra. The fibers were then cut into smaller pieces before being used for culturing in non-tissue culture treated Falcon dishes (Falcon 1008). Films were prepared by coating of Falcon 1008 dishes with 0.5-2.0 ml protein solution and air drying to allow formation of a thin layer at the bottom of the dishes. In addition, some Falcon 1008 dishes were coated with foam, obtained after vigorous mixing of the protein solution, and allowed to air dry for 24 hours to form a 3D matrix on the bottom of the dishes. Dishes with fibers, films or foams were sterilized by exposure to 280 Gy γ-radiation, delivered by a $^{137}$Cs source (Gammacell, Atomic Energy of Canada, Ottawa, Canada).

Hematopoietic Stem Cell Isolation and Culture

Healthy Balb/c mice were killed and femurs removed. Bone marrow (BM) cells were flushed from femora with Hanks' balanced salt solution buffered with 10 mM HEPES buffer (HH; GIBCO). BM cells were either used directly or after lineage depletion with a lineage cell depletion kit (Miltenyi Biotec) according to the manufacturer's instructions and cultured for 4 days, at $3\times10^5$ and $5\times10^4$ cells/dish, respectively, in serum-free DMEM (Wognum et al (2000), Hum Gene Ther 11:2129-2141), supplemented with murine stem cell factor (mSCF, 100 ng/ml; Immunex, Seattle, Wash.) and mIL-3 (30 ng/ml; Genentech, San Francisco, Calif.).

Measurement of Surface Antigens

Murine bone marrow cells, before and after culture in the presence of 4RepCT, were collected for phenotypic analysis. Briefly, cells were washed twice with Hanks' buffered HEPES solution (HHBS) containing 0.5% (vol/vol) bovine serum albumin (BSA; Sigma, St Louis, Mo.), 0.05% (wt/vol) sodium azide, and 0.45% (wt/vol) glucose (Merck, Darmstadt, Germany) (HBN) and resuspended in 50 µl HBN containing 2% (vol/vol) normal, heat-inactivated mouse serum to prevent nonspecific binding of the monoclonal antibodies (MoAbs) and subsequently incubated for 30 minutes with MoAbs raised against the following surface markers: c-kit, sca-1, CD4, CD8, CD11b and B220 (BD Biosciences, San Jose, Calif.). Cells were washed twice in HBN and dead cells were excluded from analysis based on propidium iodine (PI, Sigma) staining. Cell samples were measured using a FACSCalibur flow cytometer, and 10,000 list mode events were collected and analyzed using the Cellquest software (BD Biosciences, San Jose, Calif.).

In Vitro Clonogenic Progenitor Assays $5\times10^4$ murine BM cells or $1\times10^3$ lineage depleted BM cells (lin$^{-/-}$) were plated in Falcon 1008 (35 mm diameter) Petri dishes in 1 ml of serum-free semi-solid methylcellulose culture medium containing 0.8% (wt/vol) methylcellulose (METHOCEL™ A4M Premium grade, Dow Chemical Co, Barendrecht, The Netherlands) in enriched DMEM, 1% (wt/vol) BSA, 0.3 mg/ml human transferrin, 0.1 µmol/l sodium selenite, 1 mg/l nucleosides (cytidine, adenosine, uridine, guanosine, 2'-deoxycytidine, 2'-deoxyadenosine, thymidine and 2'-deoxyguanosine; Sigma), 0.1 mmol/l β-mercaptoethanol, 15 µmol/l linoleic acid, 15 µmol/l cholesterol, 10 µg/ml insulin, 100 U/ml penicillin, and 100 µg/ml streptomycin.

Granulocyte/macrophage colony formation (CFU-GM) was stimulated by addition of 10 ng/ml mIL-3, 100 ng/ml mSCF, and 20 ng/ml GM-CSF and scored at day 8-10 of culture. Burst-forming erythroid (BFU-E) growth was induced by 100 ng/ml mSCF and 4 U/ml human erythropoietin (hEPO; Behringwerke, Marburg, Germany) and counted after 8-10 days, whereas colony-forming unit erythroid (CFU-E) growth was stimulated with hEPO alone and counted after 2 days. Megakaryocyte progenitor cells (CFU-Meg) were stimulated in 0.275% agar cultures supplemented with 100 ng/ml mSCF, 10 ng/ml mIL-3m, and 10 ng/ml mTPO (Genentech, San Francisco, Calif.). Colonies were dried after 10 days and stained for acetyl cholinesterase positive cells, and enumerated.

Mesenchymal Stem Cell Isolation and Culture

Human mesenchymal stem cells (hMSC) were purchased from Lonza (Verviers, Belgium). Cells were cultured in complete medium-1 (CM-1) consisting of 54% DMEM-LG, 36% MCDB-201, 10% FCS, 1 mM L-Glutamin and 1% penicillin/streptomycin (Reyes et al (2001), Blood 98:2615-2625). Cells were trypsinized and subcultured when confluence reached 80-90%, and medium was refreshed every 3-4 days.

Murine mesenchymal stem cells (mMSC) were obtained by flushing the femurs of Balb/c mice with HH. Full BM cells were cultured in the presence of DMEM-LG supplemented with 10% FCS, 1 mM L-Glutamin and 1% penicillin/streptomycin (CM-2). Adherent cells were subcultured and passaged once weekly. Medium was changed every 3-4 days.

Differentiation Assays

For adipogenic differentiation, MSC:s were cultured in the presence of adipogenic medium consisting of DMEM-LG, 10% FCS, 1 µM dexamethasone, 60 µM indomethacine, 500 µM isobutylmethylxanthine (IBMX) and 5 µg/ml insulin (Sigma, St. Louis, USA) for 21 days and stained with Oil Red 0 (Sigma, St Louis, USA). For osteogenic differentiation, MSC:s were maintained for 21 days in osteogenic medium consisting of DMEM-LG, 10% FCS, 100 nM dexamethasone, 10 mM β-glycerophosphate and 0.2 mM ascorbic acid (Sigma, St. Louis, USA). Cells were stained with Alizarin Red S (Sigma, St. Louis, USA) to confirm presence of calcium phosphate deposits. For chondrogenic differentiation, $2.5\times10^5$ cells were spun down in a 15 ml polypropylene tube and the spontaneously formed three-dimensional pellet was cultured for 21 days in chondrogenic medium consisting of DMEM-HG (Gibco) with 100 nM dexamethasone, 10 ng/ml TGFβ3 (Peprotech, USA), 50 µg/ml ascorbic acid, 50 mg/ml ITS+Premix (Becton Dickinson, USA). Sections of the pellet were prepared for histological studies and stained with Alcian Blue for confirmation of chondrocytic lineage.

Results

Stem Cell Expansion and Differentiation in the Presence of 4RepCT Fibers

In three separate experiments, performed in duplicate, the expansion of murine bone marrow cells in presence or absence of small pieces of 4RepCT was investigated. Results are displayed in Table 3, which shows the effect of 4 day culture in the presence of 4RepCT on expansion of murine bone marrow (BM) cells in serum-free medium supplemented with 100 ng/ml mSCF and 30 ng/ml mIL-3. Cells counted were colony forming units-erythrocyte (CFU-E); burst-forming unit-erythrocyte (BFU-E); colony forming unit-granulocyte/macrophage (CFU-GM); and colony forming unit-megakaryocyte (CFU-Meg). No significant differences were found between cell numbers and amount of colonies formed after culture for 4 days in the presence of 4RepCT fibers in comparison to control wells.

TABLE 3

|  | Day 0 BM | Day 4 control BM | S.I. | Day 4 BM-4RepCT | S.I. |
| --- | --- | --- | --- | --- | --- |
| CFU-E[1] | 507.0 ± 98.1 | 2599.7 ± 375.3 | 5.1 | 2296.7 ± 1413.0 | 4.5 |
| BFU-E[1] | 106.7 ± 8.5 | 173.5 ± 61.5 | 1.6 | 282.0 ± 183.8 | 2.6 |
| CFU-GM[1] | 210.3 ± 50.4 | 1935.7 ± 663.4 | 9.2 | 1495.3 ± 187.6 | 7.1 |
| CFU-Meg[1] | 40.3 ± 13.6 | 163.0 ± 17.6 | 4.0 | 91.0 ± 78.9 | 2.3 |
| Cells[2] | 3.0 ± 0.0 | 8.2 ± 3.6 | 2.7 | 5.5 ± 2.6 | 1.8 |

Results are expressed as the average of three separate experiments ± standard deviation. All experiments were done in duplicates.
[1]Colonies per $1\times10^5$ BM cells
[2]Cells $\times 10^5$
S.I.: stimulation index in comparison to day 0 values Murine MSC:s were maintained in culture medium until subconfluence and then trypsinized. $1\times10^5$ mMSC were cultured in 6-well plates in presence or absence of 1 cm pieces of 4RepCT fibers for 7 days and then trypsinized and counted. Control wells showed a 5.7-fold expansion after 7 days, whereas cells cultured in the presence of 4RepCT expanded 4.0-fold. However, only cells remaining in the culture dishes were trypsinized, and cells growing on the fibers were not included in the total cell count, thus leading to an underestimation of the actual number of cells present in each well. To prevent excretion of inhibitory signals due to contact inhibition in dense near-confluent cultures, after 7 days, 14 days and 21 days, the fibers were carefully removed from the culture dishes, rinsed once with PBS and transferred to a fresh well containing culture medium only. Cells arising in these culture dishes were thus all derived from a single source, i.e. the recombinant spider silk threads (FIG. 3).

Figure 4:
FIG. 4 is a series of photographs showing human mesenchymal stem cells cultured on 4RepCT fibers.
Figure 5:
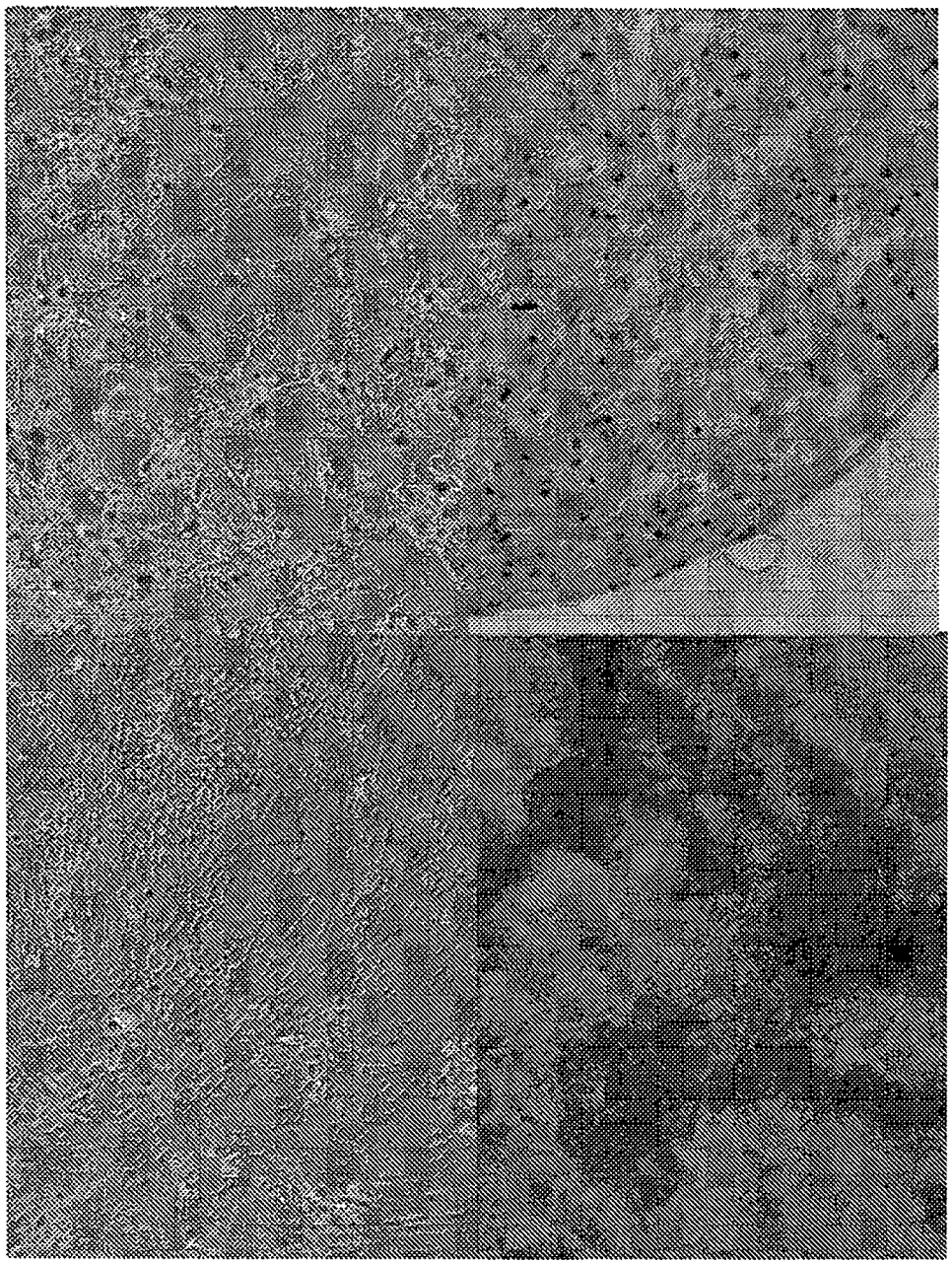
FIG. 5 is a series of photographs showing differentiation of human mesenchymal stem cells cultured on 4RepCT scaffolds.

Human MSC:s were maintained in culture medium under similar conditions as the mMSC:s. Fibers were transferred to fresh culture dishes once weekly (FIG. 4). At day 21 of culture, 4RepCT fibers were removed. The remaining hMSC:s, which covered the surface of the culture wells and were derived from the recombinant spider silk fibers, were trypsinized and tested for their capacity to differentiate into adipogenic, osteogenic and chondrogenic lineage (FIG. 5). All tests were done in triplicate. Cells derived from the 4RepCT fibers displayed a comparable differentiation capacity compared with hMSC:s from the same passage cultured in the absence of 4RepCT.

Expansion and Differentiation on 4RepCT-Coated Tissue Culture Plates

Murine bone marrow cells were lineage depleted ($lin^{-/-}$) and cultured on culture dishes covered with 4RepCT foam in serum-free medium containing mSCF and mIL-3. Expansion of $lin^{-/-}$ BM cells and colony forming unit numbers, after 4 days of culture, were compared with cultures of lineage negative cells cultured on non-tissue culture treated dishes (35 mm, Falcon 1008) and Falcon 1008 dishes coated with recombinant fibronectin fragment CH-296 (Retronectin: RN; Takara Shuzo, Otzu, Japan) at a concentration of 10 µg/cm². Results are shown in Table 4, for the number of in vitro burst-forming unit-erythrocyte (BFU-E); colony forming unit-granulocyte/-macrophage (CFU-GM); and colony forming unit-megakaryocyte (CFU-Meg).

TABLE 4

|  | Day 0 $lin^{-/-}$ | Day 4 $lin^{-/-}$ Falcon 1008 | S.I. | Day 4 $lin^{-/-}$ retronectin | S.I. | Day 4 $lin^{-/-}$ 4RepCT foam | S.I. |
|---|---|---|---|---|---|---|---|
| BFU-E[1] | 340 | 70 | 0.2 | 35 | 0.1 | 0 | 0 |
| CFU-GM[1] | 1385 | 2555 | 1.8 | 1720 | 1.2 | 1310 | 0.9 |
| CFU-Meg[1] | 50 | 10 | 0.2 | 15 | 0.3 | 35 | 0.7 |
| Cells[2] | 4.0 | 57 | 14.3 | 62 | 15.5 | 63 | 15.8 |

Results of one experiment performed in duplicate are shown
[1]Colonies per $1 \times 10^5$ BM cells
[2]Cells $\times 10^5$
S.I.: stimulation index in comparison to day 0 values In addition, expression of cell surface markers was measured before and after culture on differentially coated dishes (Table 5).

TABLE 5

|  | Day 0 $lin^{-/-}$ | Day 4 $lin^{-/-}$ Falcon 1008 | S.I. | Day 4 $lin^{-/-}$ retronectin | S.I. | Day 4 $lin^{-/-}$ 4RepCT foam | S.I. |
|---|---|---|---|---|---|---|---|
| CD4 | 0.1 | 0.5 | 5.0 | 0.6 | 6.0 | 0.8 | 8.0 |
| CD8 | 0.1 | 0.1 | 1.0 | 0.2 | 2.0 | 0.1 | 1.0 |
| CD11b | 0.2 | 8.6 | 43.0 | 12.1 | 60.5 | 20.0 | 100.0 |
| B220 | 0.1 | 0.8 | 8.0 | 0.3 | 3.0 | 0.3 | 3.0 |
| Sca-1 | 0.1 | 25.6 | 256.0 | 20.6 | 206 | 4.5 | 45.0 |
| c-Kit | 0.5 | 1.1 | 2.2 | 1.1 | 2.2 | 1.7 | 3.4 |

Figure 6:
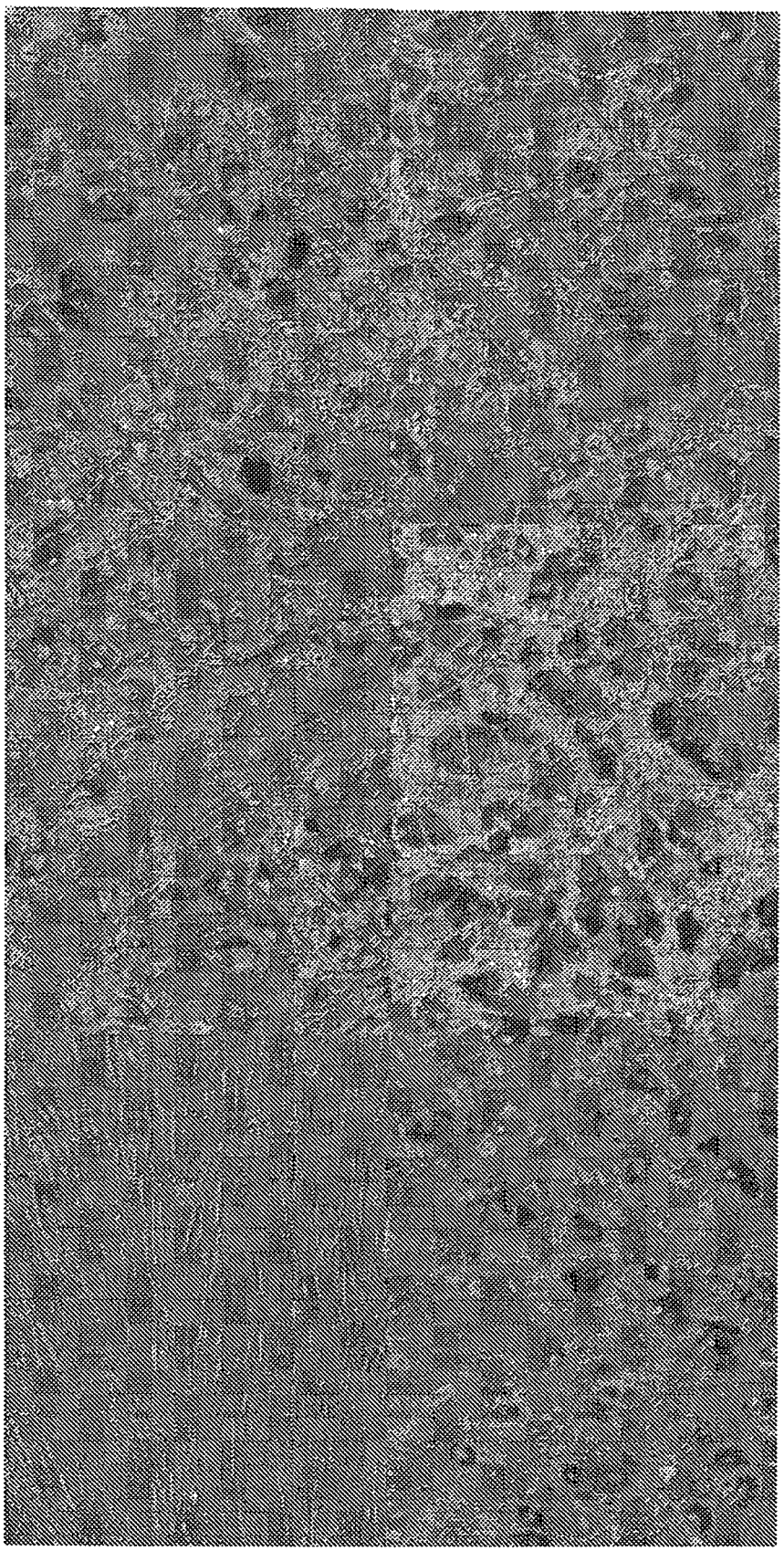
FIG. 6 is a series of photographs showing results of experiments on adipogenic differentiation of human mesenchymal stem cells cultured on 4RepCT scaffolds.
Figure 7A:
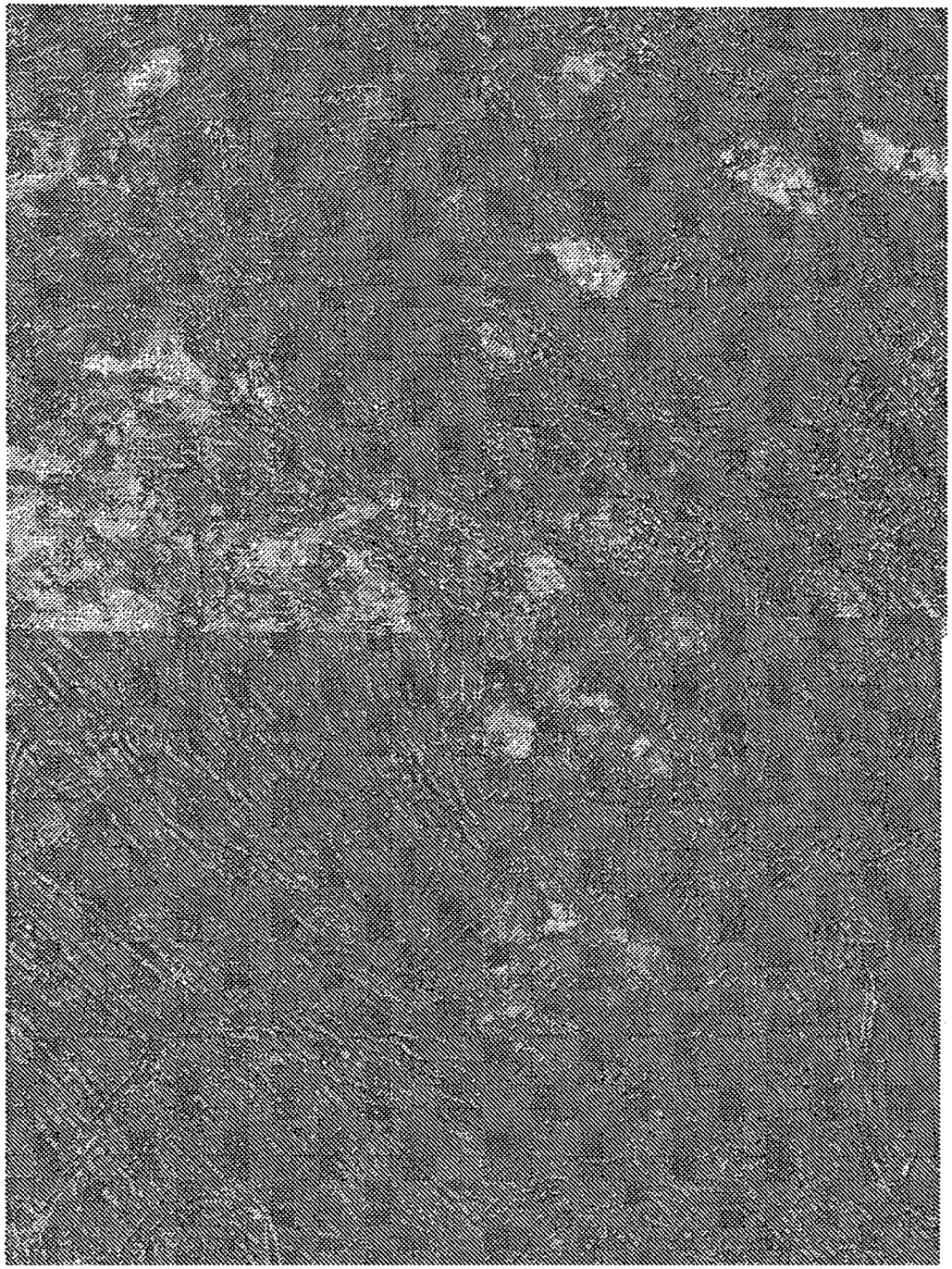
FIGS. 7A-B are series of photographs showing results of experiments on osteogenic differentiation of human mesenchymal stem cells cultured on 4RepCT scaffolds.
Figure 7B:
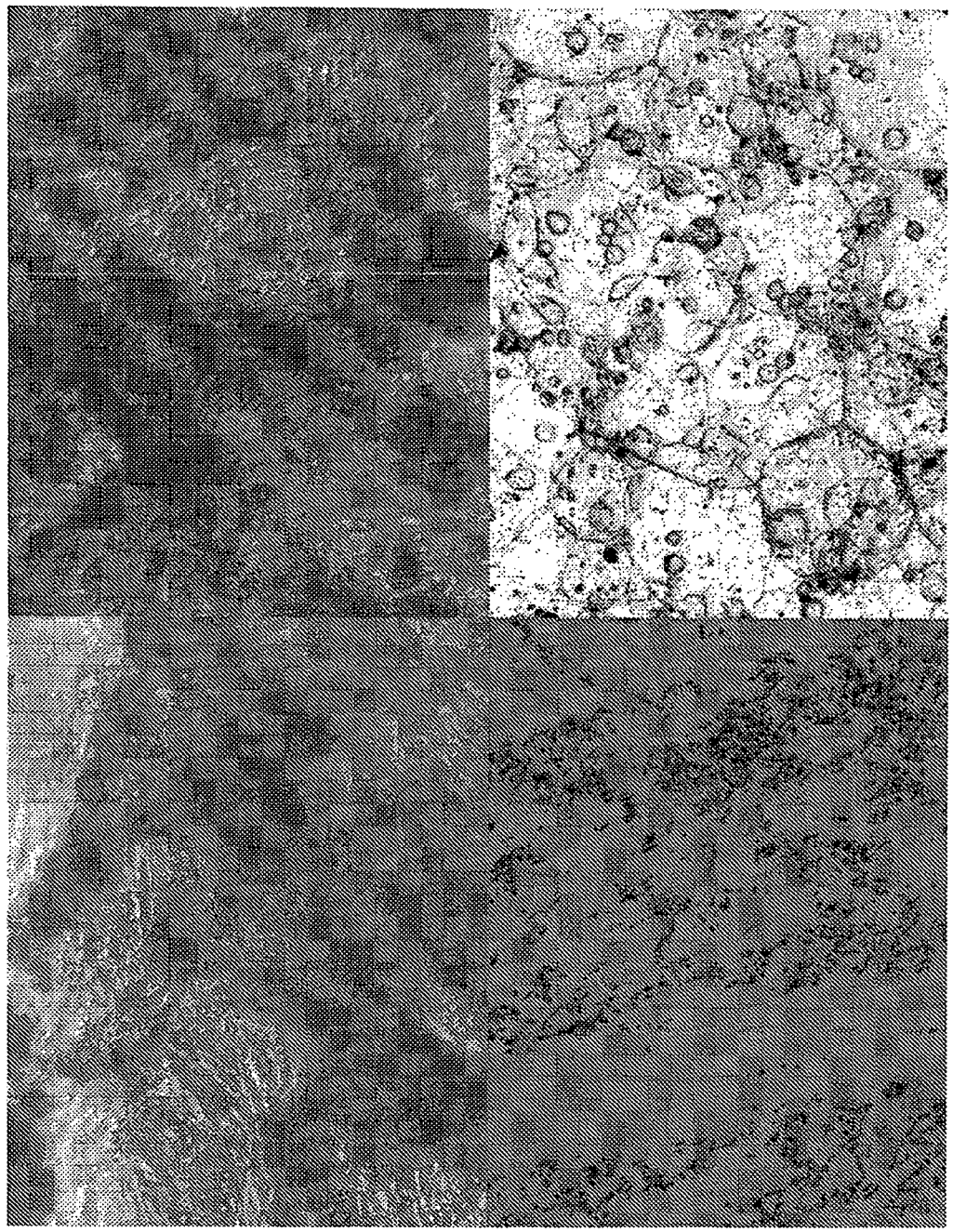
Figure 10:
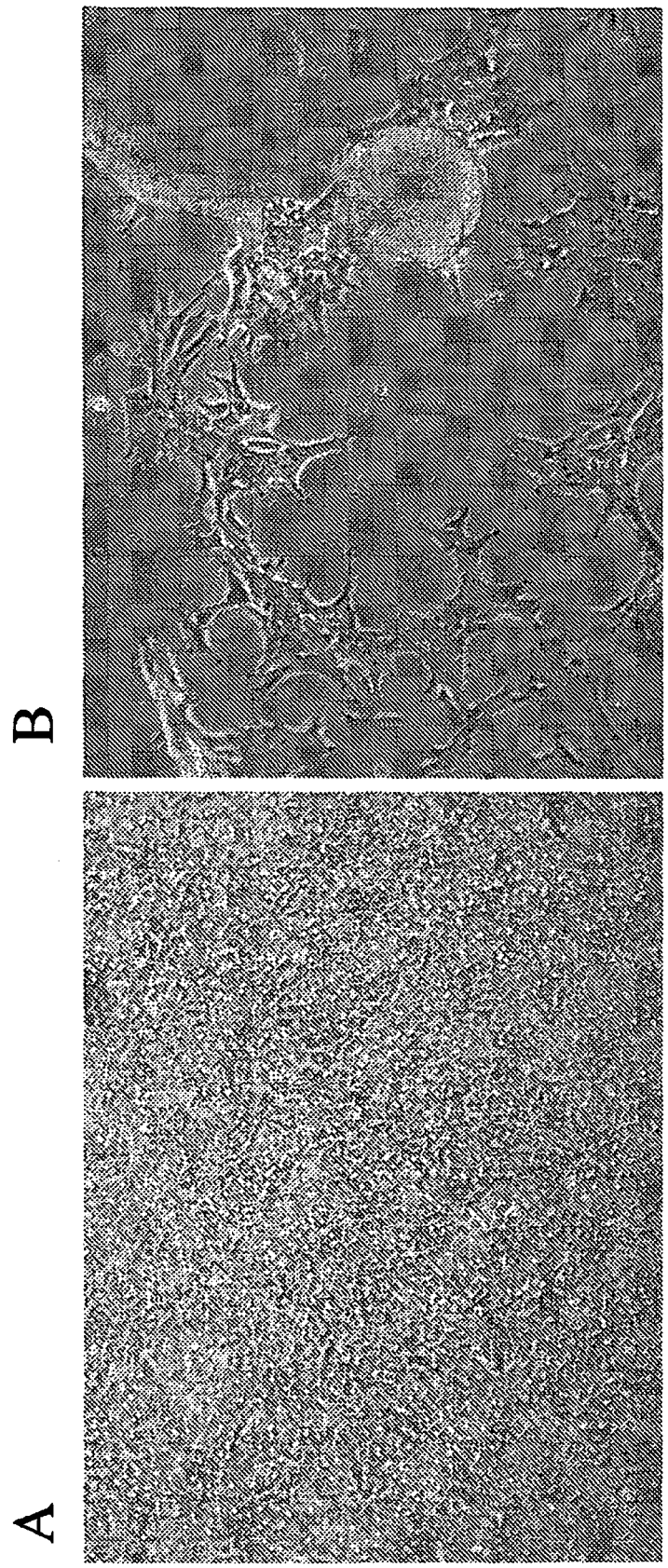
FIG. 10 is a pair of photographs at 10× magnification showing RCM-1 hESC cultures after culturing for 144 hours on A) CELLstart™ CTS™ and B) RGD-4RepCT.
Figure 12:
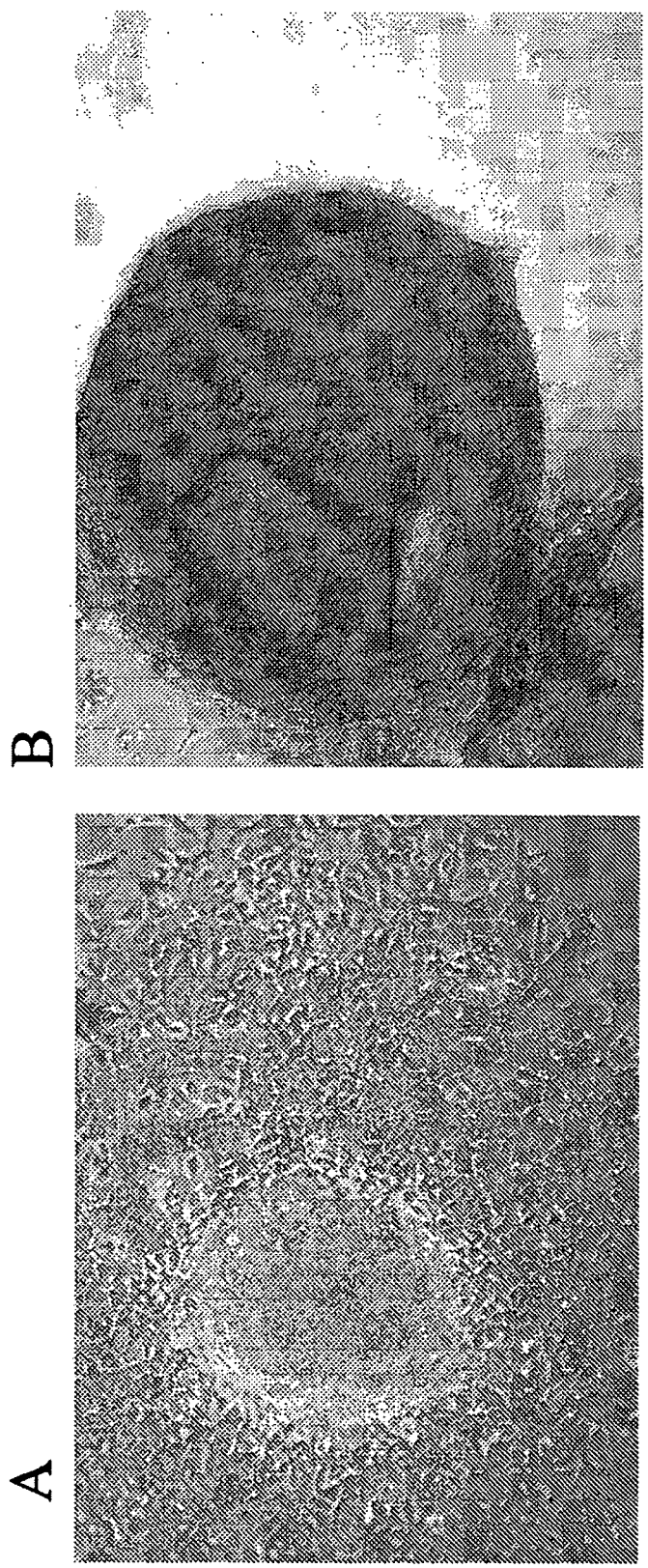
FIG. 12 is a pair of photographs at 10× magnification showing A) RCM-1 hESC after culturing for 240 hours on RGD-4RepCT, and B) alkaline phosphatase staining of RCM-1 hESC after culturing for 240 hours on RGD-4RepCT.

Results of one experiment performed in duplicate are shown. Data are expressed as absolute cell numbers $\times 10^5$.
S.I.: stimulation index in comparison to day 0 values $1\times10^5$ senescent hMSC:s were plated onto non-tissue culture treated dishes (35 mm, Falcon 1008), tissue culture treated dishes (35 mm, Falcon 3001), tissue culture treated 6-well plates (Falcon) and dishes coated with 4RepCT film or foam (35 mm, Falcon 1008), and cultured until almost confluent. Cells were then maintained for 21 days in control medium, adipogenic differentiation medium or osteogenic differentiation medium. Results are displayed in FIGS. 6 and 7 for adipogenic differentiation and osteogenic differentiation, respectively. Cells cultured in the presence of adipogenic medium showed, independently of the coating of the dishes, a similar degree of adipogenic differentiation, having rounded cells containing multiple lipid vesicles divided equally over the surface of the dishes. In contrast, the senescent hMSC:s were no longer able to differentiate into osteogenic lineage despite regular medium changes with osteogenic differentiation medium, when cultured under any of the control conditions (FIG. 7A), but interestingly showed some patchy Alizarin Red S staining in the film and foam coated plates (FIG. 7B, upper left and right, respectively). This staining could not be attributed to staining of the 4RepCT itself, as plates coated with either 4RepCT film or foam, containing no cells, did not show any positive Alizarin Red S areas (FIG. 7B, lower left and right, respectively).

Example 2

Human Embryonic Stem Cells on Recombinant Spider Silk

The experiment shows the feasibility of culturing human embryonic stem cells on a recombinant spider silk material.
Materials and Methods Standard six-well tissue culture plates were prepared. In the plates, three wells contained RGD-4RepCT film and the remaining three wells were empty. The 4RepCT film with the cell-binding motif RGD was prepared essentially as described in Example 1. The tissue culture plates were kept dry at room temperature until further use.

In preparation for the experiment, the tissue culture plates were UV irradiated for 30 minutes in a Class II microbiological safety cabinet. The three empty wells in each plate were then coated with CELLstart™ CTS™ (Invitrogen; cat no A10142-01), as per manufacturer's protocol.

Human embryonic stem cells (RCM-1, De Sousa et al, Stem Cell Res 2:188-197; Roslin Cells, Edinburgh, UK) were cultured on CELLstart™ with the serum and feeder free medium STEMPRO® hESC SFM—Human Embryonic Stem Cell Culture Medium (Invitrogen; cat no A1000701), as per manufacturer's protocol. The cells were passaged at a ratio of 1:6 from a 90% confluent well using STEMPRO® EZPassage™—Disposable Stem Cell Passaging Tool (Invitrogen; cat no 23181-010) as per manufacturer's protocol.

Wells were washed with PBS, and medium was placed in all wells and preincubated prior to cell seeding. Cells at passage 64 were seeded into all wells of all plates at the recommended density, and care was taken not to disturb cells after seeding. All wells were cultured with STEMPRO® hESC SFM as per manufacturer's protocol. Incubation was done in a standard culture incubator at 37° C., 5% $CO_2$ in air, at 95% humidity. Cells were observed daily and 100% medium exchanged every 48 hours. All medium was pre-equilibrated to incubator conditions for two hours prior to exchange feeding.

At the end of study, wells were stained with Sigma-Aldrich: Alkaline Phosphatase (AP), Leukocyte (Sigma-Aldrich; Ref 86R-1 KT, Lot 019K4349) as per manufacturer's protocol.
Results Selected images from the cell culture experiments are presented as FIGS. 8-12.

All control wells showed the characteristics and morphology as would be expected with this hESC line under the control culture conditions employed.

The RGD-4RepCT films were successful in sustaining cell attachment and expansion. Even though the growth was much slower than that seen in the control wells, this is thought to be a consequence of the cell line adapting to the new matrix. Cells showed, on initial cell plating, some adherence to the matrix, but non-adherent cells took on the appearance of Embryoid Body (EB) structures, which are seen when hESC:s are placed into non-adherent or low cluster plates to specifically derive EB structures for lineage and differentiation analysis. However, these EB like masses of cells did eventually adhere to the matrix, and from these "clumps", cells were seen to grow and expand, suggesting adaptation to the new matrix.

The cells of this study are continually grown and fed, and are expected to continue to expand. It is furthermore expected that the cells will be capable of passaging and expansion and can then be subsequently assessed for their pluripotency and differentiation status. The positive alkaline phosphatase staining indicates that the cells still exhibit undifferentiated stem cell characteristics.

Example 3

Mouse Embryonic Stem Cells on Recombinant Spider Silk

Background

Mouse embryonic stem cells (mESCs) can be either feeder-dependent (i.e. they need to be cultured on a layer of mouse embryonic fibroblasts, MEFs) or feeder-independent (usually cultured on gelatin). mESCs need to be cultured with LIF (leukemia inhibitory factor) present in the culture medium in order to remain undifferentiated. Their differentiation status (or maintenance of "sternness") can be determined by staining of alkaline phosphatase activity (AP), since pluripotent cells express AP and thus stain positive, or by determination of the transcription of a set of differentiation markers (genes).
Procedure Feeder-dependent mESCs (R1) in passage 17 were thawed and plated onto a layer of MEFs (irradiated, 1 day culture) in a 60 mm Petri dish in DM EM with glutamax (Invitrogen, cat no 31966-021) supplemented with 20% heat inactivated, ES-cell qualified FBS (Invitrogen, cat no 16141-079) and $5 \times 10^5$ units/ml of LIF (Chemicon, ESG 1107). After 2 days, cells were harvested and seeded onto different 4RepCT scaffolds prepared as described in the Examples herein (foam and fiber mesh of 4RepCT and foam and fiber mesh of RGD-4RepCT), as well as onto controls (MEFs or gelatin) in 12-well plates. The split ratio was 1:7. Medium was changed every day, and cells were split every second day (MEFs or gelatin) or every fourth day (4RepCT scaffolds). Longer split intervals were used for cells grown on scaffolds since they proliferated slower. To evaluate whether cells had maintained pluripotency or not, cells were fixed with 4% paraformaldehyde for 1 min and then stained for alkaline phosphatase activity (kit from VECTOR Laboratories) at the end of each passage (p19, p20 and p21), or after 3 days for cells on scaffolds in passage 21 (2 days for cells on gelatin or MEFs). Thus, cells that were maintained on scaffolds had been cultured for 4+4+3=11 days in total at the end of p21, whereas cells maintained on gelatin or MEFs had been cultured for 2+2+2=6 days in the end of p21. Micrographs were taken in an inverted microscope.
Results mESCs grown on gelatin started to differentiate and lose morphology, whereas cells grown on MEFs showed maintained rounded colony morphology and stemness also after 3 passages. mESCs exhibited a lower degree of binding to both foam and fiber mesh compared to the binding to MEFs, as indicated by a lower number of colonies on all scaffold types compared to MEFs. The number of colonies growing on the scaffolds was approximately the same as the number of colonies growing on gelatin.

Once bound to the scaffold material, cells grew and formed colonies on foam and fiber mesh, although some colonies tended to show a less smooth shape as compared to MEFs. Colonies looked similar to those on gelatin. After 4 days without split on foam and fiber mesh, colonies were very large and had partly started to differentiate (i.e. lose their AP positivity). In the third passage (p21), cells were allowed to grow on respective scaffold material for 3 days. Colonies maintained their AP positivity on foam, but showed signs of differentiation on fiber mesh. On 4RepCT foam, colonies were both more numerous and larger, as compared to on RGD-4RepCT foam (FIG. 13).

Figure 13:
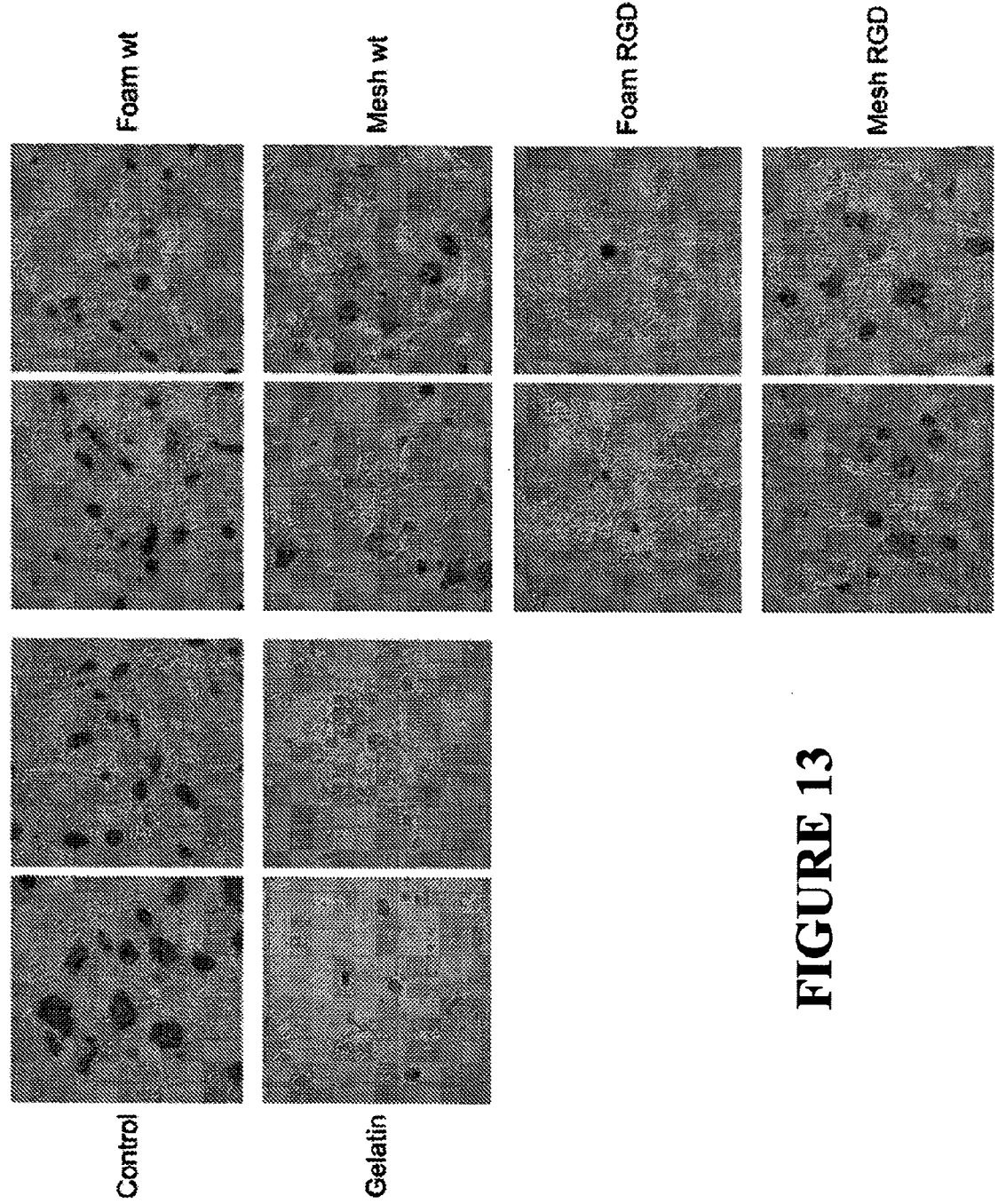
FIG. 13 is a series of pair-wise photographs showing R1 mESCs cultured for three passages on 4RepCT (WT) foam and fiber mesh, RGD-4RepCT (RGD) foam and fiber mesh, on MEFs (control) or gelatin, as indicated.

With reference to FIG. 13, cells were stained for AP activity at day 3 (foam and mesh) and at day 2 (control and gelatin) of the 3rd passage on respective substrate (cell passage 21). Cells growing on 4RepCT (WT) foam showed a maintained stemness, as indicated by AP staining (dark grey colonies) similar to that seen for mESCs on MEFs (control). On the contrary, mESCs growing on fiber mesh showed a weaker staining, which is a sign of differentiation. Colonies on RGD4RepCT foam were smaller but AP positive, indicating less proliferation but maintained stemness.

The differentiation seen in colonies on foam and fiber mesh after 4 days culture without split could be the result of colonies being overgrown and too large, but it could also be due to lack of factors secreted by MEFs, which the cells are dependent on to maintain their pluripotency. This is supported by the observation that cells maintained on gelatin without MEFs had also started to differentiate (already after 2 days). On fiber mesh, the cells started to differentiate after 3 days, at a point when colonies are still of sizes comparable to colonies on MEFs after 2 days.

Conclusion mESCs show binding and proliferation on 4RepCT and RGD-4RepCT foam and fiber mesh. After 4 days, the mESCs on 4RepCT and RGD4RepCT foam and fiber mesh started to differentiate, possibly due to the large size of the colonies. However, when these cells were re-seeded onto newly prepared scaffolds and grown for 3 days, they maintained their stemness on 4RepCT and RGD-4RepCT foam, and the size of the colonies were similar to those seen on MEFs after two days. Slower growth was observed on RGD-4RepCT foam compared to 4RepCT foam. Cells maintained for 2 days on gelatin started to differentiate and mESCs on MEFs will also start to differentiate after 4 days due to large (overgrown) colonies. On 4RepCT foam, attachment, growth and maintained stemness were improved compared to gelatin.

The results are surprising, since mESCs are normally dependent on factors provided by the MEFs to keep their stemness Example 4

Neural Stem Cells (NSCs) on Recombinant Spider Silk

Materials and Methods

Preparation of Wells Containing Scaffolds and Positive Control Wells

4RepCT, IKVAV-4RepCT and RGD-4RepCT were recombinantly produced and purified in analogy to the description in Hedhammar et al (2008), supra. One fraction of the protein solutions obtained was purified from lipopolysaccharides (lps) as described in Hedhammar et al (2010), Biomacromolecules 11:953-959. The protein solutions were sterile filtered (0.22 μm) before being used to prepare scaffolds (film, foam or fibers) as described in Example 1. Half of the scaffolds were made from protein solutions depleted of lipopolysaccharides. Fibers were sterilized through autoclaving for 15 minutes at 121° C. in distilled water at 2.8 bar before being put into the cell culture plates. Scaffolds were prepared in hydrophobic 6-well cell culture plates (Sarstedt). As positive control, wells coated with poly-L-ornitine and fibronectin (PORN) were used. Representative schematics of the 6-well plates with "wild-type" 4RepCT are given below:

| Film, 4RepCT Coated, positive control | Film, 4RepCT | Film, 4RepCT |
| Film, 4RepCT, lps depleted Coated, positive control | Film, 4RepCT, lps depleted | Film, 4RepCT, lps depleted |

| Foam, 4RepCT Coated, positive control | Foam, 4RepCT | Foam, 4RepCT |
| Foam, 4RepCT, lps depleted Coated, positive control | Foam, 4RepCT, lps depleted | Foam, 4RepCT, lps depleted |

| Fiber-mesh, 4RepCT Coated, positive control | Fiber-mesh, 4RepCT | Fiber-mesh, 4RepCT |
| Fiber-mesh, 4RepCT, lps depleted Coated, positive control | Fiber-mesh, 4RepCT, lps depleted | Fiber-mesh, 4RepCT, lps depleted |

In addition, similar plates were prepared by exchanging the "wild-type" 4RepCT scaffold with scaffolds made from IKVAV-4RepCT and RGD-4RepCT, respectively, making a total of 9 experimental plates.

Two wells of a tenth six-well plate to serve as control plate were prepared using the following protocol:
    Addition of 2 ml of poly-L-ornithine solution to each well
    Incubation over night in cell culture incubator at 37° C.
    Removal of poly-L-ornithine solution by aspiration
    Washing twice with PBS 1×
    Addition of 2 ml fibronectin solution per well
    Incubation for 2-4 h in cell culture incubator
    Washing twice with PBS 1×

The remaining four wells of the plate were not coated, i.e. cells were seeded directly onto the polystyrene plastic surface. Thus, the control plate can be schematically represented as:

| Coated, positive control | Empty | Empty |
| Coated positive control | Empty | Empty |

The above described material was used for culturing of NSCs in an undifferentiated state for 48 hours, whereupon the cells were differentiated into astrocytes.

In addition, for a detailed investigation of neural stem cell (NSC) characteristics, a series of cell culture plates with 4RepCT films was prepared as follows:
    3 six-well polystyrene plates (Sarstedt) with 4RepCT film in five of the six wells in each plate. The empty well and one additional well were coated with fibronectin and poly-L-ornithine according to the above. These plates were used for growing the NSCs in an undifferentiated state for 48-96 hours, after which the cells were differentiated into astrocytes, oligodendrocytes and neurons (cf below).
    Control plate: 1 six-well polystyrene plate (Sarstedt). The first row was coated with fibronectin and poly-L-ornithine according to the above, the second row was coated with BSA (bovine serum albumin), and the third row was left uncoated.
    Seven 35-mm polystyrene plates (Sarstedt) with 4RepCT film are prepared to specifically and accurately analyze the proliferation (cell division) rate and proportion of cell death.

Solutions
Medium:
N2 medium (500 ml)
  DMEM:F12 (1:1)+L-glutamine (500 ml bottle; Gibco 11320-074)
  1 ml of 50 mg/ml transferrin (Sigma T-1147; diluted in DMEM:F12)
  100 µl of 100 µM progesterone
  50 µl of 1 M putrescine solution
  30 µl of 500 µM sodium selenite
  1 ml of 12.5 mg/ml insulin
  5 ml Pen/Strep (100×) solution
  N2 medium is a standard medium for the culture of primary (tissue-derived, non-cell-line) cells.
Buffers:
HANKS (500 ml)
  50 ml of 10× HBSS (Gibco 14170), 1.85 g $NaHCO_3$ and 1.95 g HEPES dissolved in $ddH_2O$ and adjusted to pH 7.2. Filter sterilized.
Working solutions:
Poly-L-ornithine (15 µg/ml) in $ddH_2O$, filter sterilized (Sigma P-3655)
Fibronectin (1 µg/ml) in $ddH_2O$, filter sterilized (Sigma F-1141)
NaOH (10 mM)
Stock Solutions:
Putrescine (1 M) in $ddH_2O$ (Sigma P-5780)
Progesterone (100 µM) in EtOH (Sigma P-8783)
Sodium selenite (500 µM) in $ddH_2O$ (Sigma S-5261)
FGF (10 µg/ml) in PBS (R&D Systems, rhFGF-basic)
Insulin (12.5 mg/ml) in 0.02 M HCl, sterile filtered (Sigma I-6634)
Transferrin (50 mg/ml) in DMEM:F12, sterile filtered (Sigma T-1147)
Cortical Neural Stem Cell Cultures Neural stem cells (NSCs) were obtained from the dissociated cerebral cortices of timed pregnant Sprague Dawley E15.5 rat embryos. NSC:s were cultured in 1 ml/962 $mm^2$ of serum-free DMEM:F12 medium, enriched with N2 supplement and grown on poly-L-ornithine/fibronectin coated cell culture dishes. Cells were maintained in a proliferative state using 10 ng/ml FGF2 until reaching 80% of confluence, and passaged twice before use in experiments. After the second passage, cells were plated at 150000 cells/$cm^2$ and allowed to proliferate for 48 h. To determine if the cells had remained undifferentiated, they were stained with nestin.

To induce differentiation of NSCs, FGF2 was withdrawn from the cultures and fresh medium added along with either specific recombinant growth factors or small molecules to induce specific differentiation.

For astrocytic differentiation, 10 ng/ml recombinant CNTF (ciliary neurotrophic factor) was added. CNTF and other factors of the interleukin-6 family (e.g., CT-1, LIF) induce a rapid (within 48 hours) and efficient (>>50%) differentiation of cortical NSCs into cells with an astrocytic morphology and positive for the archetypical astrocyte marker GFAP (Hermanson et al (2002), Nature 419:934-939), and it has recently been shown by calcium imaging techniques that these cells are functional astrocytes (Andersson et al (2011), Mol Cell Neurosci, Epub 14 Jan. 2011).

For neuronal differentiation, either 0.5-1.0 mM valproic acid (VPA) or 10 ng/ml recombinant BMP4 (bone morphogenetic protein 4) and 10 ng/ml Wnt3a were administered after FGF2 withdrawal. VPA induces a rapid (within 72 hours) differentiation of NSCs into 10-30% of early, electrophysiologically non-responsive cells with neuronal morphology, which are positive for the neuronal marker antibody TuJ1. Gene expression analysis of VPA-induced differentiated cells suggests that they initiate a differentiation program towards inhibitory (GABAergic) neurons. BMP4+Wnt3a induce a slow (5-14 days; herein 7 days) differentiation of NSCs into 10-30% of mature, electrophysiologically active cells with neuronal morphology, which are positive for all pan-neuronal markers, including TuJ1 (Leão et al (2010), PLoS One 5:e13833). Gene expression and physiological analysis of BMP4+Wnt3a-induced differentiated cells suggest that they initiate a differentiation program towards excitatory (glutamatergic) neurons. BMP4+Wnt3a treatment also results in increased astrocytic differentiation contributing to the mature phenotype of the neuronal cells, as compared to cells differentiated using VPA.

For oligodendrocytic differentiation, 50 ng/ml of thyroid hormone (T3) was added. T3 induces an enhanced differentiation (1-20%) into cells with oligodendrocyte morphology, which are positive for most archetypical oligodendrocyte characteristic proteins (e.g. MBP) within 4-7 days. Although the differentiation is less efficient than that resulting from other protocols, it should be noted that the number of oligodendrocytic cells in control cultures (only FGF2 withdrawal) is very low, such as <<1%.
Immunocytochemistry For immunocytochemistry, cultures were washed once with PBS and fixed using 10% formalin (Sigma) for 20 min. Next, cells were washed 3×5 min with PBS+0.1% Triton X100. The primary antibody was incubated over night at 4° C., (antibody dilution 1:500 in PBS+0.1% Triton X100+BSA 0.1%).

Next, plates were washed 6×5 min with PBS+0.1% Triton X100, and incubated for 1 h at room temperature with secondary antibody.

The following antibodies were used: mouse monoclonal anti-smooth muscle actin (SMA) from Sigma (1:1000); rabbit polyclonal anti-glial fibrillary acidic protein (GFAP) from DAKO (1:500); mouse TuJ1 (to detect neurons) from CoVance (1:500), and rat anti-MBP (MAB386) from Chemicon (1:250) followed by appropriate species specific Alexa-488 and Alexa-594 conjugated secondary antibodies (Molecular Probes; 1:500). Nuclei were visualized using Vectashield containing DAPI (Vector Laboratories, Inc.). Fluorescent and brightfield images were acquired using a Zeiss Axioskop 2 mot plus/Axiocam MRm camera with Axiovision software.
Proliferation Assay Cells were fixed with 10% formalin 15 min after the addition of 50 µM 5-ethynyl-2'-deoxyuridine (EdU; Invitrogen) followed by immunocytochemistry according to the supplier's recommendations.
Cell Death Assay A Live/Dead kit (Invitrogen) was used to differentiate between living and dead cells attached to the scaffolds. Plates were rinsed twice with pre-warmed PBS (37° C.) before proceeding with the assay according to the manufacturer's recommendations. The assay enabled identification of live cells (green color) and dead cells (red color).
Results
Experiments on Proliferation and Viability of Neural Stem Cells when Grown and Expanded on Fiber-Mesh, Foam or Film, and Potential to Differentiate into Astrocytes, Neurons and Oligodendrocytes. Unless Otherwise Stated, all Experiments were Performed in Triplicates (n=3).

Figure 14:
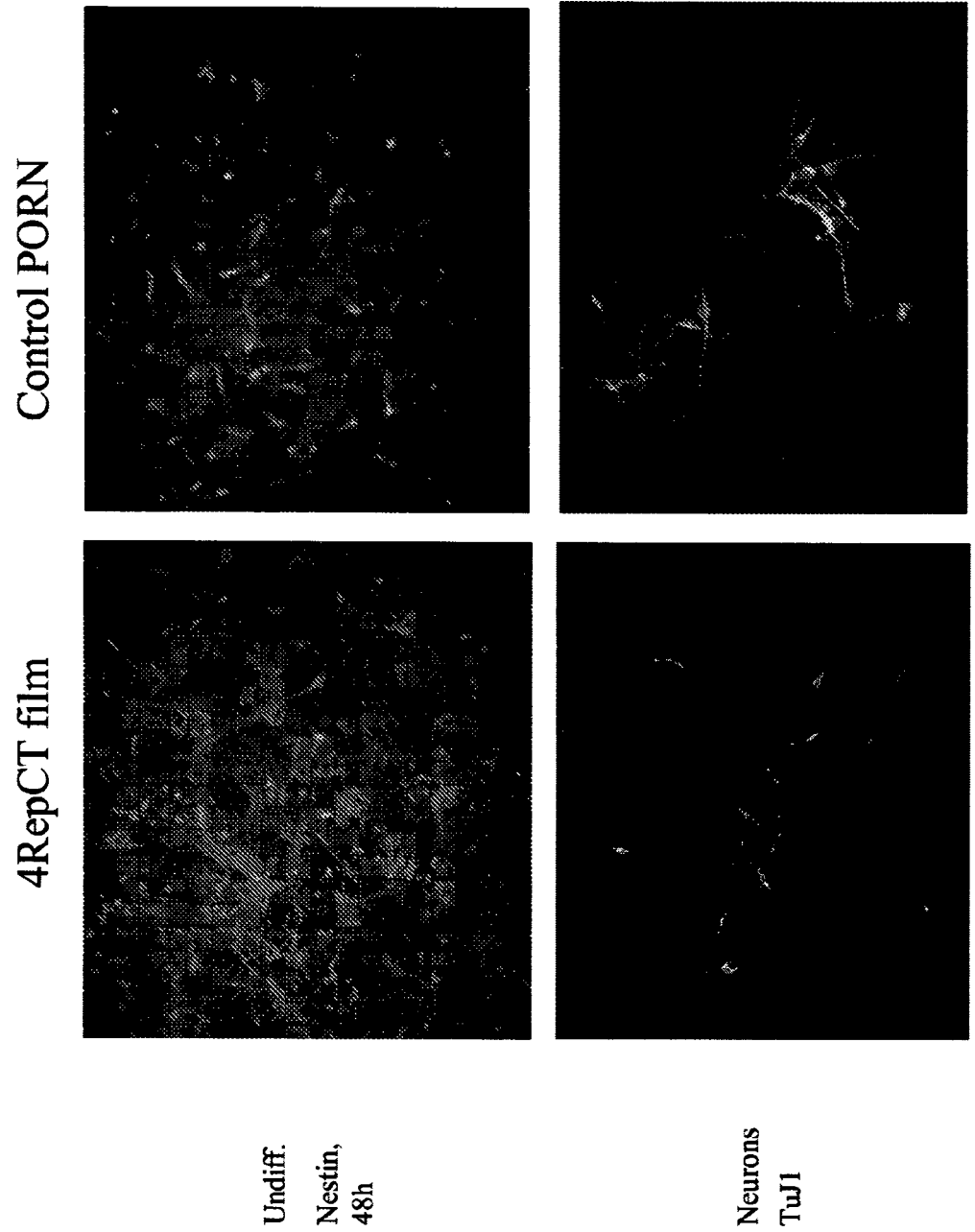
FIG. 14 shows NSCs cultured on 4RepCT film and control (PORN) as indicated, maintained undifferentiated (upper row) and subjected to neuronal differentiation (lower row). Cells have been stained with nestin, (upper row) and TuJ1 (lower row).

After 48-72 h, NSCs proliferated normally on foam and film. In wells were a part of the plastic was exposed next to the film and foam, cells only grew on the films and foams. The morphology was indistinguishable from control cultures (poly-L-ornithin and fibronectin). When stained with nestin (48 h post seeding), the appearance of NSCs on 4RepCT film was indistinguishable from that of cells growing on poly-L-ornithin and fibronectin (FIG. 14).

In wells with silk scaffolds that had been coated with fibronectin and poly-L-ornithine, the cells grew all over the plate wells, which is expected since also the plastic surface of the well is coated. No obvious or significant differences were seen at any stage beyond 48 hours in proliferation or cell death between NSCs grown on 4RepCT films compared to control. Also, no obvious difference was seen between NSCs grown on 4RepCT foam structures compared to control (n=1). In wells with BSA coating, the cells had not attached and were dying within 5 days, as expected.

Figure 16:
FIG. 16 shows results from the EdU-assay of NSCs growing on 4RepCT film (at 48 h post seeding), as described in Example 4.

NSCs remained morphologically indistinguishable from stem cells in control cultures in the presence of FGF2 when grown on 4RepCT film and foam structures. They were viable (85% as determined by Live/Dead staining), proliferating (28% as determined by the EdU assay, controls 20-30%) and remained in an undifferentiated state, and no significant differences compared to control cultures (using poly-L-ornithine and fibronectin) were detected (FIGS. 14, 16 and 17).

To test whether the NSCs remained multipotent with regard to differentiation capacity, a series of protocols to test differentiation into various neural lineages (e.g., neurons, astrocytes, oligodendrocytes) were applied as described in detail in the Methods section above.

Figure 15:
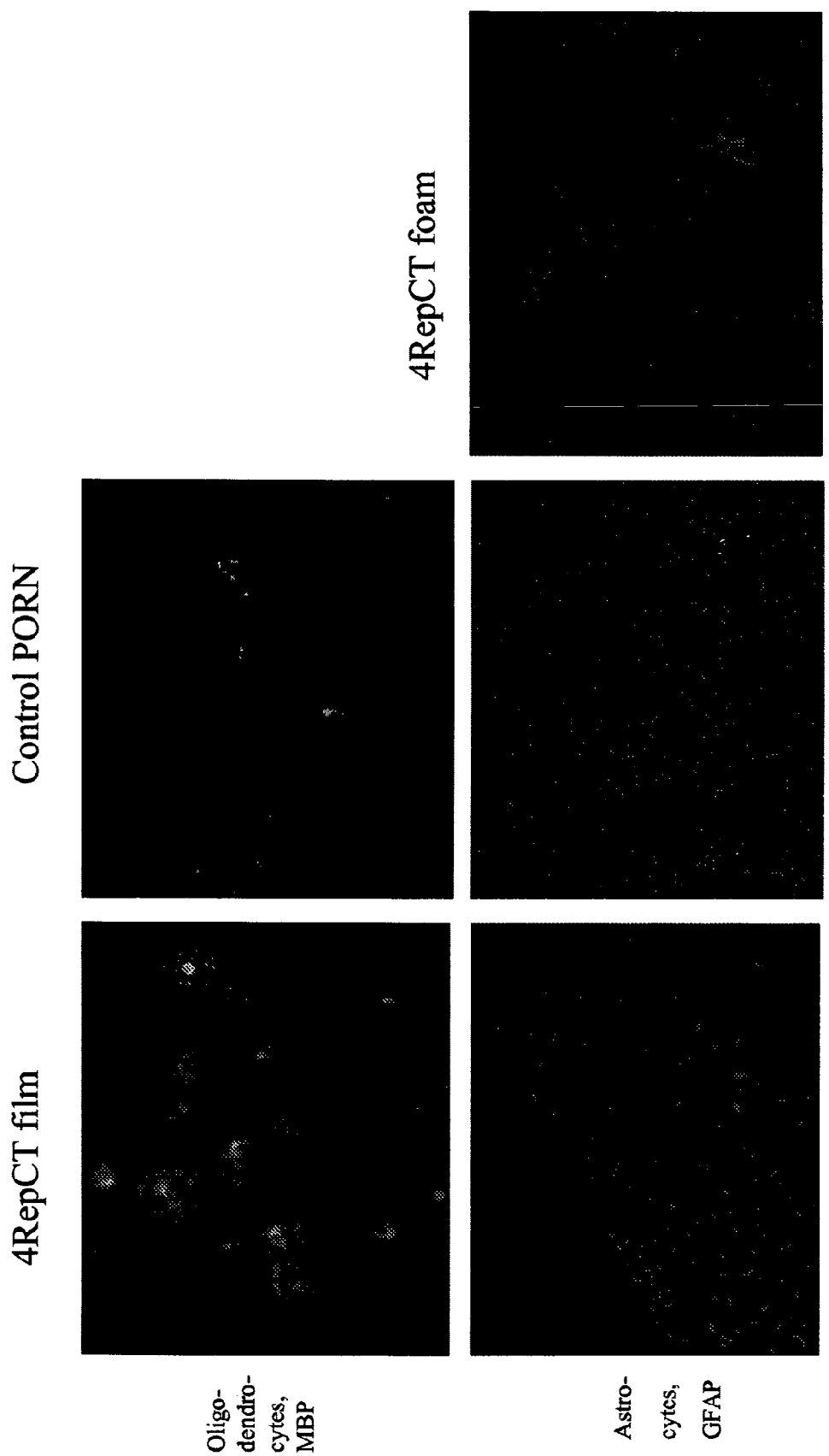
FIG. 15 shows NSCs cultured on 4RepCT film and control (PORN) as indicated, maintained undifferentiated and subjected to oligodendrocyte (upper row) and astrocyte (lower row) differentiation. Cells have been stained with MBP (upper row) and GFAP (lower row). Also, the appearance of NSCs maintained undifferentiated on 4RepCT foam and subjected to astrocyte differentiation is shown.

When NSCs grown on 4RepCT films were treated with CNTF as described in Methods, they differentiated rapidly and efficiently into cells with astrocytic morphology expressing the archetypical marker protein GFAP with no significant difference in efficiency, proliferation or cell death compared to control cultures (poly-L-ornithine and fibronectin) (FIG. 15)

When NSCs grown on 4RepCT films were treated with BMP4+Wnt3a as described in Methods, they differentiated into cells with neuronal morphology positively stained with the archetypical antibody TuJ1 with no significant difference in efficiency, proliferation or cell death compared to control cultures (poly-L-ornithine and fibronectin) (FIG. 14).

When NSCs grown on 4RepCT films were treated with VPA as described in Methods, they differentiated into cells with neuronal morphology positively stained with the archetypical antibody TuJ1. Whereas no significant difference in proliferation or cell death compared to control cultures were detected, a slightly lower efficiency in differentiation was observed (around 10-50% differentiated cells compared to control numbers). It has previously been observed that VPA-mediated differentiation is affected by substrate, likely due to the fact that the small molecule VPA, which, in contrast to recombinant growth factors, acts intracellularly, gets attached to and degrades on the substrate. Nevertheless, VPA-mediated neuronal differentiation of NSCs was indeed observed on 4RepCT films.

When NSCs grown on 4RepCT films were treated with T3 as described in Methods, they differentiated efficiently into cells with oligodendrocyte morphology expressing the archetypical marker protein MBP with no significant difference in efficiency, proliferation or cell death compared to control cultures (n=2). It was observed that the MBP staining suggested a possibly less mature morphology than the cells differentiated under control conditions. It should be noted, however, that oligodendrocyte maturation is complex and that such an observation thus needs careful and extended analysis before becoming conclusive (FIG. 15).

No significant differences in morphology, proliferation, viability, or differentiation capacity in any experiment were observed upon comparison between scaffolds made from the 4RepCT protein which had and had not been lps depleted. Further, no obvious negative differences in morphology, proliferation, or viability were seen in NSCs grown on IKVAV-4RepCT or RGD-4RepCT (n=1).

Example 5

Islets of Langerhans (A) and Single Beta Cells, Alone (B) or in Combination with Other Cells (C), on Recombinant Spider Silk Scaffolds Background Transplantation of the islets of Langerhans is one of the most promising approaches to finding a widely applicable treatment of severe type 1 diabetes. Unfortunately, currently available procedures suffer from low efficacy due to loss of function and survival of the pancreatic cells (Alejandro et al (2008), Transplantation 86:1783-1788). The low success rates are incompletely understood, but prior to transplantation, during islet isolation, the environment surrounding the cells is disrupted, which leads to a loss of vascularization and innervations and to altered interactions with the extracellular matrix. This has been implicated as a major cause of the limited survival and function (van der Windt et al (2007), Xenotransplantation 14:288-297; Kilkenny and Rocheleau (2008), Mol Endocrinol 22:196-205). The endocrine parts of the pancreas, unlike the exocrine part, do not produce a basement membrane of their own but rather depend on their surrounding environment, indicating again that the right niche might be of importance (Otonkoski et al (2008), Diabetes Obes Metab 10 Suppl 4:119-127).

Another major obstacle to islet transplantation is the limited availability of beta cells due to shortage of donors. Beta cells, unlike many other cell types, have so far not been possible to propagate in vitro, since efforts to expand them result in dedifferentiation (Beck et al (2007), Tissue Eng 13:589-599). Thus, the establishment of an environment which is optimized for islets and beta cells is necessary, both for the study and propagation of pancreatic islets and islet-cells (beta cells), and for the design of an artificial islet/beta cell carrier for transplantation. In order to accomplish this, a highly versatile biomaterial is needed as a scaffold.

Recently, success in producing a recombinant spider silk protein under physiological conditions was reported by the inventors' research group. Polymers of the protein can yield a strong and highly versatile material that can adopt various physical forms, e.g. three-dimensional fiber-meshes, foams or films. The stability of such "scaffolds" allows retrieval of cells for subsequent transplantation. Moreover, the scaffolds can be functionalized with specific cell binding motifs, suitable for adherence of e.g. beta cells. These properties make the protein an excellent candidate for the production of scaffolds that mimic the natural cell environment and thus provide support for islets of Langerhans and individual beta cells after isolation.

Subsequent to transplantation, it is important that the islets are well adopted into the host environment, for example with proper vascularization. At the same time, negative host immune responses, e.g. instant inflammatory reaction, should be avoided. The formation of new capillaries requires endothelial cells, and of course these cells readily tolerate contact with blood. Mesenchymal stem cells can up-regulate the expression of important growth factors in endothelial cells and also produce proteases, and can thereby create pathways for new capillaries (Zacharek, A. et al. Neurosci Lett 404, 28-32 (2006)). The experiments described herein indicate that a personalized islet environment can be built up by using a functionalized silk scaffold, which allows adherence and combined growth of islet cells, endothelial cells (cf Example 6) and mesenchymal stem cells (cf Example 1).

Experimental Material

Recombinant spider silk protein, 4RepCT (SEQ ID NO:2), prepared essentially as described in Hedhammar et al (2008), supra, in the form of scaffold structures prepared as described in Example 1. The material was used in the original form 4RepCT, or in the form of variants modified by the incorporation of different cell-binding motifs related to the extracellular matrix, for example RGD, IKVAV, and YIGSR, or by the incorporation of the tripeptide RGE. In other variants, the spidroin N-terminal domain (NT) and a C-terminal His-tag were included, yielding a protein designated NT4RepCTHis (SEQ ID NO:5).

Islets of Langerhans (human and rodent)
Cells from human and mouse islets, e.g beta cells
Endothelial cells
Mesenchymal stem cells Experimental Methods Cell Isolation Human islets of Langerhans were isolated at the Division of Clinical Immunology at Uppsala University, Sweden, by using a modified semi-automated digestion-filtration method and were thereafter cultured in CMRL-1066 medium with supplements and 10% human serum (Johansson et al (2008), Diabetes 57:2393-2401).

Rodent islets of Langerhans were isolated by collagenase treated pancreata, digested by a continuous mechanic shaking, separated from exocrine tissue, and thereafter cultured in RPM I-1640 medium with supplements and 10% FBS (Nyqvist et al (2005), Diabetes 54:2287-2293).

Single cells were prepared from islets from 10 months old obese mice or from islets from human donors. The single cells were isolated according to an accutase digestion protocol. In brief, 200 islets were pooled and washed twice with 1×PBS. Thereafter, 1 ml accutase was added to the islets. The islet-accutase suspension was incubated in 37° C. for 10-15 min with two steps of mild shaking, after which islet single cells were washed twice with 1×PBS and then plated and cultured on different variants of 4RepCT scaffolds in various physical forms, and without and with various peptide motifs.

Cell Culture

Human islets (20 islets/well) in combination with 4RepCT scaffolds were cultured in CMRL-1066 with supplement (Johansson et al, supra).

Rodent islets (10 islets/well) and single islet cells in combination with 4RepCT scaffolds were cultured in supplemented RPMI-1640 medium (Nyqvist et al, supra).

Commercially available, human microvascular endothelial cells were obtained and maintained in culture according to the provider's instructions in a well-known manner.

Commercially available, human mesenchymal stem cells derived from bone marrow were obtained and maintained in culture according to the provider's instructions in a well-known manner.

Cell culture plates (hydrophobic plastic) were used as control for islets (as islets usually are cultured floating free in these plates). Tissue-culture treated plastic was used as control for growth of single cells.

Adherence Assay

A number (10-25) of islets were plated onto normal culture plastics as control and onto different variants of 4RepCT scaffolds and cell-binding motifs. Specific islet medium was used, and 4RepCT and islets were cultured for 5 days. During this time, adherent islets were counted every day. Medium change was performed on day 2 and insulin release was studied on day 5. Thereafter, the islets within 4RepCT scaffolds were cultured for up to 2 weeks, whereupon islet survival was analyzed. In one experiment using islets from a human donor, the islets were cultured for 12 weeks.

Assessment of Function and Survival of Islets and Islet Cells

Signal transduction, both in the individual islets and the islets' cells, both human and rodent, was studied subsequent to culture of the intact islets or islet cells under different growth, function and survival promoting conditions, and for different periods of time, in the various 4RepCT-based scaffolds. Islet cell growth, function and survival were monitored with the help of various fluorescent dyes and biosensors for specific steps in the signal transduction pathway. Several key events were tested: glucose metabolism, cytoplasmic concentration of free $Ca^{2+}$ ($[Ca^{2+}]_i$), proliferation, and apoptosis/necrosis. It is also possible to test for example ATP production, exocytosis, and stimulus-induced insulin gene transcription.

In Vivo Transplantation

Islet and 4RepCT transplantation (e.g. into the anterior chamber of the eye) is done according to the method developed in P. O. Berggren's laboratory (Speier et al (2008), Nat Protoc 3:1278-1286; Speier et al (2008), Nat Med 14:574-578). In this way, the cornea is used as a window to study cell survival, function and integration in a living organism, under both physiological and diabetic conditions.

Results

A) Culturing of Islets

The use of 4RepCT, both the wild type and variants modified by incorporation of different extracellular matrix related cell-binding motifs (e.g. RGD, RGE, IKVAV and YIGSR), may define an optimal environment for maintaining pancreatic islet function and survival after isolation.

Islets were isolated from human pancreata (N=7) and mouse pancreata (N=10).

The islets were cultured for from 3 h to 3 days in their specific medium and serum. Thereafter, they were plated onto different variants of 4RepCT (fiber, foam and film with incorporated peptidic motifs; none (wild-type; WT), RGD, RGE, IKVAV and YIGSR). Islets were also plated on NT4RepCTHis.

Figure 18:
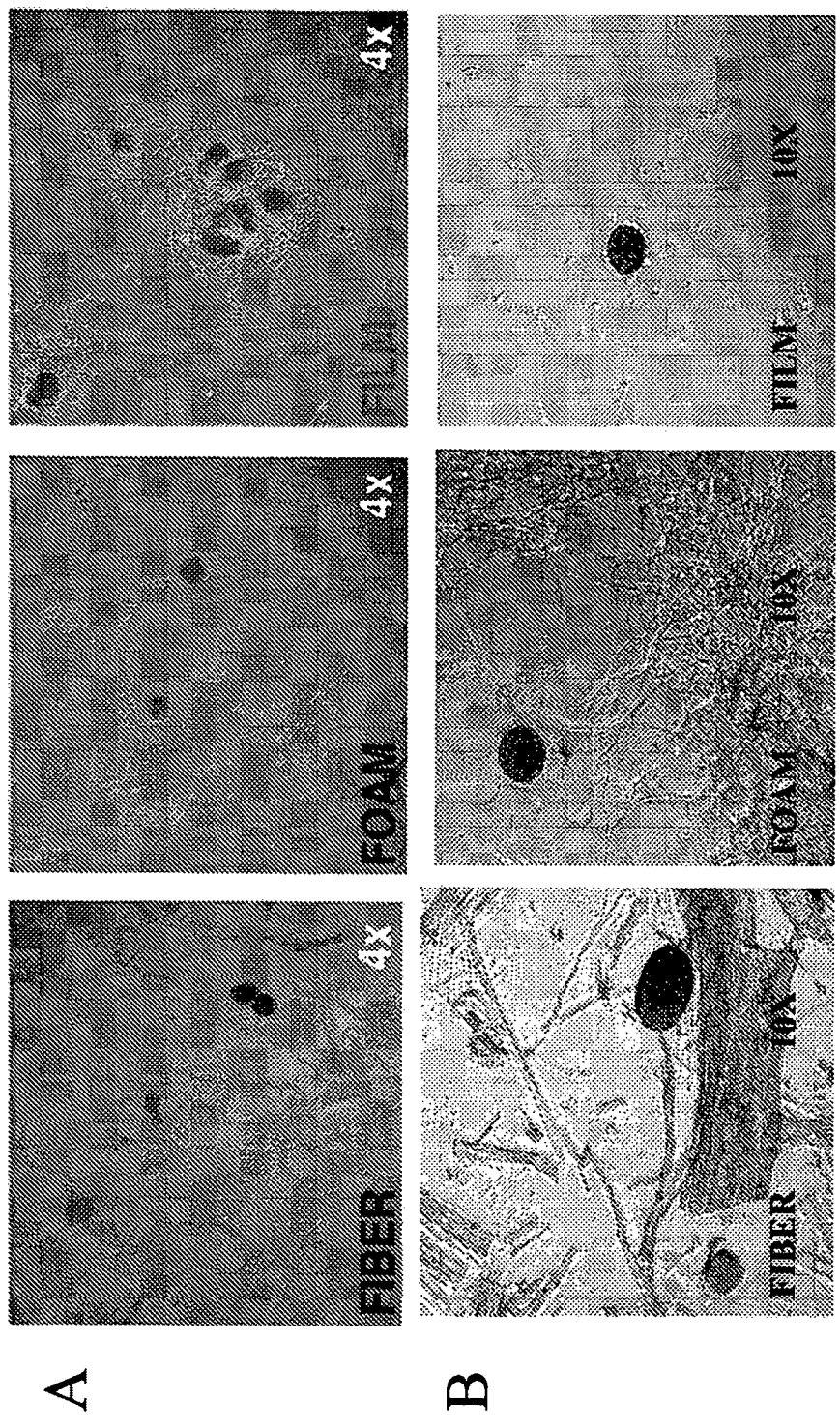
FIG. 18 is a series of photographs showing that human (A) and mouse (B) islets of Langerhans adhered to 4RepCT fiber, foam and film, respectively, after 5-7 days of culture.
Figure 19:
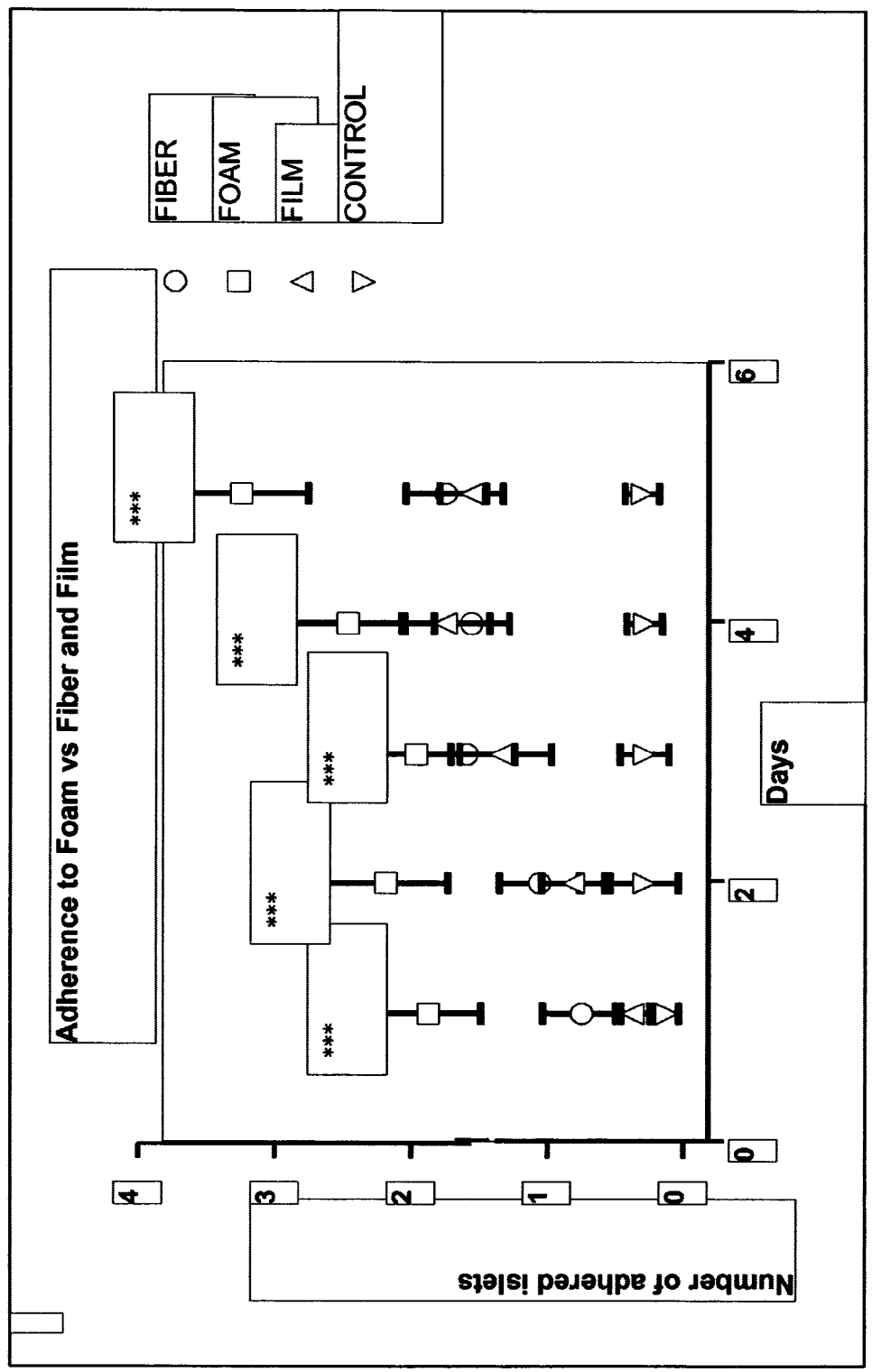
FIG. 19 is a diagram showing that mouse islets showed significantly higher adherence to the 4RepCT foam structure at all time points as compared to corresponding fiber and film, and to control (n=16, ***P=0.001).

Islets adhered spontaneously to the 4RepCT variants, as shown in FIG. 18A (human) and FIG. 18B (mouse). Empty culture plates (hydrophobic plastic) were used as control. From these results, a preferential adherence to the foam scaffold structure was observed, as compared to film and fiber (FIG. 19). Therefore, all tests of adherence and function were continued on foam scaffolds.

Figure 20:
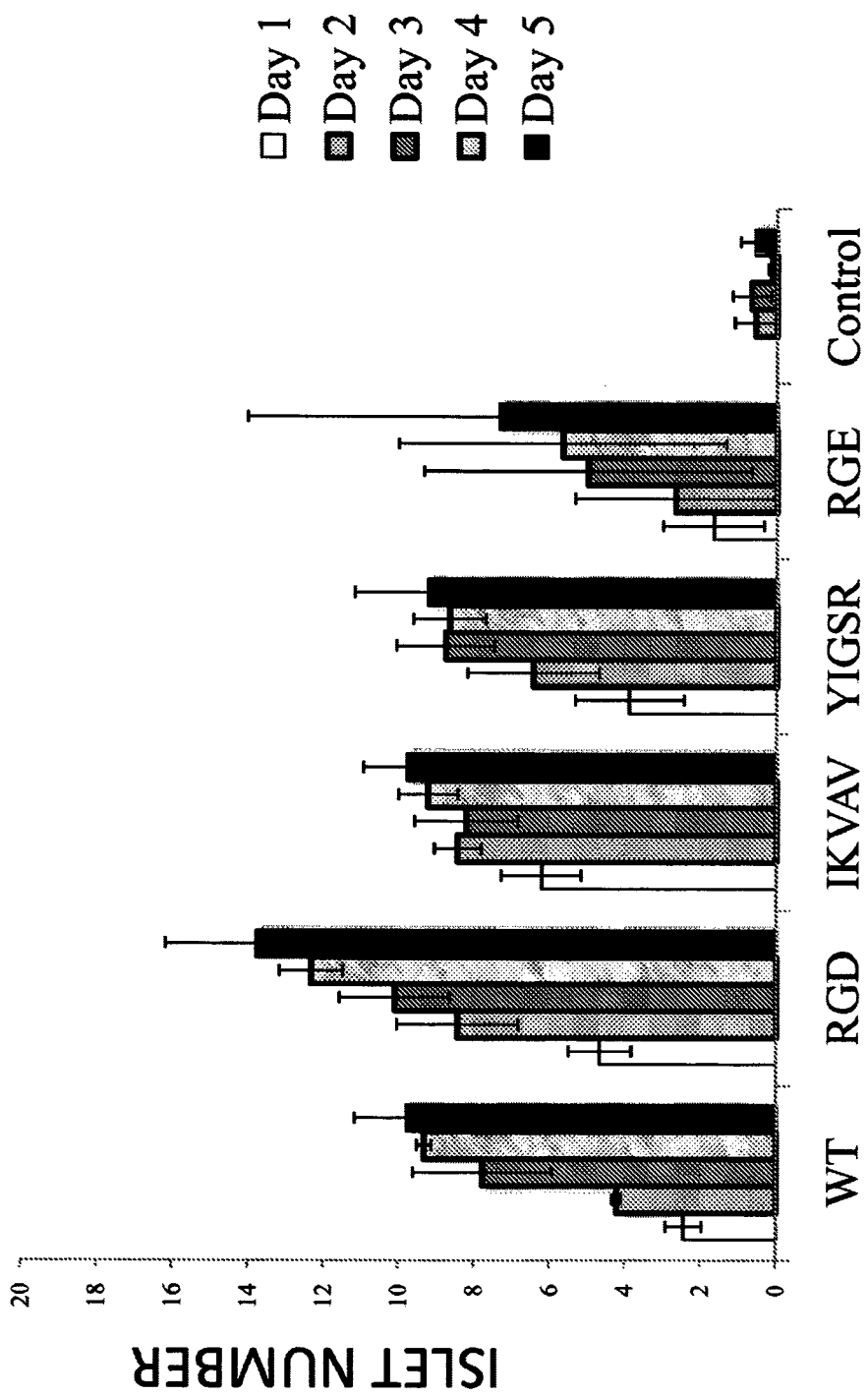
FIG. 20 is a diagram showing the number of human islets adhered to foam of 4RepCT without (WT) and with different peptide motifs as indicated after culture for 1-5 days (n=3±SEM; n=2 for RGE±StdDev).
Figure 21:
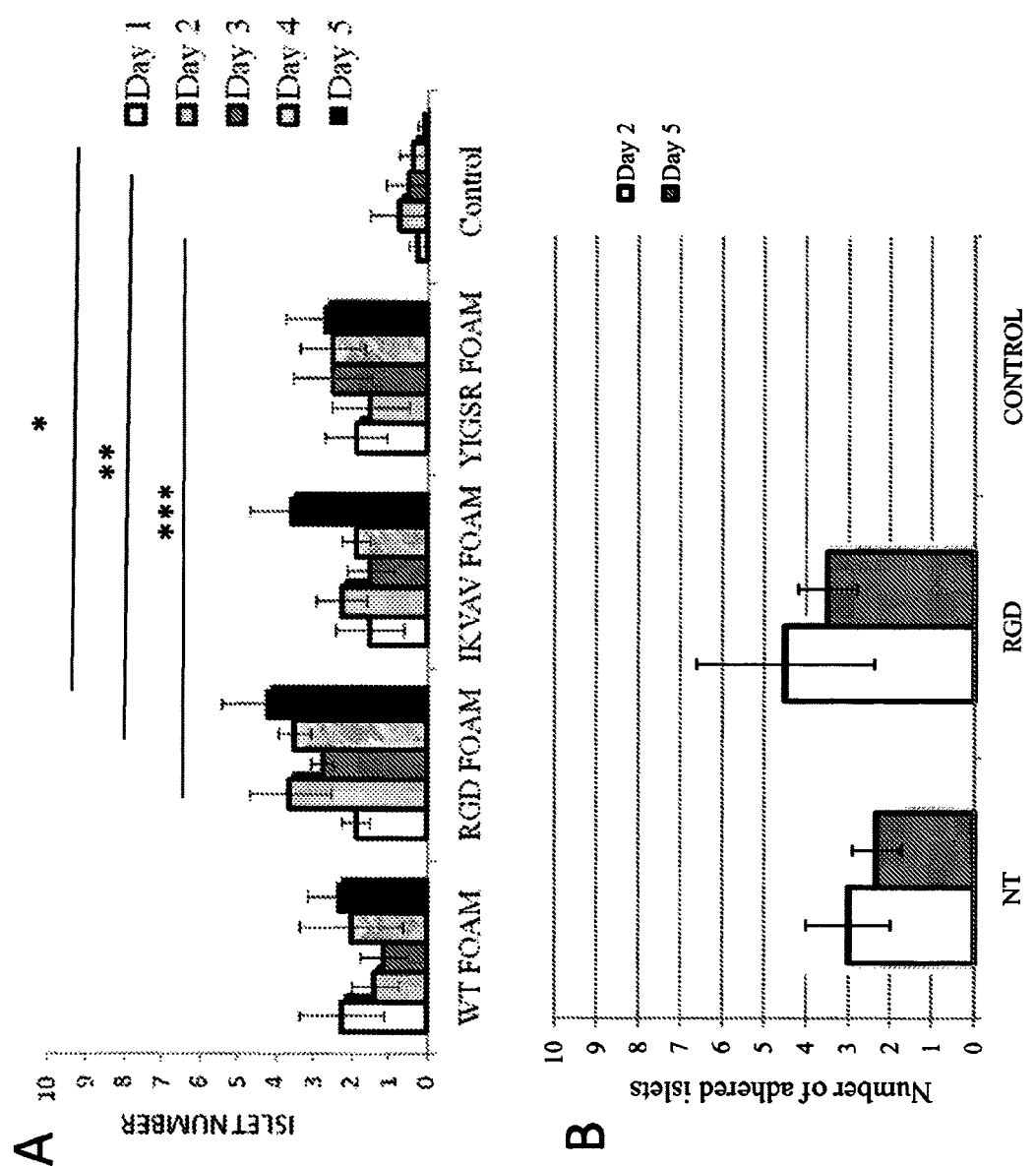
FIG. 21 is a pair of diagrams showing islet adherence to the different scaffolds; A: Mouse islets adherence to foam of 4RepCT without (WT) and with different peptide motifs as indicated after culture of 1-5 days (n=4, ±SEM, *=p<0.05, =p<0.01, *=p<0.001); B: Mouse islets adherence to NT4RepCT foam compared to RGD-4RepCT and control after culture of 2 days (n=1, experiment done in triplicates, ±SEM)

Adhered islets were counted every day after plating until day 5. Islets adhered in different numbers, as shown in FIG. 20 (human islets, n=3 except for RGE where n=2; all experiments done in triplicates) and FIGS. 21A-B (mouse islets, n=4 (A) and n=1 (B); experiments done in triplicates). A comparison between different motifs was also performed, and a significant increase in adhesion was seen for 4RepCT comprising the motif RGD on days 2, 4 and 5 (FIG. 21A). Islets also adhered to NT4RepCTHis in an increased manner compared to the control (FIG. 21B).

Islets in contact with 4RepCT were glucose challenged, and insulin release was measured on day 5. The results are shown in FIGS. 22A-F. Insulin was released from mouse islets cultured on 4RepCT (FIG. 22A-B; n=6; experiments done in duplicates). Mouse islets also released insulin when cultured on NT4RepCTHis (FIG. 22D; n=1; experiment done in triplicates). Human islets released insulin after glucose stimulation when cultured on 4RepCT (FIG. 22E; n=3;

experiments done in triplicates). Not all islets adhered to the foam scaffolds, and therefore the adhered islets' insulin release function on days 2 and 5 was tested in separate experiments (FIG. 22C (mouse), FIG. 22F (human)).

The glucose stimulated insulin release by the islets is similar after culturing in the wells coated with the 4RepCT scaffolds, with or without peptide motifs, and the control wells. This indicates that islets cultured with the 4RepCT scaffolds maintain their function. Also, islets cultured on NT4RepCTHis exhibited maintained function (FIG. 22D).

The measured insulin release at the initial basal glucose (black bars) is higher in a few mouse experiments on 4RepCT scaffolds with or without peptide motifs, and this is believed to be a result of exposure to the initial culture medium, which is difficult to wash away from the scaffolds, and of a high variability between these experimental islets. The stimulation index (Stimulated insulin/Basal insulin) is measured separately in each well and shows that all islets on scaffolds responded to glucose by releasing insulin equally well as the control (FIG. 22B).

The human islets cultured on 4RepCT scaffolds (with and without peptide motifs) showed a low basal insulin level regardless of cell-binding motif, and exhibited a satisfactory stimulated insulin release after high glucose challenge.

Figure 23:
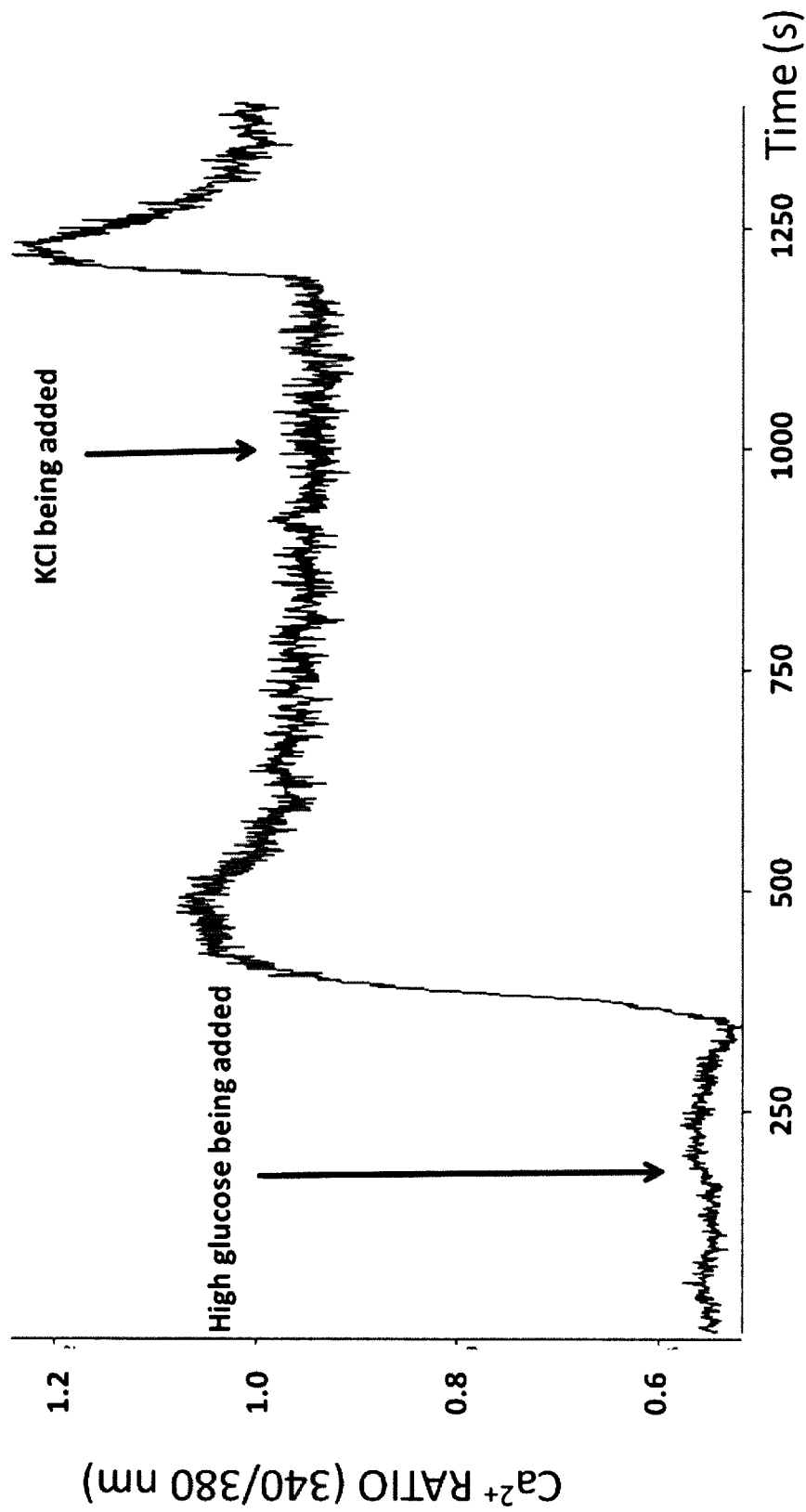
FIG. 23 is a diagram which illustrates the $[Ca^{2+}]_i$ response after high glucose and KCl stimuli of one islet cultured for 1 day on RGD-4RepCT.

The cytoplasmic concentration of free $Ca^{2+}$ ($[Ca^{2+}]_i$) was measured for islets cultured on scaffolds bearing different motifs. The islets responded to high glucose and showed an increase in $Ca^{2+}$ as evidenced by ratiometric imaging analysis (FIG. 23). No difference between control islets and islets cultured on scaffolds was observed.

Figure 24:
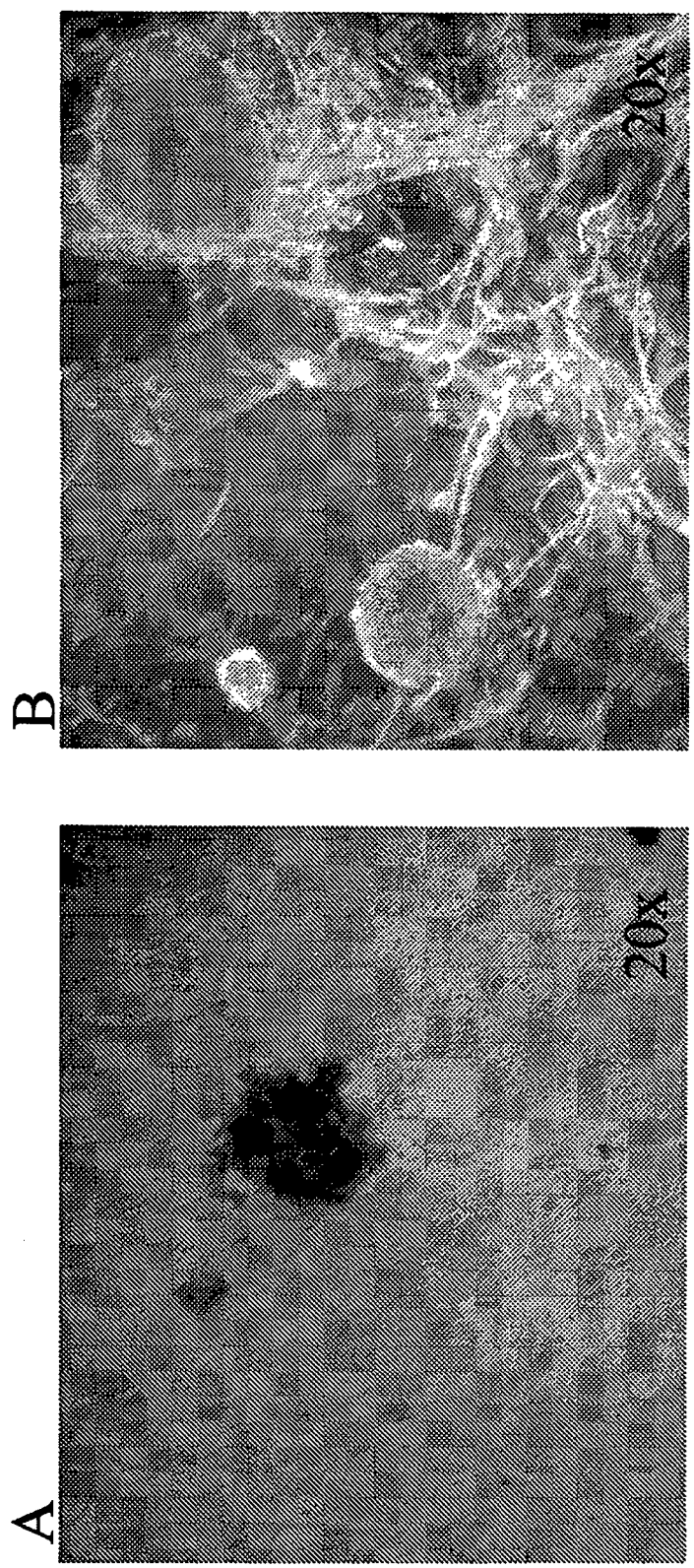
FIG. 24 is a pair of photographs, in which morphologic analysis of human islet viability shows more dispersed islets in the control group (A) compared to the more intact adhered islets on RGD-4RepCT foam (B).

Islets were cultured (medium change every second day) for 2 weeks. Thereafter, islets were counted and scanned for viability (e.g. necrosis). The islet morphology of islets on scaffolds was preserved after 2 weeks, whereas control islets exhibited islet degradation as visualized by a more irregular shape and suspended single cells (FIG. 24). Necrotic bodies were analyzed by light microscopy. More necrotic bodies were seen in the control islets, whereas islets cultured on 4RepCT scaffolds (with and without peptide motifs), both mouse and human, were more intact and viable.

Islets from a young human donor were long-term cultured and tested for islet-like cluster formation and insulin release at day 5 and after 4 weeks and 12 weeks. Islets on the foam scaffold with the RGD motif exhibited an increased islet-like cluster formation after 4 weeks (Table 6).

TABLE 6

| Scaffold | Number of islets and islet-like clusters |
|---|---|
| 4RepCT | 3 ± 1 |
| RGD-4RepCT | 71 ± 16 |
| IKVAV-4RepCT | 4 ± 1 |
| YIGSR-4RepCT | 6 ± 1 |
| RGE-4RepCT | 4 ± 1 |
| Control | 3 ± 1 |

Figure 25:
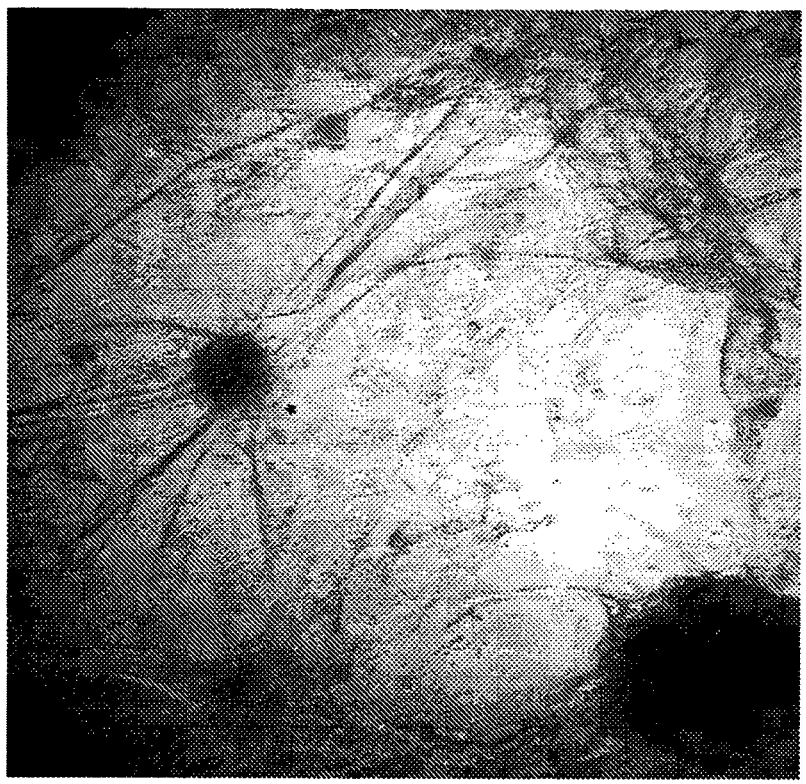
FIG. 25 is a photograph enabling morphologic analysis of human islets after long-term culture (30 days) on RGD-4RepCT. An islet can be seen above the star.
Figure 26:
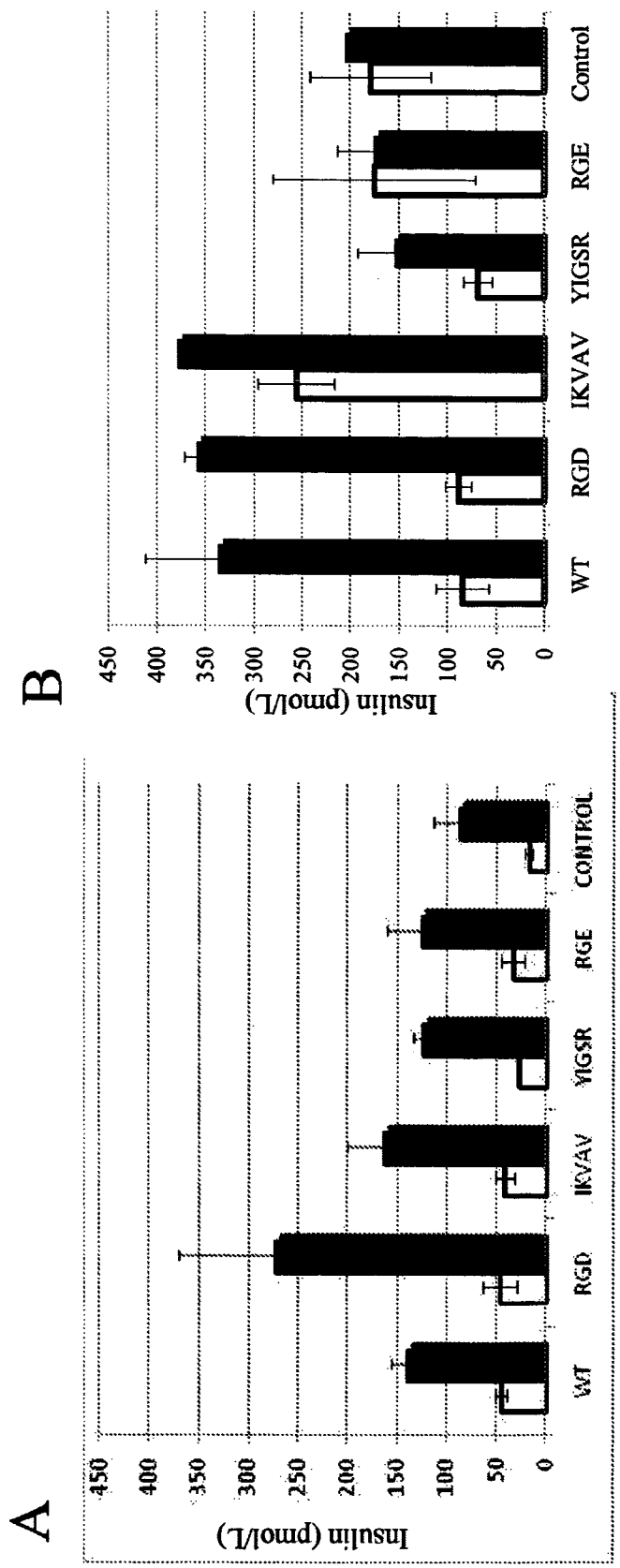
FIG. 26 is a pair of diagrams showing insulin release per islet after long-term culture of human islets with 4RepCT without (WT) and with different peptide motifs as indicated. The insulin release (pmol/l) on day 5 (A) and after 4 weeks (B). Low glucose (3 mM) stimulation gave the basal level of insulin release (white) and high glucose (16.7 mM) gave the stimulated insulin release (black) (n=1; experiments done in triplicates).
Figure 27:
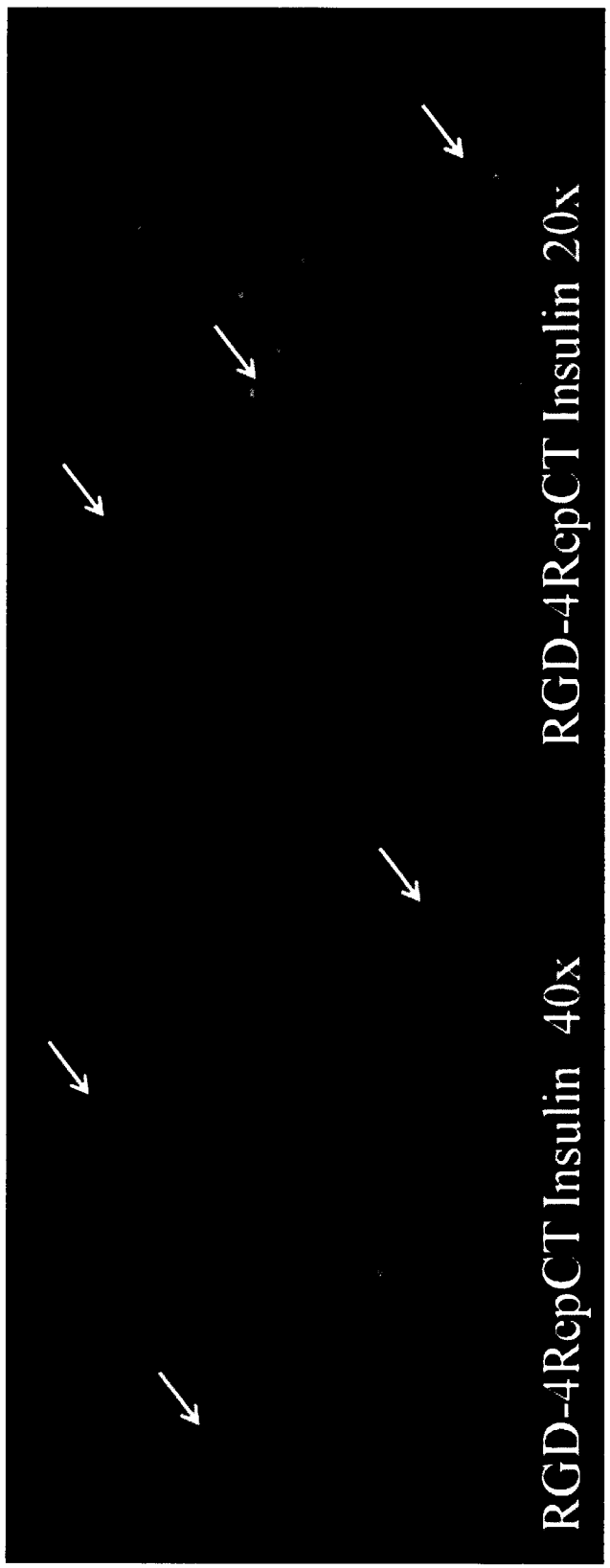
FIG. 27 is a pair of photographs at the indicated magnification, showing positive staining of insulin-producing cells (white, pointed to by arrows) in human islets and islet-like cluster after long-term culture (78 days) on RGD-4RepCT foam (light grey).

These clusters adhered to the scaffold, and cells between the islets and islet-like clusters grew along the RGD-4RepCT scaffold structure (FIG. 25). Such cell growth between islets and along the foam structures was also seen on scaffolds having the YIGSR motif. Insulin release increased over time for scaffolds with RGD and was maintained in scaffolds with the YIGSR motif, and these results demonstrate satisfactory function compared to control islets after such a long time of culture (FIG. 26). Staining showed insulin positive cells in the islets and islet-like clusters (FIG. 27).

B) Culturing of Beta Cells Alone

Single cells (beta cells in majority) were isolated from islets of Langerhans from obese mouse pancreata (n=3) and from human islets (n=1). The single cells were plated and cultured for 3-7 days on different variants of 4RepCT (fiber, foam and film with the incorporated motifs: none (wild-type; WT), RGD, RGE, IKVAV and YIGSR).

Morphology analysis showed that the single cells adhered in different manners onto different variants of 4RepCT.

Figure 28C:
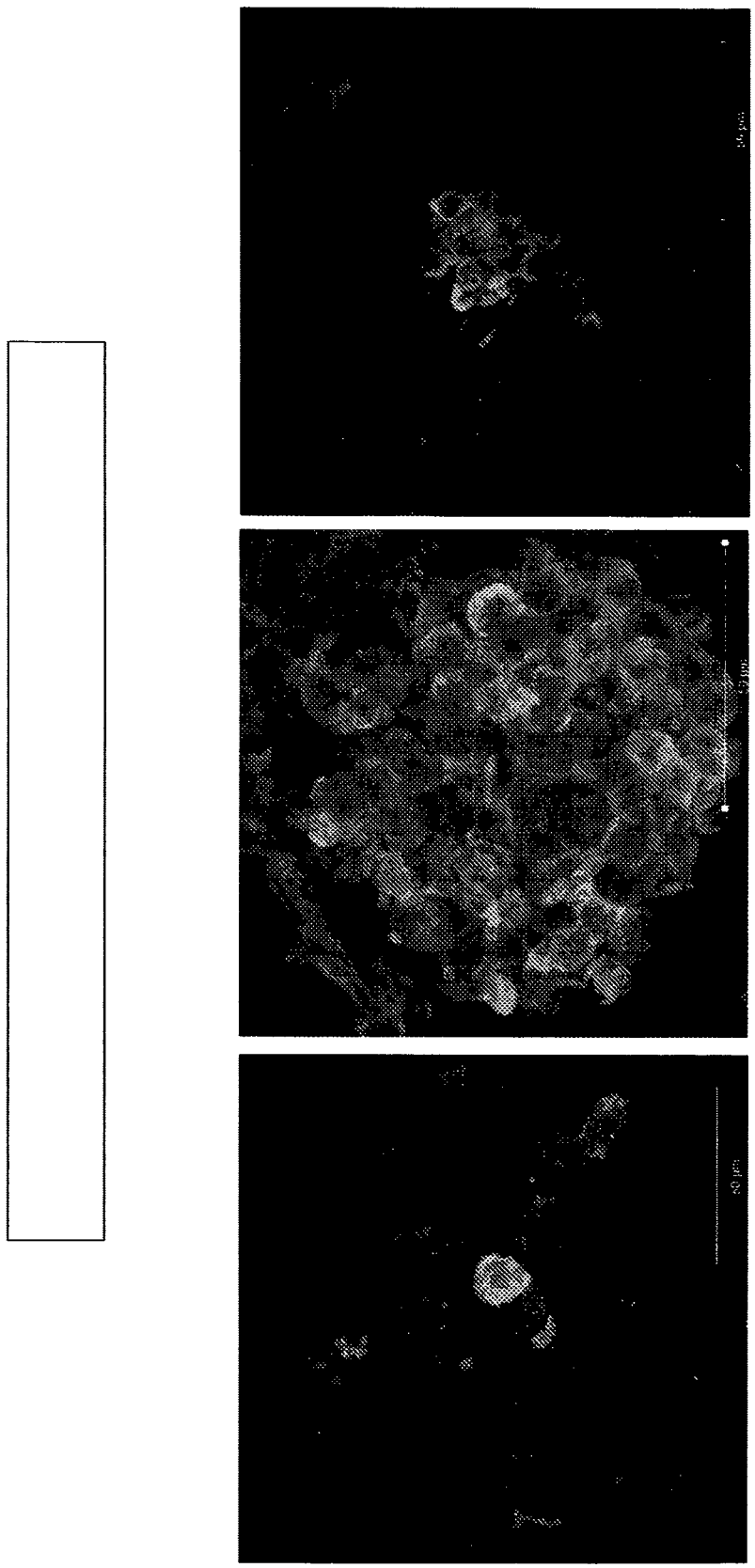
FIG. 28 is a series of photographs showing cluster formation after culture of single islets cells (mouse) on the control tissue culture plate (A) and on RGD-4RepCT (B). C: enlargements (63×) of insulin-positive clusters (bright; pointed to by arrows) in foam of 4RepCT (left), RGD-4RepCT (middle) and IKVAV-4RepCT (right) in close contact with the scaffold.

Long-term culture (over 2 weeks) of single cells was analyzed. Tissue-culture treated plastic served as control (FIG. 28A) and was compared to wells coated with film and foam of 4RepCT with incorporated cell-binding motifs, e.g. RGD (FIG. 28B). In all the different wells, single cells formed clusters of cells, as shown in FIG. 28. These clusters of cells differed in morphology, exhibiting scattered clusters e.g. in the control (FIG. 28A), and round clusters e.g. in 4RepCT with the RGD motif (FIG. 28B). The clusters were counted after two weeks and then saved for histological analysis, such as insulin staining. The results showed that the amount of round clusters found was enhanced in 4RepCT foam with RGD, and that these round clusters were insulin positive, as shown in FIG. 28C. These results indicate that 4RepCT can maintain islet beta cell function and enhance growth of round cell clusters that are insulin positive, compared to single cells cultured on normal cell-culture plastic.

C) Culturing of Beta Cells in Combination with Other Cells

Single mouse beta cells, human endothelial cells and human mesenchymal stem cells were plated alone or together and cultured on 4RepCT foam scaffolds with the incorporated motifs: none (wild-type; WT), RGD, RGE, IKVAV and YIGSR. The mesenchymal stem cells, when in culture alone, adhered to and grew along the structure of the scaffolds (FIG. 29).

Figure 30:
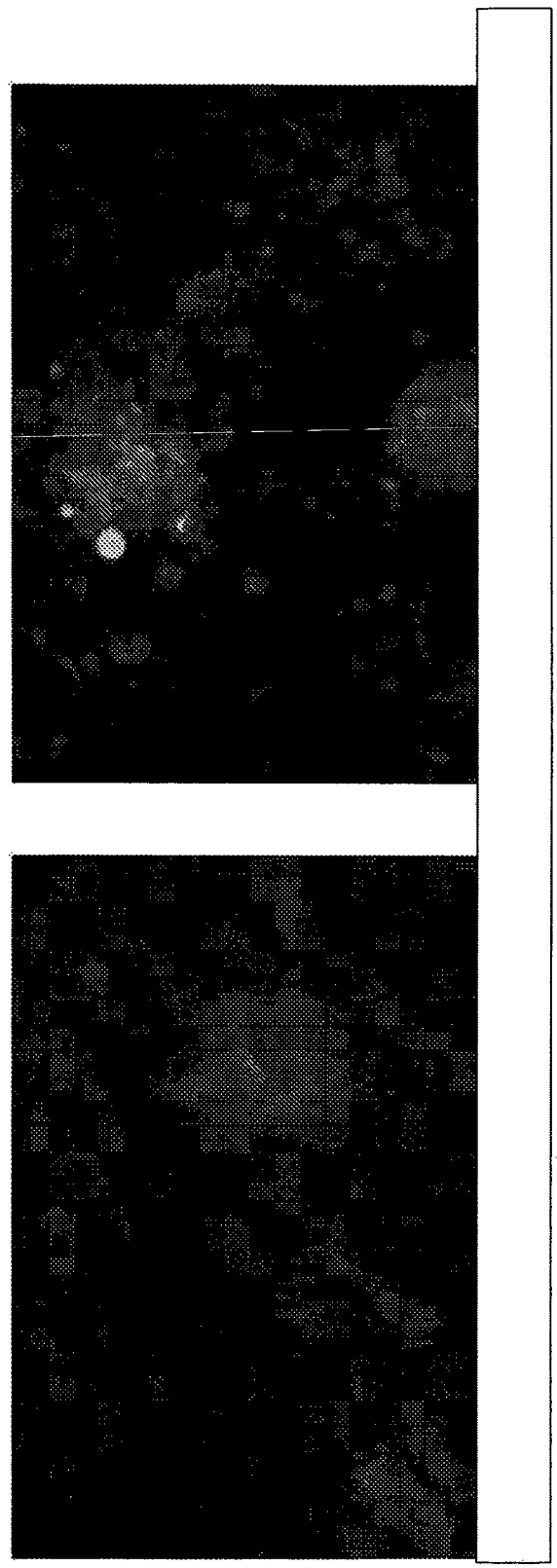
FIG. 30 is a pair of photographs showing co-culture of islet beta cells, endothelial cells and mesenchymal stem cells ("BEM") visualized by cell tracking dyes (beta cells:bright white; endothelial cells:light grey; mesenchymal cells:grey). The co-cultured BEMs form a cluster on 4RepCT foam. Clusters of BEM were found adhered to 4RepCT foam (left) and RGD-4RepCT foam (right, n=2, experiment done in duplicates).

Single beta cells, endothelial cells and mesenchymal stem cells grew on scaffolds of foam, and exhibited increased cluster formation on 4RepCT and RGD-4RepCT (FIG. 30).

Transplantation of 4RepCT scaffold in combination with islets of Langerhans or islet cells is expected to show engraftment support.

Conclusions

Culturing of islets with the various 4RepCT scaffolds (having different formats and peptide motifs) allowed basic research regarding the development of potential treatment strategies of diabetes at the cellular level.

Culturing of islets and islet single cells, such as beta cells, within a 4RepCT scaffold in different variants helps to maintain and increase their function in vitro.

Culturing of composite cell populations (comprising islet beta cells, endothelial cells and mesenchymal stem cells) within 4RepCT scaffolds has a potential as an insulin-making device if transplanted to a recipient using the recipients own endothelial cells and mesenchymal stem cells.

4RepCT with islets, transplanted together into the anterior chamber of the eye of a mouse using a technique recently developed at Prof Berggren's laboratory is expected to improve islet engraftment and survival. Transplantation of a 4RepCT scaffold in combination with islets of Langerhans or islet cells is expected to exhibit engraftment support.

The work described in this example accomplished the prerequisites for the development of a transplantable, artificial insulin-producing device based on a 4RepCT scaffold (with or without peptide motifs).

Example 6

Endothelial Cells on Recombinant Spider Silk

The growth of blood vessels is essential for tissue engineering in regenerative medicine. Endothelial cells are responsible for vessel growth, and this process is triggered during certain circumstances, such as wound healing. In the body, there are many different kinds of endothelial cells depending on organ and tissue. The endothelial cells that are in close contact with the tissue are known as microvascular endothelial cells.

Experimental Material

Commercially available, microvascular endothelial cells were obtained and maintained in culture according to the provider's instructions in a well-known manner.

Cell scaffold material comprising polymers of different variants of the 4RepCT protein was prepared into different physical forms as described in Example 1. The 4RepCT protein was used in unmodified, "wild-type" form without any additional cell-binding motif, as well as modified with the peptidic cell-binding motifs RGD, IKVAV or YIGSR.

Experimental Methods

Cells were added to the different scaffold materials and studied. A variety of assays were carried out on the cells, including a proliferation assay and a BD Pathway analysis (BD Biosciences). It is also possible to carry out for example cell function analysis, Live/Dead assay of apoptosis and necrosis, and histology analysis. Tissue-culture treated plastic plates were used as control.

Results

Figure 31:
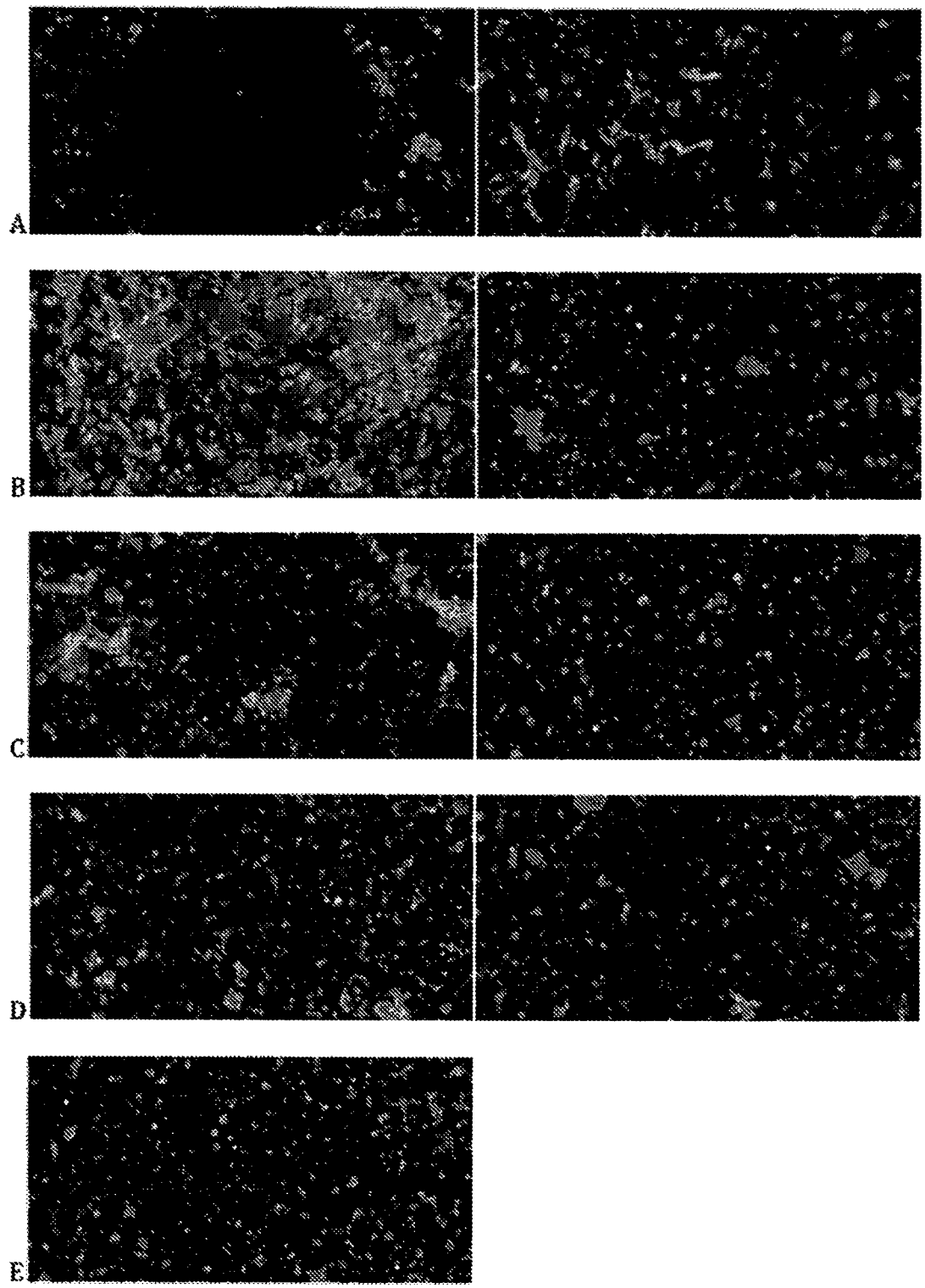
FIGS. 31A-E are photographs showing cultured endothelial cells on different 4RepCT scaffolds in the form of film or foam with different cell-binding motifs, and control plates (cell culture glass); A: film, left panel 4RepCT (wild-type), right panel RGD-4RepCT; B: film, left panel IKVAV-4RepCT, right panel YIGSR-4RepCT; C: foam, left panel 4RepCT (wild-type), right panel RGD-4RepCT; D: foam, left panel IKVAV-4RepCT, right panel YIGSR-4RepCT; E: control.
Figure 32:
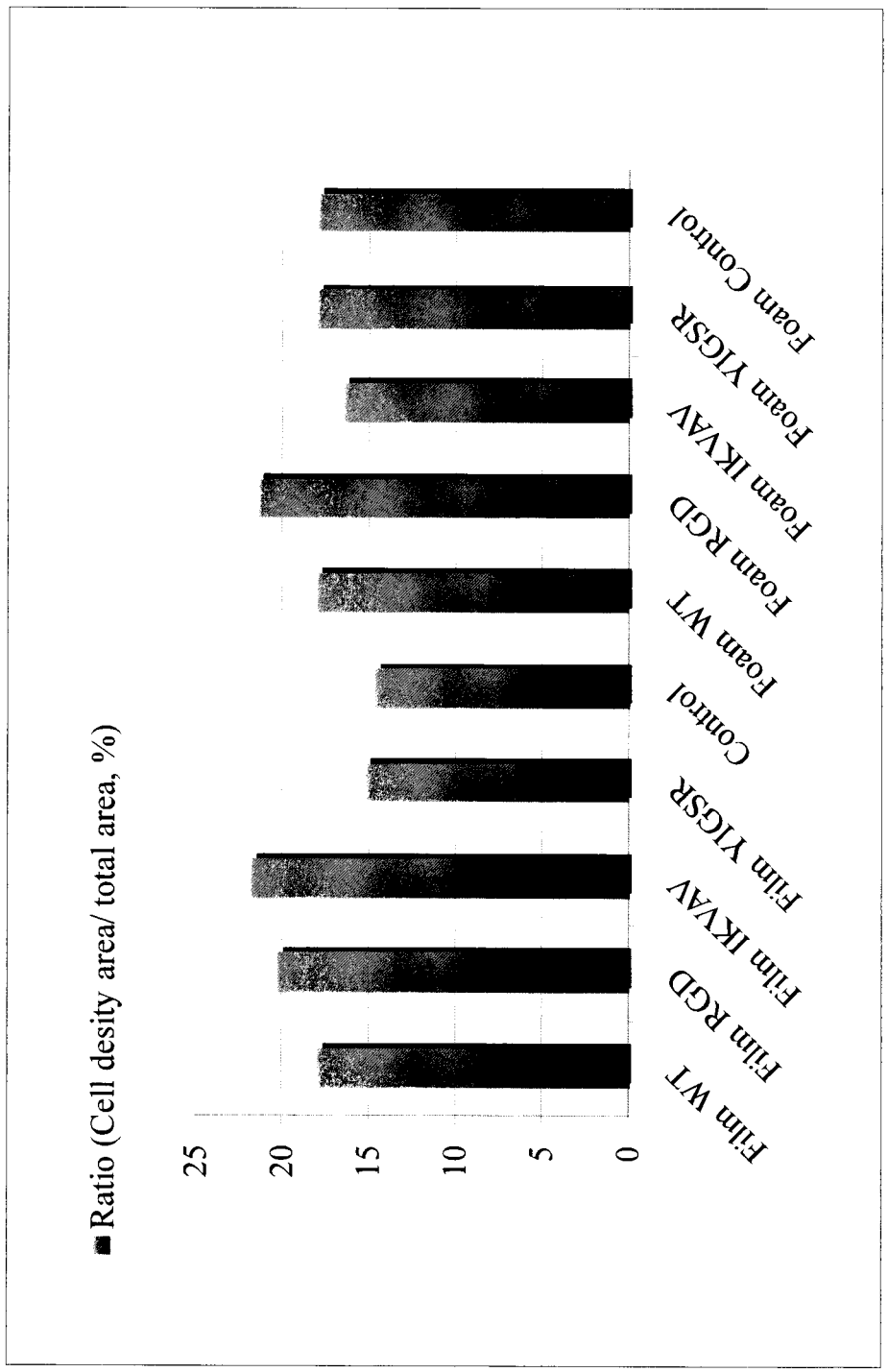
FIG. 32 is a diagram showing the endothelial cell density ratio of total area analyzed within a 96-well culture plate coated with different 4RepCT scaffolds with different cell-binding motifs as indicated.

Results are presented in FIGS. 31 and 32. Endothelial cells adhered and grew in culture together with the different 4RepCT scaffolds. After 3 days of culture, their morphology was analyzed and the amounts of cells were counted. The morphological analysis showed that endothelial cells on 4RepCT scaffolds in different physical forms, with and without cell-binding motifs, adhered and were viable (FIGS. 31 and 32).

Conclusions

Endothelial cells were viable and could grow on 4RepCT scaffolds, as well as showing a proliferative capacity thereon.

Example 7

Fibroblasts on Recombinant Spider Silk

Experiments were done showing that scaffolds prepared from 4RepCT support the growth of anchorage dependent primary fibroblasts, that the cells survive, attach to the material and maintain one of their main functions, i.e. to secrete collagen type I. 4RepCT scaffolds show increased capacity to support cell growth compared to tissue culture treated plastics. Introducing the integrin binding motif RGD further improves this cell supportive capacity. Both growth on wild-type 4RepCT and RGD-4RepCT was shown to be independent of serum proteins.

Materials and Methods

Cell Culture

Primary human dermal fibroblasts of neonatal origin, HDFn (ECACC/HPA) were cultured in Dulbecco's modified Eagle's medium nutrient mixture F12 HAM (Sigma) supplemented with 5% foetal bovine serum (Gibco), penicillin and streptomycin (National Veterinary Institute, SVA, Sweden) (FIGS. 34-36 and 38-41). In parallel experiments, (FIGS. 37 and 42), primary human fibroblasts (SF-HDF, PromoCell) were cultured in serum-free cell culture medium PC-1 (Lonza, Belgium) supplemented with 25 µg/ml ascorbic acid (Sigma), and 5 mM L-glutamine (SVA). Cells were seeded onto 4RepCT scaffolds at the densities 3000 cells/cm$^2$ or 15000 cells/cm$^2$. All experiments were performed in passage 8 (with the exception of FIGS. 36 and 41, which were performed in passage 4) at 37° C. with 5% $CO_2$ and 95% humidity.

Cell Culture Scaffolds

After purification, recombinantly expressed 4RepCT (Hedhammar et al (2008), supra) with and without additional N-terminal cell binding motifs RGD, IKVAV and YIGSR, or the tripeptide RGE, was concentrated by centrifugal filtration (Amicon Ultra, Millipore) and sterile filtered (0.22 µm) before preparation of scaffolds in accordance with the description in Example 1. Likewise, recombinant NT4RepCTHis was prepared. Fibers were sterilized through autoclaving for 15 minutes at 121° C. in distilled water, 2.8 bar. Scaffolds were prepared in hydrophobic 96-well cell culture plates (Sarstedt) or cell culture chamber glass slides (LabTek). Wells without scaffolds were used as negative control (HP), and tissue culture treated plates as a positive control (TCT).

The plates and chamber slides were allowed to dry over night at room temperature under sterile conditions with full speed fan. Scaffolds were washed twice with sterile PBS and pre-incubated with complete cell culture medium 1 h at 37° C. with 5% $CO_2$ before cell seeding.

Enumeration of Cells with Alamar Blue

Cell growth on 96-well plate scaffolds was monitored with Alamar Blue cell viability assay (Molecular Probes) every second day during the culture period. After 4 h incubation with Alamar blue diluted 1:10 in cell culture medium, fluorescence intensity at excitation 544/emission 595 was measured in 100 µl supernatants from the cultures with a fluorescence plate reader (FarCyte, TECAN). A standard curve ranging from 50-64000 cells/well was established to enable recalculation of fluorescence intensity to cell numbers (live cells). Each scaffold type was analyzed in hexaplicate.

Cellular Stainings

Cells cultured on scaffolds in chamber slides were stained for either viable/dead cells, filamentous actin or collagen type I every third day during the culture period. The stainings were viewed under a confocal microscope (Leica), green fluorescence: excitation at 488 nm/detection at 500-530 nm, red fluorescence: excitation at 543 nm/detection at 620-660), and pictures were taken with Leica confocal software (LCS).

Live/Dead Staining:

Live/dead viability assay (Molecular Probes) was used to visualize living and dead cells growing on scaffolds. The cultures were washed twice with pre-warmed phosphate buffered saline (PBS) and stained with Calcein-AM and ethidium homodimer-1 (EthD-1) for 30 minutes at room temperature.

Filamentous Actin:

Scaffolds were washed twice and cells were fixed with 4% paraformaldehyde, permeabilized with 0.1% Triton X-100 in PBS, and blocked with 1% bovine serum albumin (BSA, AppliChem) in PBS, before staining with ALEXA FLUOR™488-Phalloidin (Invitrogen), 1:40 in 1% BSA in PBS. EthD-1 was used as nuclear staining. Slides were mounted in Fluorescence mounting medium (Dako, Copenhagen).

Vinculin:

Scaffolds were washed twice and cells were fixed with 4% paraformaldehyde, permeabilized with 0.1% Triton X-100 in PBS, and blocked with 1% bovine serum albumin (BSA, AppliChem) in PBS, before staining with mouse anti human vinculin (Sigma V9131) at 9.5 µg/ml in 1% BSA, followed by ALEXA FLUOR™488 goat anti mouse IgG (H+L), cross adsorbed (Invitrogen) and ALEXA FLUOR™594-Phalloidin (Invitrogen), 1:40 in 1% BSA in PBS. DAPI was used as nuclear staining. Slides were mounted in Fluorescence mounting medium (Dako, Copenhagen).

Collagen Type I:

Scaffolds were washed twice and cells were fixed with acetone at −20° C. and blocked with 1% BSA in PBS before staining with mouse anti collagen type I (clone COL-1, Sigma-Aldrich) at 3.5 µg/ml in 1% BSA, followed by ALEXA FLUOR™488 goat anti mouse IgG (H+L), cross adsorbed (Invitrogen). EthD-1 was used as nuclear staining. Slides were mounted in Fluorescence mounting medium. Mouse IgG1 (clone B-Z1, BioSite) was used as Isotype control.

Quantitative Determination of Secreted Collagen Type I

Supernatants were collected from cultures every second day, diluted 1:10 and analysed for C-peptide, which is cleaved off from the procollagen type I molecule during its secretion into the cell culture medium, using the Procollagen Type I C-Peptide EIA Kit (TAKARA) according to the instructions from the manufacturer. $OD_{450}$ was measured with Sunrise plate reader (TECAN), and data management with MAGEL-LAN™ software was used to achieve the concentration on C-peptide in the original samples. Data was recalculated to pg C-peptide secreted/cell.

Results

Cell Culture Scaffolds Prepared from 4RepCT

Figure 33:
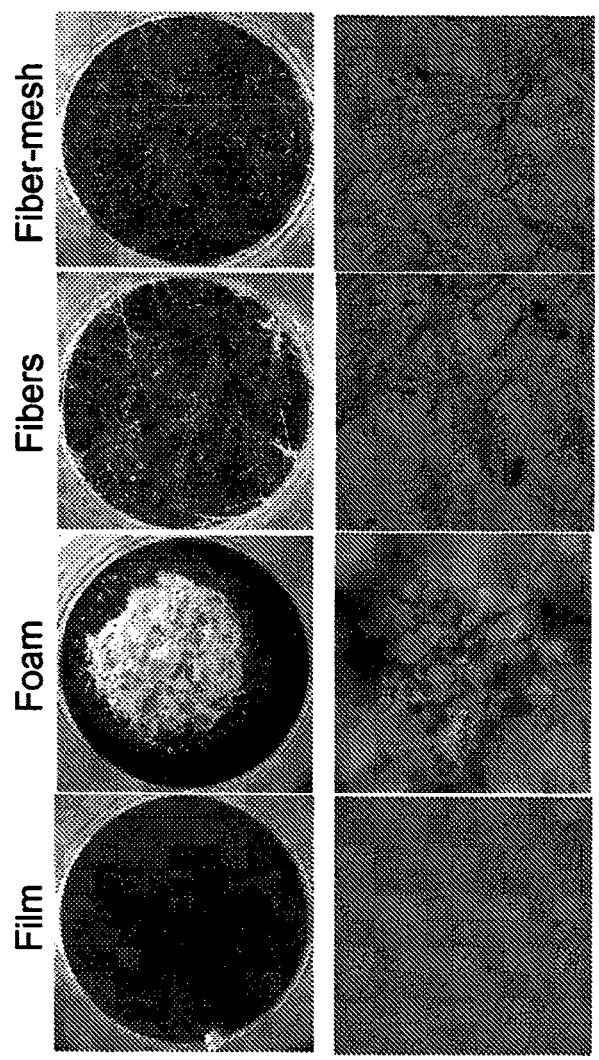
FIG. 33 is a series of photographs of cell scaffold materials prepared from 4RepCT. The upper panel shows wells in 96-well plate at approx 25× magnification. The lower panel shows scaffolds viewed in an inverted light microscope at 200× magnification.

Film, foam, fiber and fiber-mesh scaffolds were successfully prepared from 4RepCT protein solution (FIG. 33).

Growth of Fibroblasts on 4RepCT Scaffolds

Figure 34:
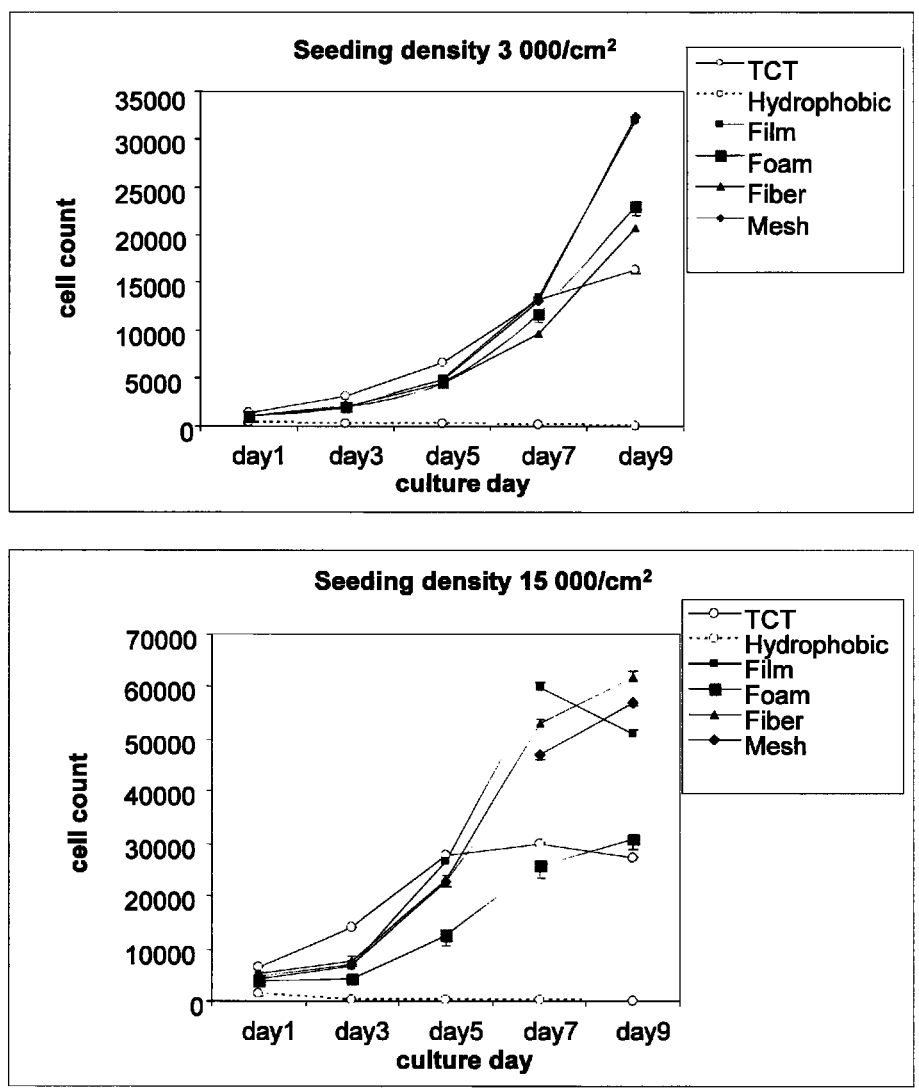
FIGS. 34 and 35 show diagrams of fibroblast growth on 4RepCT scaffolds and controls as indicated, measured with Alamar blue viability assay. Error bars show standard deviation of hexaplicates.
Figure 35:
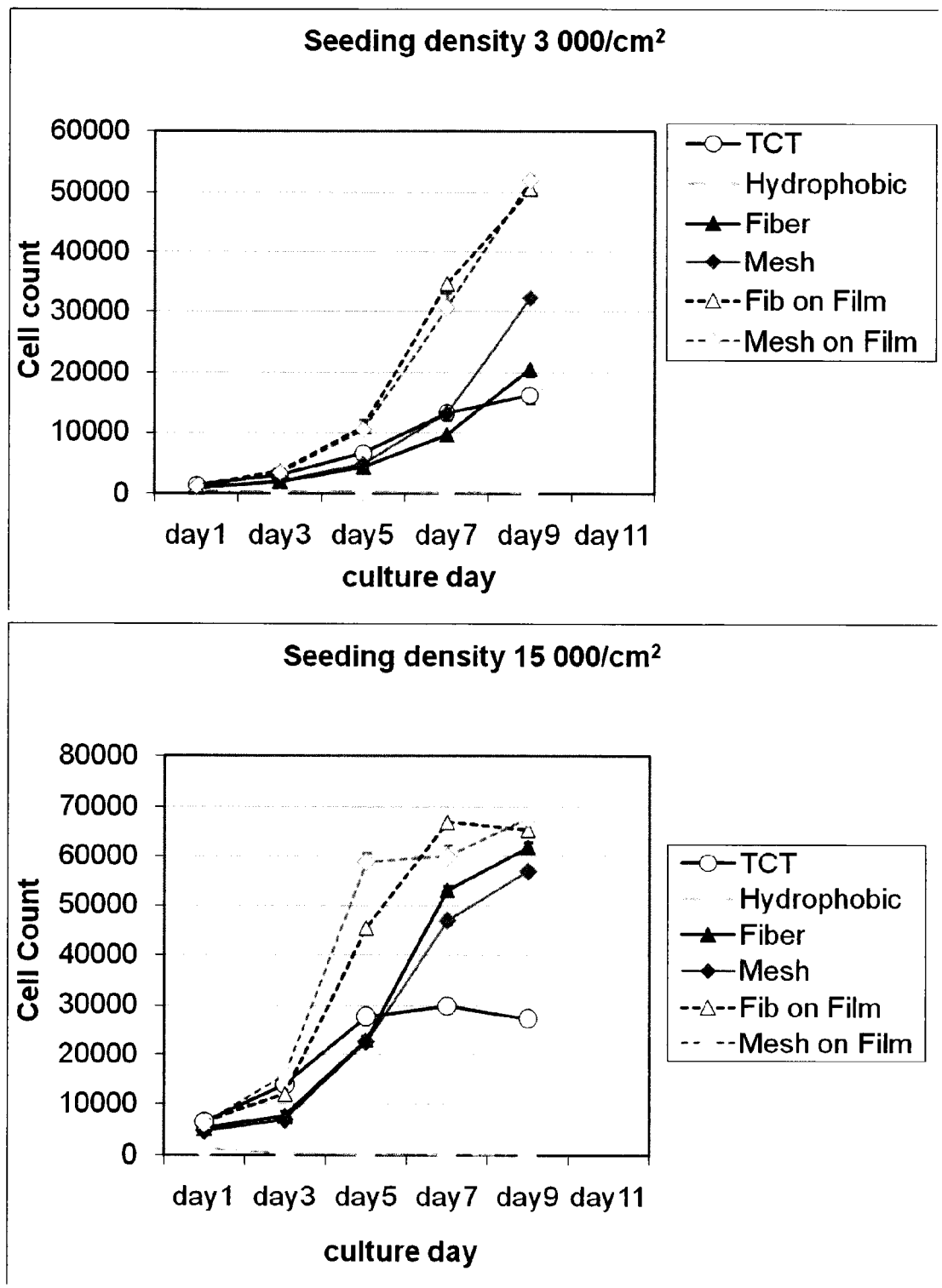

4RepCT scaffolds showed an increased capacity to support growth and expansion of primary fibroblasts compared to the TCT, as shown by the higher number of live cells present in scaffold wells after the initial phase of culture (i.e. from day 7 at the lower seeding density and from day 5 at the higher seeding density, FIG. 34). In the initial phase, however, the cells seem to grow somewhat slower on the scaffolds compared to the TCT. The number of living cells on the foam scaffolds is consistently lower than film and fiber-based scaffolds. However, the accessible scaffold area of the foam scaffolds is difficult to estimate, thus direct comparison to the other scaffold formats is not possible. By adding 4RepCT film under the fiber or fiber-mesh scaffolds, the supportive capacity increased even more (FIG. 35).

Figure 36:
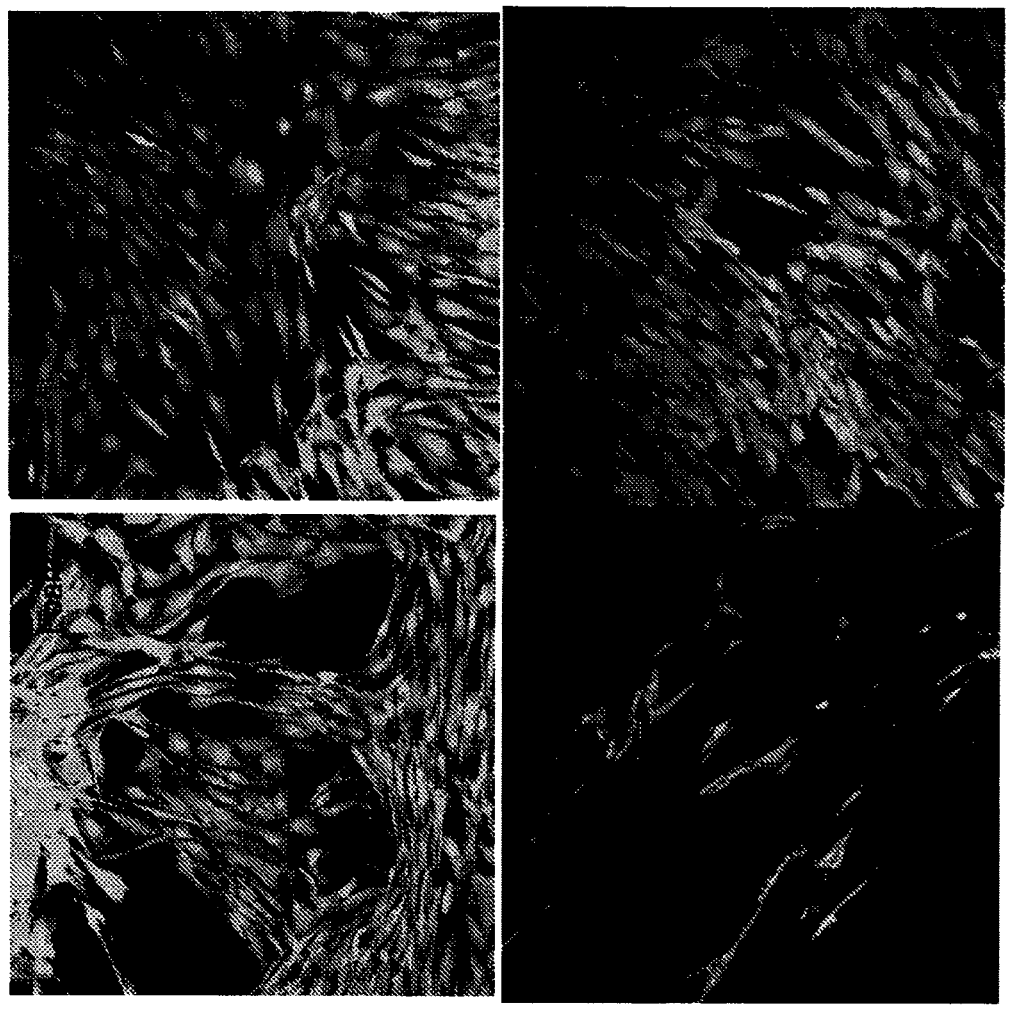
FIG. 36 is a series of photographs of HDFn cultured 4 days on 4RepCT scaffolds and control as indicated, at a seeding density of 15000 cells/cm$^2$, and stained with Live/dead for detection of living and dead cells.

We also demonstrated that the fibroblasts exhibited high live/dead ratios on the scaffolds, where film scaffolds showed close to identical growth pattern, cell density and live/dead ratios to cell culture treated glass slides (FIG. 36, right panels). Since the foam and fiber-based scaffolds stained red in this assay, we were able to see that the shape of living cells followed the morphology of the material.

Serum-Free Culture of Human Fibroblasts on 4RepCT Scaffolds

Figure 37:
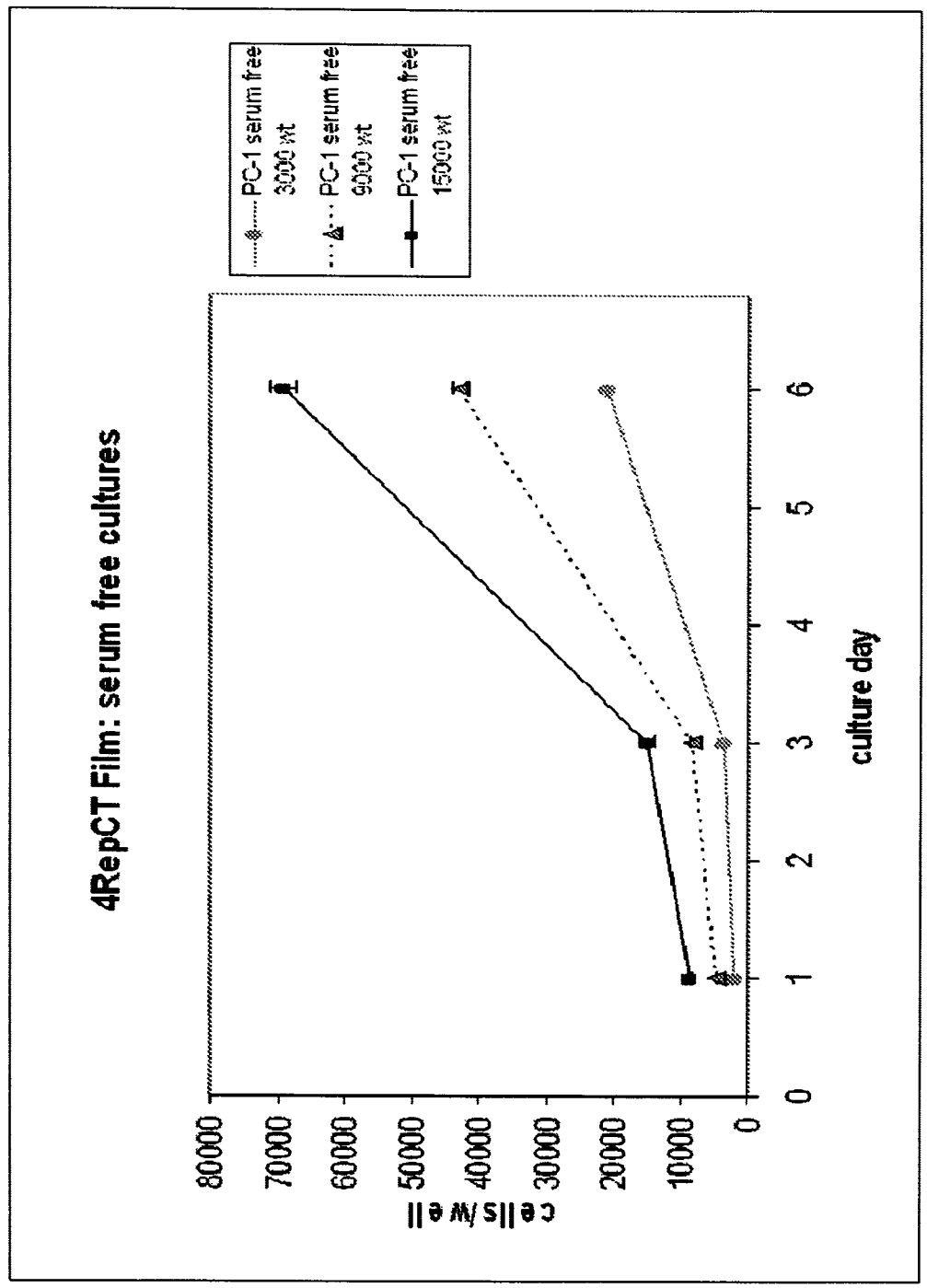
FIG. 37 shows a diagram of SF-HDF growth on 4RepCT film under serum-free conditions. The seeding densities (cells/cm$^2$) were as indicated. After day 6, the number of cells continued to increase, thereby exceeding the highest standard and preventing recalculation of data for plotting. The number of viable cells was measured with Alamar blue. Error bars show standard deviation of hexaplicates.
Figure 38:
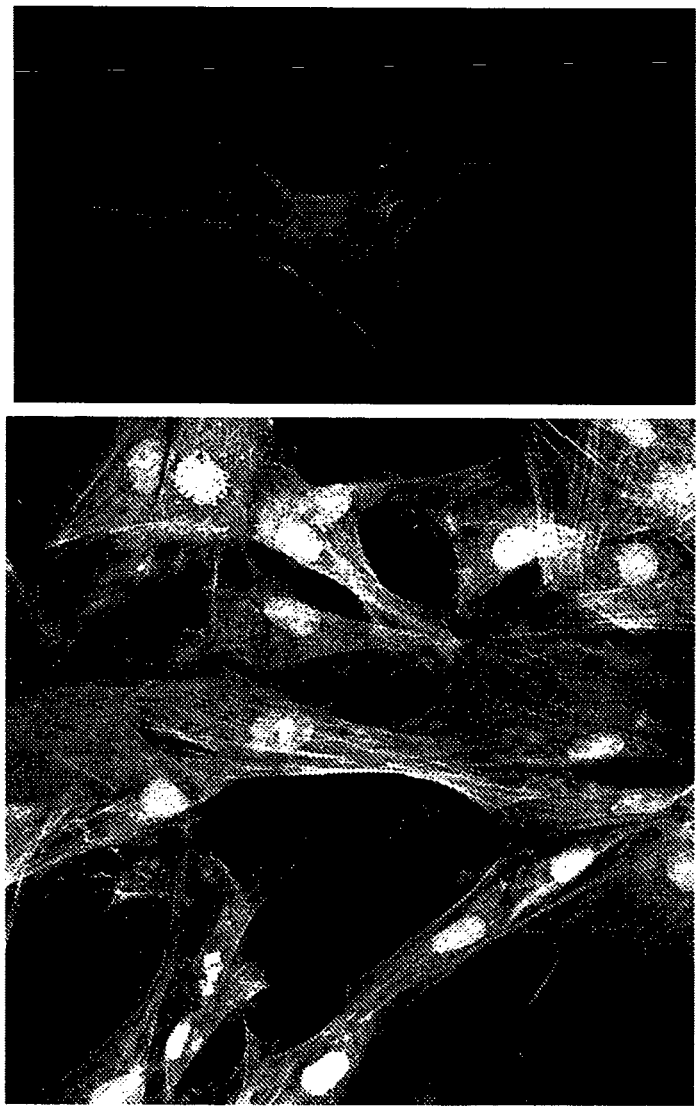
FIG. 38 shows photographs of HDFn attaching to 4RepCT fiber (left panel) and film (right panel) as visualized by staining filamentous actin green with ALEXA FLUOR™488-Phallodin (appears as grey strands in photos). Nuclei were stained red (appears as bright white) with EthD-1.

We have also shown that SF-HDFs (primary human fibroblasts expanded under serum-free conditions) are able to grow on 4RepCT film scaffolds with no serum present in the cultures (FIG. 37). This proves that the interaction of cells with the material is not dependent on serum proteins that have bound non-specifically to the surface, but that the scaffolds themselves present a hospitable surface for the cells to grow on.

Attachment of Cells to Scaffolds

Figure 43:
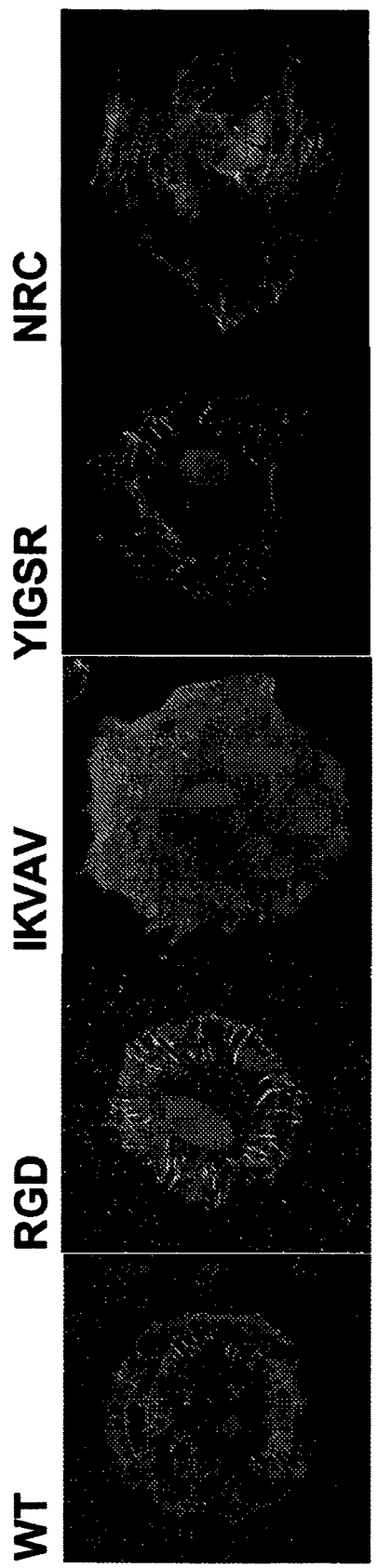
FIG. 43 is a series of photographs showing fibroblasts grown on 4RepCT film with various cell binding motifs as indicated. Fibroblasts exhibit focal adhesions on all film variants after only 3 h, indicating integrin-mediated adhesion to the material. The focal adhesions appear as bright elongated spots. The cells are cultured without any serum added. WT: 4RepCT; NRC: NT4RepCTHis.

During attachment of cells to the surrounding matrix, filamentous actin is linked to the membrane-bound receptors that mediate the binding. By staining intracellular filamentous actin, the binding points between cells and the underlying material can be indirectly visualized. With this method, we have been able to demonstrate that the HDFn actually binds to fiber (FIG. 38, left panel), fiber-mesh, film (FIG. 38, right panel) and foam scaffolds both during early and late culture (day 1, 4, 7, 10). Furthermore, through staining for vinculin in combination with filamentous actin, focal adhesions could be detected after 3 h culture of SF-HDF on wild-type (WT) film, RGD, IKVAV, YIGSR and NRC (NT4RepCTHis), (FIG. 43), under serum free conditions. These results indicate integrin-mediated adhesion to the different substrates.

Collagen Type I Secretion by Cells Growing on 4RepCT Scaffolds

Figure 39A:
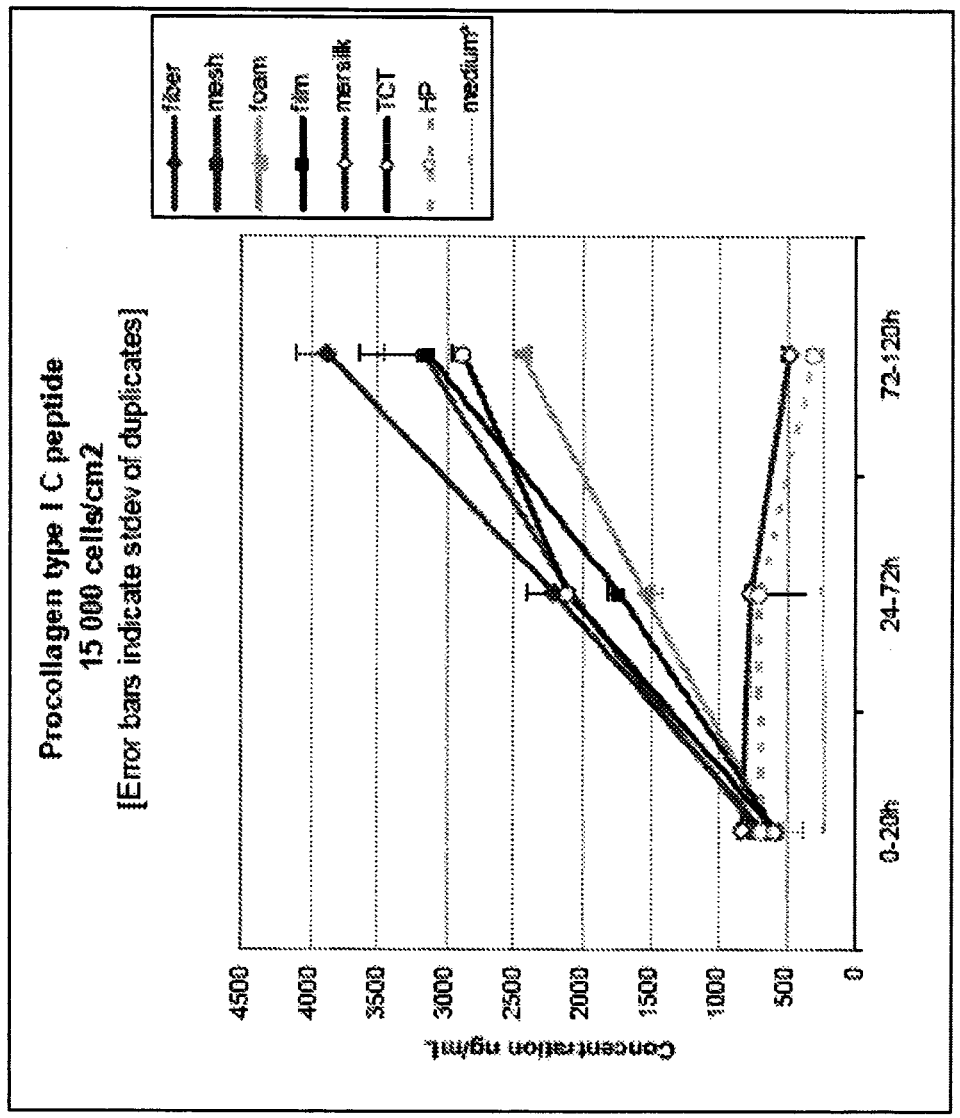
Figure 39B:
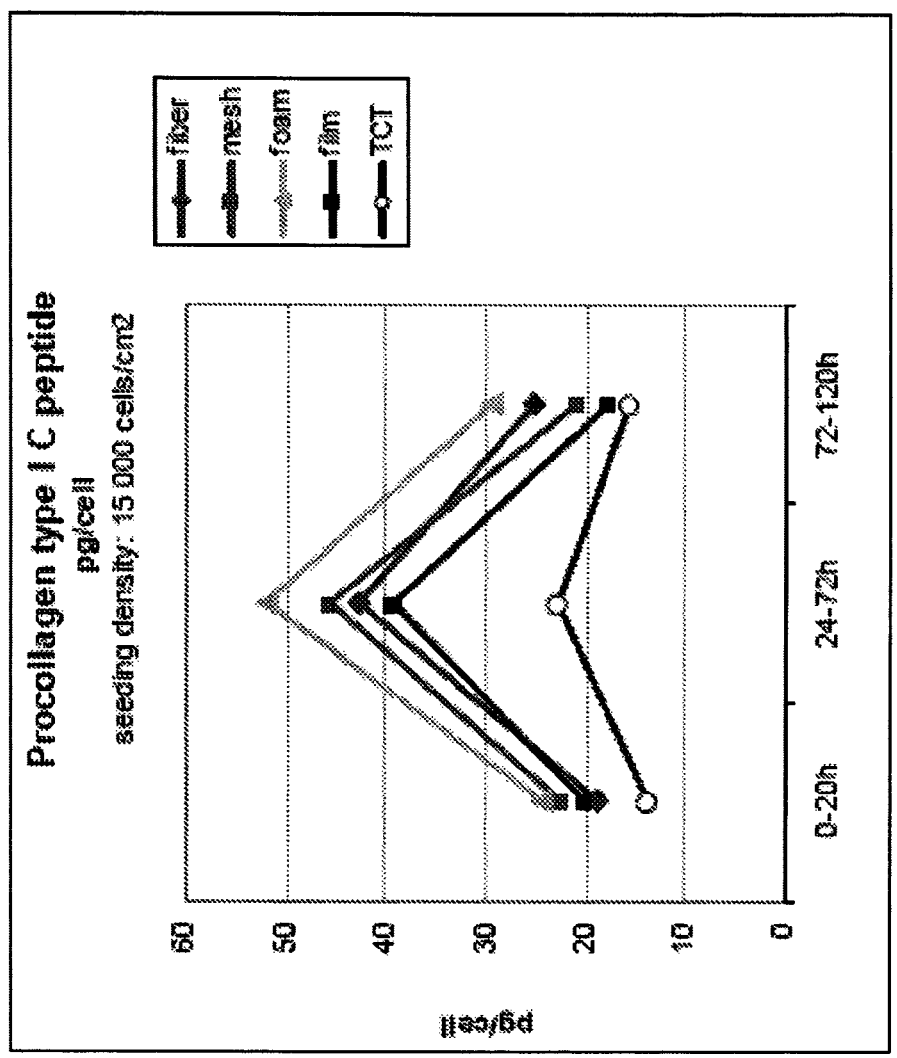
Figure 40:
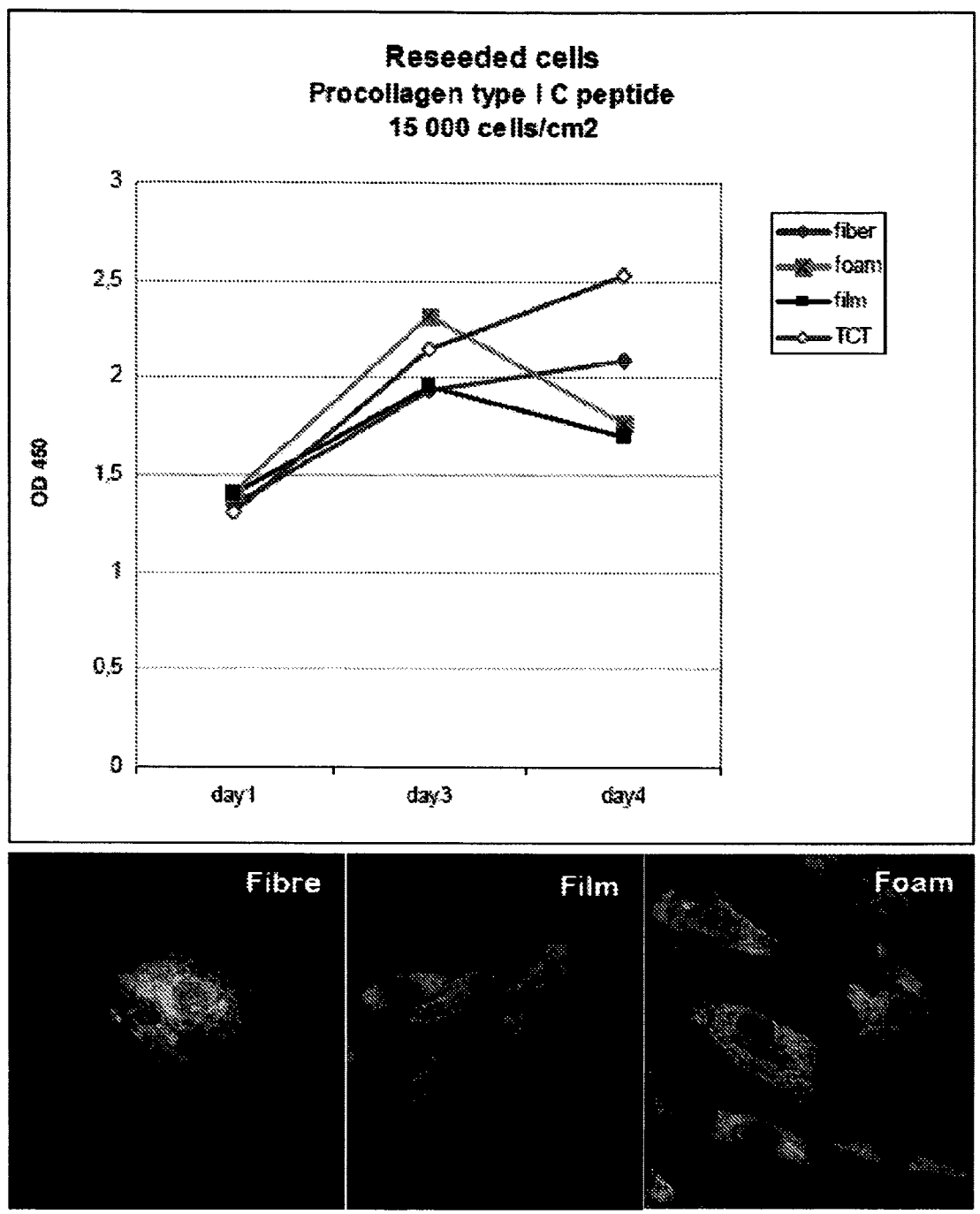
FIG. 40 shows the production and secretion of collagen by fibroblasts cultured on different 4RepCT scaffolds as indicated for 14 days and then reseeded onto tissue culture treated (TCT) plates or chamber slides for analysis of procollagen type I C peptide (upper panel) and intracellular collagen type I production (lower panel) respectively.

The cells produced collagen type I when growing on all the different formats of 4RepCT, i.e. film, foam, fiber and fiber-mesh scaffolds. Thus, the cells maintain one of their important functions during culture in vitro on the 4RepCT scaffold material. The levels of secreted collagen (as measured by the C-peptide cleaved off during secretion) increased in the culture medium during the first 5 days of culture (FIG. 39, left upper panel). However, the amount of collagen produced per cell reached a maximum at 24-72 h post seeding, and was at this time point higher for cells growing on any of the 4RepCT scaffolds compared to the TCT (FIG. 39, right upper panel). Intracellular production of collagen was demonstrated to a similar extent on all scaffold types at day 1, 4, 7 and 10 post seeding (examples shown in FIG. 39, lower panel).

Maintained Fibroblast Phenotype after Culture on 4RepCT Scaffolds

To verify that fibroblasts maintained their phenotype after culture on 4RepCT scaffolds, cells were harvested from scaffolds after 14 days culture and reseeded onto either TCT for evaluation of collagen type I secretion, or onto glass for intracellular staining of collagen type I. Bo doing this it was demonstrated that the fibroblasts still produce (FIG. 40, lower panel) and secrete (FIG. 40, upper panel) collagen type I, and thereby do not lose what is one of their most important functions even after a relatively long-term culture on 4RepCT scaffolds.

Fibroblasts Grown on Functionalized 4RepCT Scaffolds

Figure 41A:
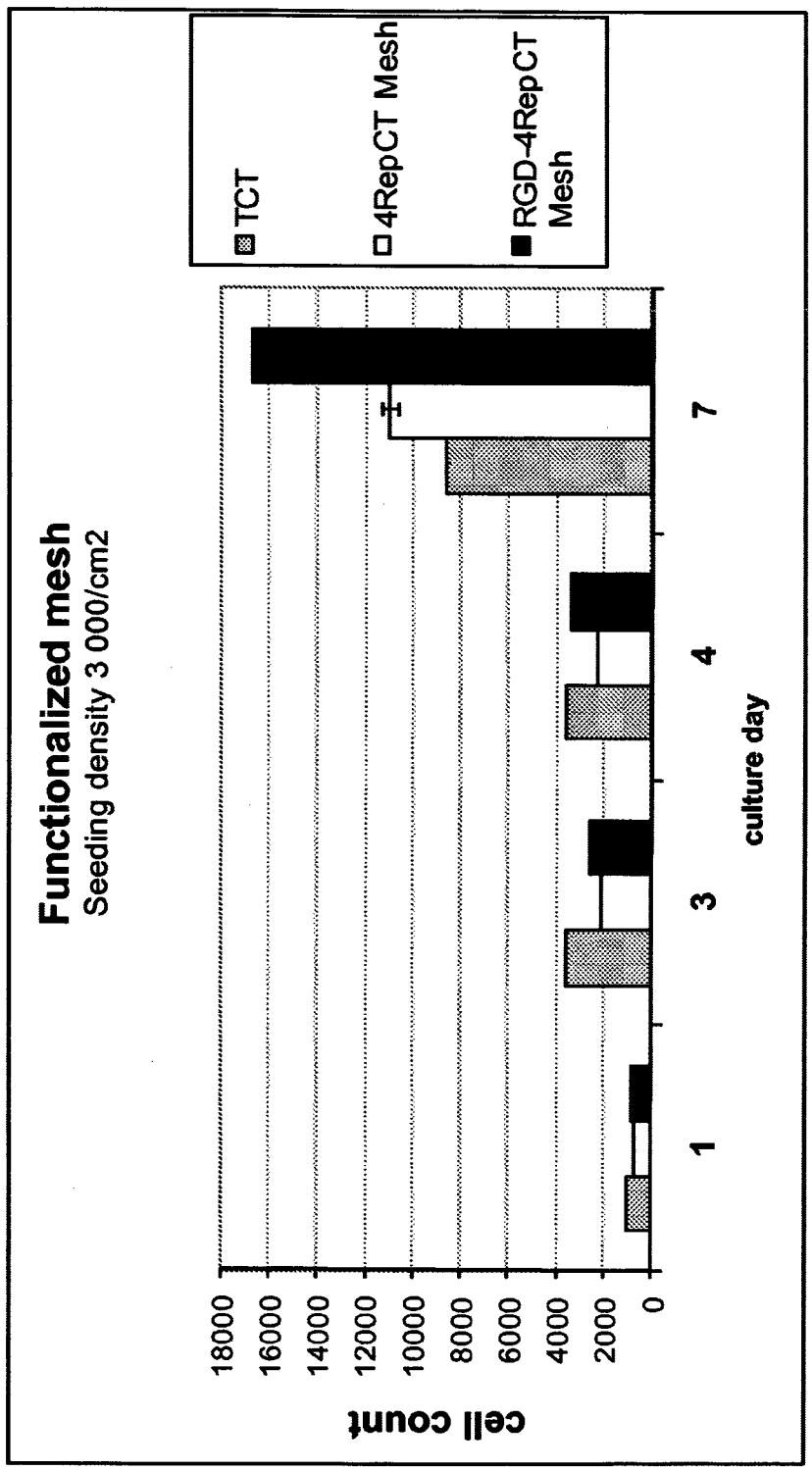
Figure 42:
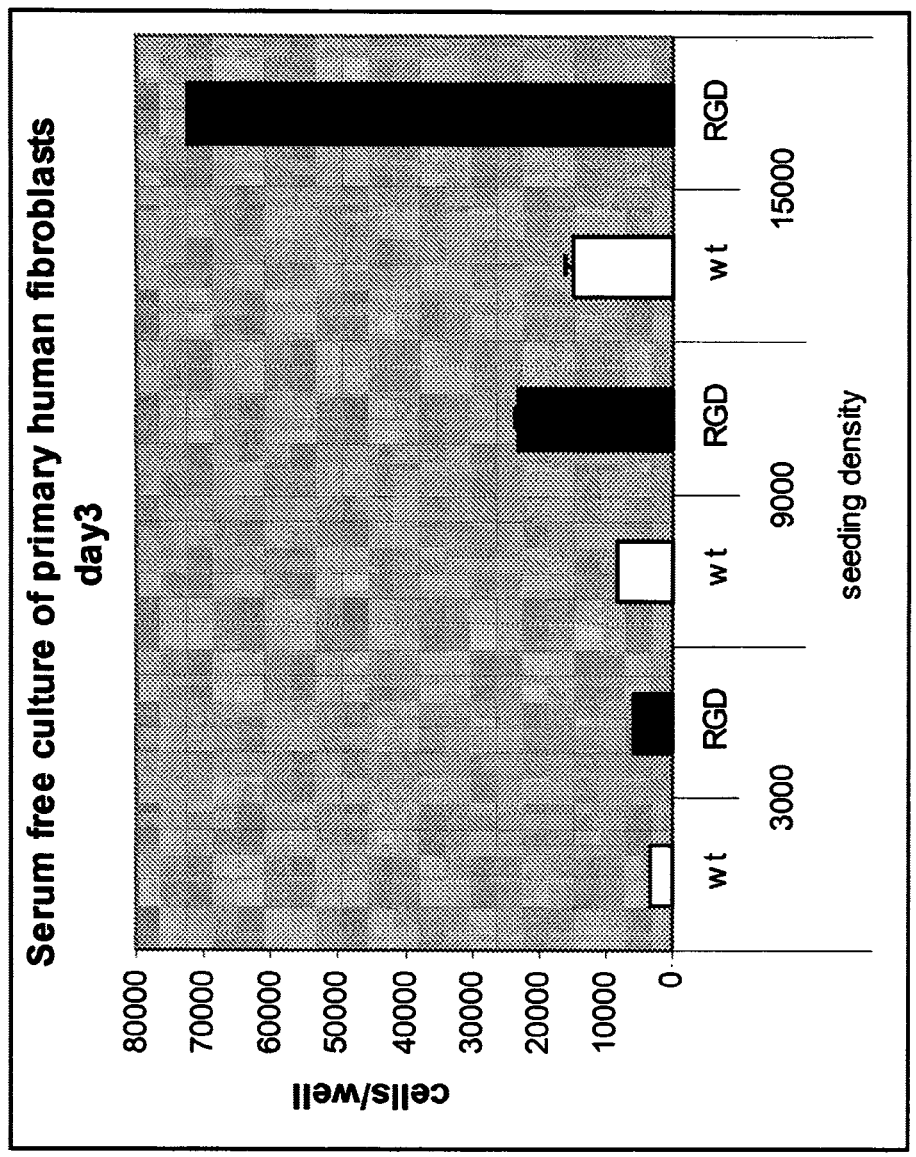
FIG. 42 is a diagram showing the number of SF-HDF growing on wild-type 4RepCT (wt, open bars) or RGD-4RepCT (filled bars) film at day 3. Seeding densities are given in cells/cm$^2$. The number of viable cells is measured with Alamar blue. Error bars show standard deviation of hexaplicates.

Preliminary data from Alamar blue viability experiments show that the introduction of RGD into 4RepCT increases the total number of living cells growing on the film and fiber-mesh scaffolds from day 3 and 1 respectively (FIG. 41). Over time, the number of cells also exceeds the cell counts present in TCT wells, i.e. from day 7. In a parallel set up, a serum free cell culture system were used, showing that even in the absence of serum, enhanced growth of primary fibroblasts was achieved on the RGD-4RepCT film, compared to 4RepCT without RGD (FIG. 42). Thus, introduction of RGD can improve the capacity of the scaffolds to support the growth of anchorage dependent cells markedly, and the effect is not dependent on serum components present in the cell culture medium. The results also indicate that the RGD motifs are properly exposed on the surface of the scaffolds.

Example 8

Keratinocytes on Recombinant Spider Silk

Experiments were performed to show that film scaffolds prepared from 4RepCT support the growth of primary keratinocytes, and that the cells adhere to the material and maintain their characteristic morphology. Both growth on wild-type 4RepCT and functionalized 4RepCT was shown to be independent of serum proteins.

Materials and Methods

Keratinocytes isolated from human skin were cultured in Keratinocyte SFM with supplement (Gibco), which is a serum-free set-up designed for the growth of keratinocytes. Traditionally, 10% fetal bovine serum is added to inactivate trypsin after harvesting the cells, to ensure binding upon re-seeding. In the current set-up, parallel experiments with and without this serum addition were performed. Keratinocytes were seeded at passage 4 (10000 cells/cm$^2$) onto wild type and functionalized film scaffolds of 4RepCT as described in previous Examples. Functionalizations that were tested included the general cell-binding motifs RGD and IKVAV, but could also have included the general cell-binding motif YIGSR and/or the keratinocyte-specific motifs EPDIM and NKDIL. Keratinocyte-specific markers may furthermore be used to ensure maintained phenotype at the end of culture, and to determine differentiation status, e.g. keratin (K1, K5, K10, K6/K16/K17), filaggrin, Tob, G6K12, gp80 and MRP-8.

Figure 44:
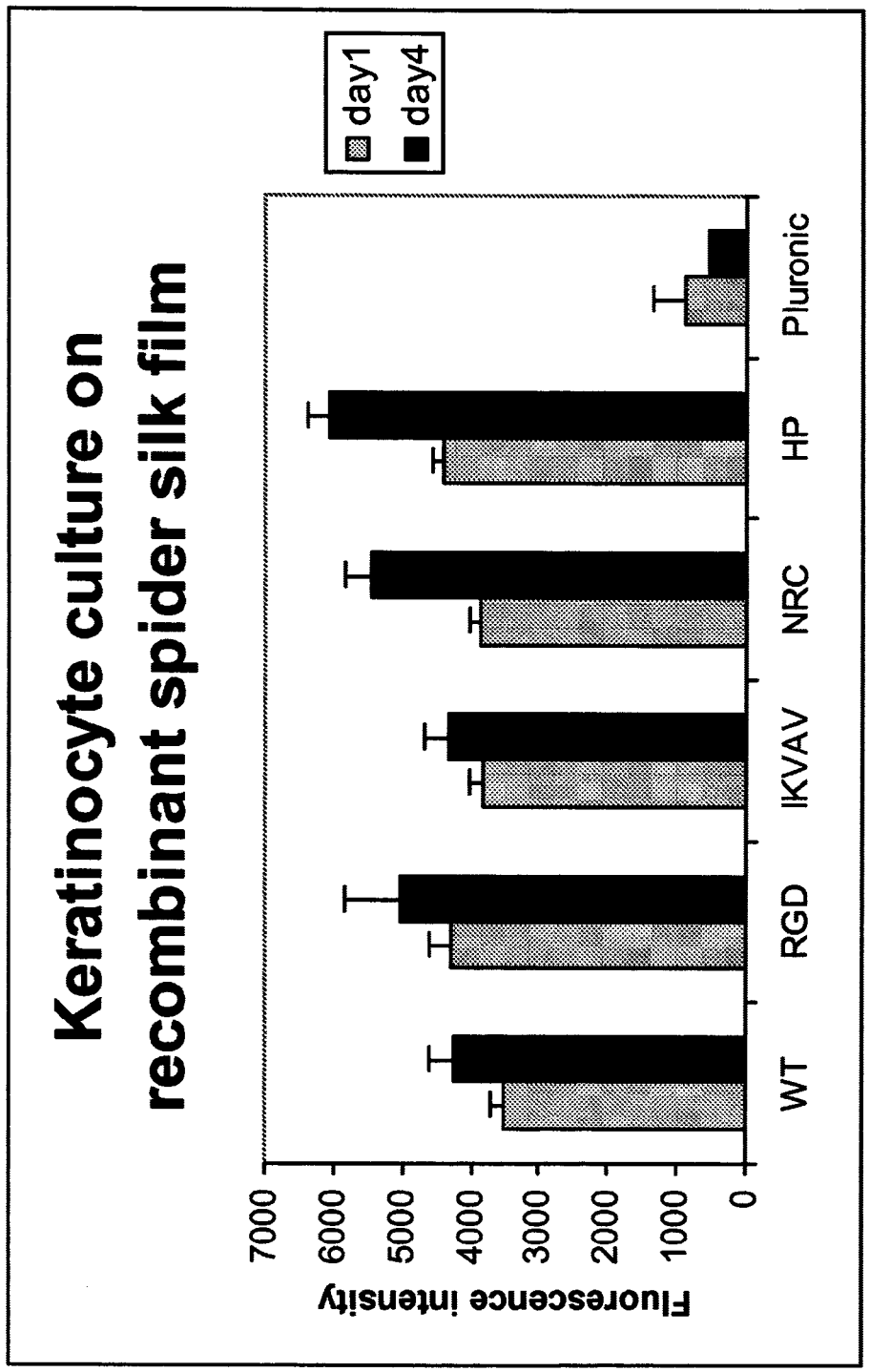
FIG. 44 is a diagram showing growth of human primary keratinocytes on 4RepCT film with or without different cell binding motifs as indicated, and on NT4RepCTHis (NRC). Controls used were untreated cell plastic (HP) and Pluronic-coated cell plastic (to prevent adhesion). Live cells were detected with Alamar blue at day 1 and day 4 after seeding.
Figure 45:
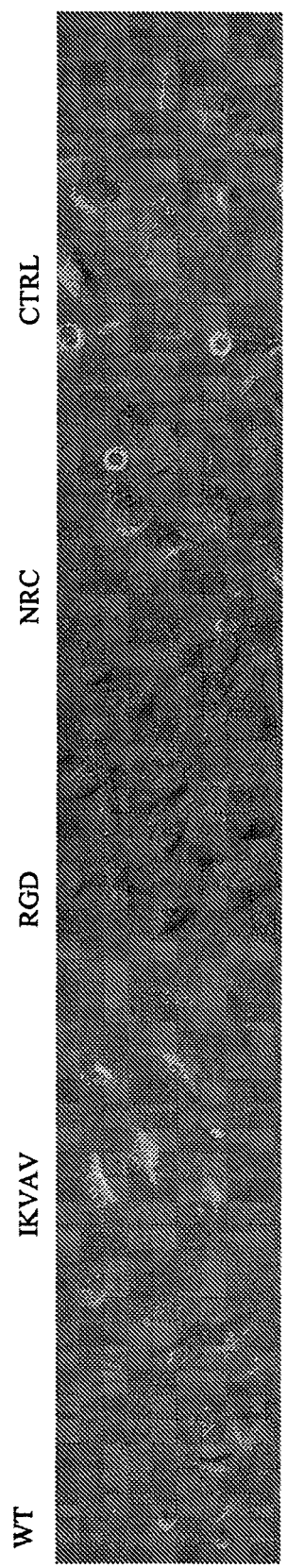
FIG. 45 is a series of photographs showing human primary keratinocytes in passage 4 after 3 days of culture on 4RepCT film with various cell binding motifs as indicated. WT: 4RepCT; NRC: NT4RepCTHis; CTRL: cell culture glass.
Figure 46:
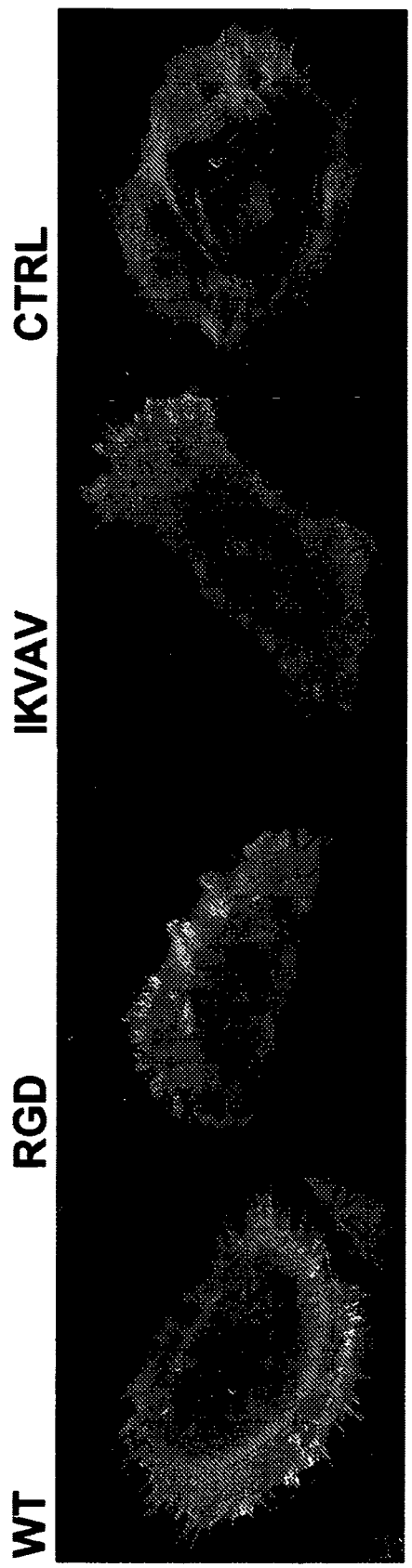
FIG. 46 is a series of photographs showing keratinocytes on day 4 after seeding on the indicated material. Cells were stained for vinculin to visualize focal adhesions, which are shown as bright, elongated spots close to the cell membrane and indicated by white arrows. WT: 4RepCT, RGD: RGD-4RepCT, IKVAV: IKVAV-4RepCT, CTRL: cell culture glass.

Immunofluorescence staining for detection of vinculin (clone V9131, Sigma-Aldrich) in combination with filamentous actin (Phalloidin, Invitrogen) was used to identify focal adhesions, i.e. actual contact spots between the cells and the material, as described in Example 7 above. Effect on apoptosis will be evaluated with EnzChek Caspase3 Assay (Molecular Probes). Living cells were detected with Alamar blue (Molecular Probes) as described in Example 7 above.
Results Primary human keratinocytes were cultured for 4 days on 4RepCT film with or without cell binding motifs. The cells survived and increased in cell numbers between day 1 and 4 (FIG. 44). They showed the characteristic morphology of keratinocytes on all materials during the full culture period (FIG. 45). Focal adhesions were detected on wild type, RGD and IKVAV films (analysed at day 4), indicating integrin-mediated adhesion to the tested materials (FIG. 46). The results were independent of addition of serum before seeding, thus, the cells bound to the material under strictly serum-free conditions.

Example 9

Primary Hepatocytes on Recombinant Spider Silk

The liver is an essential organ with unique functions. Currently, cases of acute liver failure, e.g. liver-based metabolic diseases and chronic liver disease, are rescued by either liver transplantation or liver cell therapy. Unfortunately, currently available hepatocyte therapy is not optimal, for example because many of the cells are lost and not engrafted during transplantation of hepatocytes. A scaffold, which serves as a host for hepatocytes and keeps them in place, could pre-engraft these cells prior to transplantation. This opens a new way of transplanting hepatocytes.
Experimental Material Rodent hepatocytes were isolated by digestion of collagenase treated liver by continuous mechanic shaking, separated and cultured in RPMI-1640 medium supplemented with 10% FBS.

Figure 47:
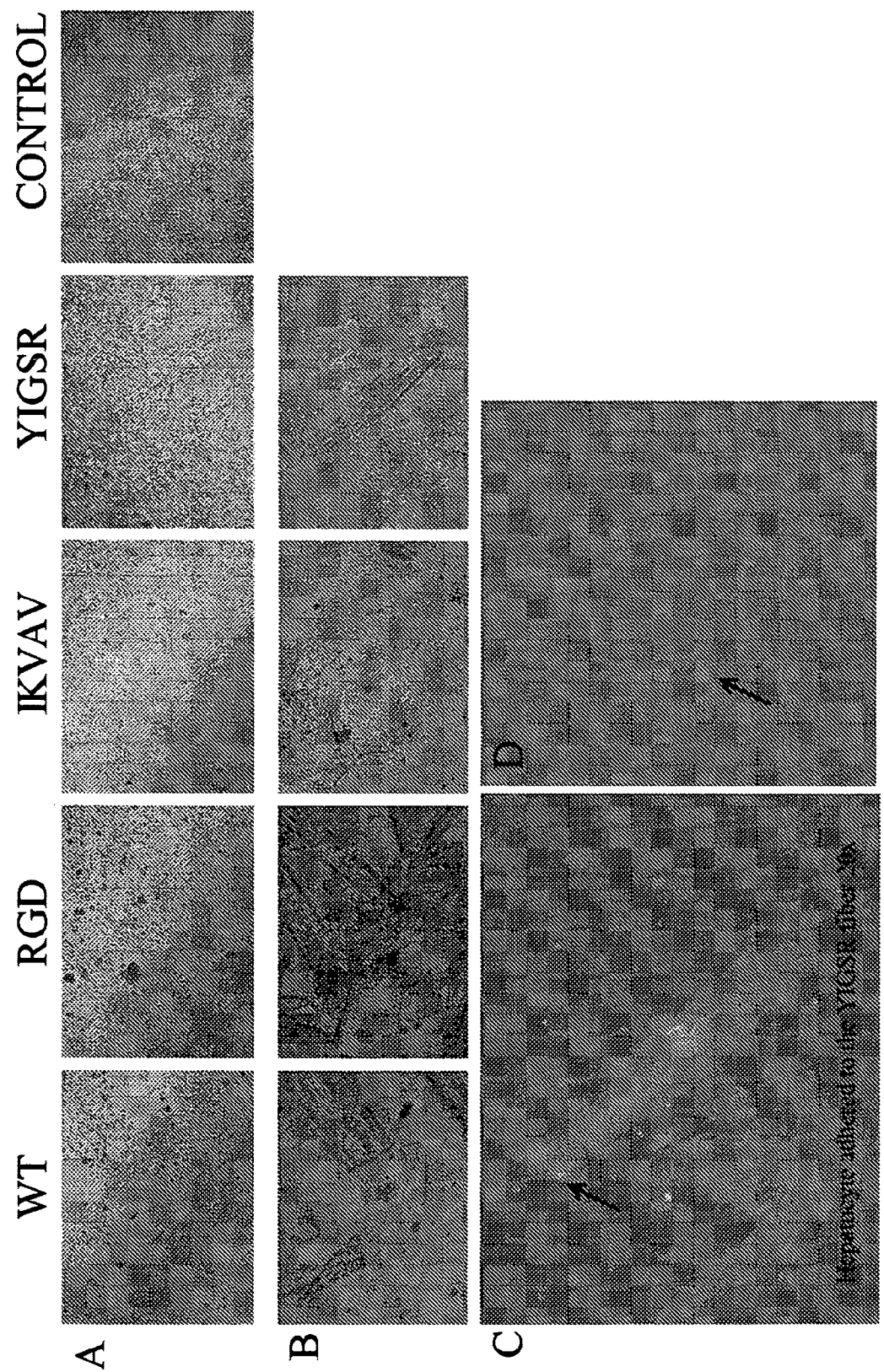
FIG. 47 is a set of photographs showing adherence of hepatocytes to 4RepCT film and fiber (panels A and B, respectively). Close interaction between hepatocyte and the fiber scaffold can be seen in C and D (n=1, experiment done in hexaplicates).

The recombinant spider silk protein 4RepCT described in previous Examples was used, both as wild type and in the form of variants modified by incorporation of different extracellular matrix related cell-binding motifs (e.g. RGD, IKVAV, YIGSR and RGE), and was prepared essentially as described in Hedhammar et al (2008), supra, in the form of scaffold structures prepared as described in Example 1.
Cell Culture:

Rodent hepatocytes in combination with 4RepCT scaffolds were cultured in supplemented RPMI-1640 medium.
Assessment of Survival of Hepatocytes:

The cells were plated on fiber and film scaffolds with incorporation of different extracellular matrix related cell-binding motifs (e.g. RGD, IKVAV, YIGSR and RGE). Cell morphology and survival was assessed over time in culture.
Results Hepatocytes adhered to fiber and film scaffolds (FIG. 47).
The hepatocytes were also able to survive in culture with 4RepCT.

Example 10

Recombinant Spider Silk Protein Scaffolds for Tissue Engineering

The experiment is expected to show that 4RepCT scaffolds enable regeneration of axons in spinal cord injuries in vivo. Both 4RepCT scaffolds without seeded cells and 4RepCT scaffolds combined with the engraftment of human neural cells and human oligodendrocyte progenitor cells are employed. Histological and behavioral analysis is used to document the results.
Materials and Methods
Animal Surgery The weight of rats is 170-200 g at the time of surgery. Animals are injected with Atropin (0.05 mg/kg i.p., NM Pharma AB) 30 minutes before surgery. Rats are anesthetized with a mixture of Hypnorm (fentanyl citrate, 0.22 mg/kg, and fluanisome, 6.8 mg/kg, Janssen Pharmaceutical) and Dormicum (midazolam, 3.4 mg/kg, Hoffman-La Roche). Body temperature of the rats is monitored and kept at 38° C. throughout the surgical procedure.

Lumbar spinal cords are surgically exposed by partial laminectomy and treated with a few drops of Xylocain (lidocain hydrochloride, 20 mg/ml, AstraZeneca Sweden AB) on the exposed spinal cord surface prior to the spinal cord injury.

Transection of the cord is performed by cutting the spinal cord with a scalpel. Through careful visual inspection, the surgeon assures that the rostral and caudal ends are completely separated, and slightly retracted. After lesioning the cord, a layer of LYOPLANT™ (B/Braun Aesculap AG) is placed on the spinal cord as dura substitution before the wound is sutured. The rats are subcutaneously injected twice with 3 ml Ringer/glucose (2.5%) before and after surgery. After surgery, the rats are given intramuscular injections of Temgesic (buprenorphin, 7 µg/kg, Reckitt & Colman) twice a day for four days. The urinary bladders are emptied manually twice daily, and Borgal (trimetoprim sulfa, 15 mg/kg s.c., Intervet International B.V.) is given if signs of urinary infection appear.

A 2-3 mm long bundle of 4RepCT fibers, for example prepared as described in the previous Examples (with or without additional peptide motifs such as RGD, RGE, IKVAV and YIGSR or using another variant of a spidroin protein, e.g. NT4RepCTHis), is placed in the gap of the spinal cord, either at the time of injury or one week after injury. In the acute implantation paradigm, a bundle of 4RepCT fibers is cut to fit the gap of the cut spinal cord, and gently placed in contact with the spinal cord stumps rostral and caudal to the implant, with the 4RepCT fibers in the same axis as the spinal cord. The LYOPLANT™ dura substitution is thereafter placed over the 4RepCT implant.

In case the 4RepCT fiber bundle is implanted one week post-injury, the animal is anesthetized, the wound reopened and the spinal cord exposed. After trimming the rostral and caudal stumps of the cord, the fiber bundle, cut to fit the gap, is placed in the same axis as the spinal cord to ascertain contact between the fibers and the spinal cord tissue rostral and caudal to the implant. The wound is closed as described above.

Co-Implantation of Human Immature Cells

In a similar experiment, implantation of 4RepCT fibers as described above is combined with engraftment of human neural stem cells and human oligodendrocyte progenitor cells. The cells are derived from human routine abortions, according to procedures approved by the Regional Ethical Committee, and after written consent from the abortion-seeking woman.

After in vitro culture of the appropriate cells according to proprietary procedures, a suspension of 100,000-500,000 cells in a minimal volume of DM EM-F12 without growth factors is injected into the 4RepCT fiber bundle, which is then used as described in the previous section.

Behavioral Assessment

To study hind-limb motor function, rats are allowed to move in an open field (150×64 cm) and observed for at least four minutes. The function of the hind-limbs, movement of joints, positioning of paws, weight bearing, coordination and toe clearance is evaluated and rated according to the Basso, Beattie, Bresnahan (BBB) Locomotor Rating Scale (Basso et al (1995), J Neurotrauma 12:1-21, for review see Basso (2004), J Neurotrauma 21:395-404). The tests are video recorded, and at least two independent observers blinded to the treatment evaluate each rat. Animals are evaluated preoperatively and 1, 2, 6, 12 and 18 weeks post surgery.

Tracing of Neuronal Outgrowth

Anterograde tracing is performed by injecting biotinylated dextrane amine (BDA, Neurotrace) at multiple sites in the parietal cortex for one week according to the manufacturer's description. Retrograde tracing is accomplished by injection of Fluoro-gold in the spinal cord 3-5 mm caudal of the lesion. BDA is visualized in the spinal cord caudal of the injury, to visualize cortico-spinal descending axons crossing the spinal lesion, while Fluoro-gold-labeled neurons are screened for in nucleus ruber of the brainstem, as evidence for regrowth of descending rubro-spinal neurons.

Morphological Analysis

After the last behavioral assessment at 18 weeks post-lesion, the rats are given a lethal dose of intravenous sedatives and perfused through the ascending aorta with 100 ml $Ca^{2+}$-free Tyrode's solution, followed by 400 ml of phosphate-buffered 4% paraformaldehyde (PFA, Merck). The entire brain stem and 4-5 cm of the vertebral column including the lesion are dissected out, post-fixed for 2 hours in the same fixative and cryo-preserved in 10% sucrose at 4° C. for at least 24 h. The spinal cord is then carefully dissected out of the vertebral column, the cord and the brainstem embedded in Tissue-Tek, frozen, sectioned at 10 µm in a cryostat and mounted on gelatin-coated slides.

For immunohistochemical analysis, the following primary antibodies are used: human-specific rabbit anti-heat shock protein 27, rabbit anti-nestin, rabbit anti-β-tubulin type II, mouse monoclonal human-specific anti-glial fibrillary acidic protein, rabbit anti microtubule-associated protein 2. Primary antibodies are diluted in 0.1 M phosphate buffer with 0.3% Triton X-100 (TPBS). The secondary antibodies used are conjugated to Cy3 (Jackson ImmunoResearch Laboratories Lab. Inc) or Alexa 488 (Molecular Probes). Sections are treated with 1.5% normal goat serum (Sigma) at room temperature for 30 minutes, incubated with primary antibodies at 4° C. over night followed by rinsing and two hour incubation with secondary antibodies at room temperature. All sections are counterstained with nuclear marker Hoechst 33342 (30 µg/ml, Molecular Probes), and mounted with poly vinyl-alcohol (0.1 mg/ml, Sigma) in DABCO (1,4-diazabicyclo [2.2.2]octane, 0.03 mg/ml, Sigma). The immunolabeled tissue sections are studied in a fluorescence microscope (Zeiss Axiophot), for quantitative analyses, images are captured using a CCD camera (Hamamatsu ORCA-ER) and the OPENLAB™ software for Macintosh (Improvision).

Example 11

Recombinant Spider Silk Protein Scaffolds for Support of the Regeneration of Axons in Organotypic Cultures This experiment will show that 4RepCT scaffolds can support and guide the regeneration of axons. Pieces of the spinal cord and brainstem are maintained in cultures ex vivo. By applying a scaffold of 4RepCT that connects two such tissue pieces, regenerating axons will be provided sufficient support to bridge the gap. The experiment will give an indication of the usefulness of 4RepCT scaffolds to support axonal outgrowth and restoration of damaged tissue in spinal cord injuries in vivo.

An organotypic culture of the brain stem and the cervical region of the cord is prepared. Brains and spinal cords are collected from early pre-natal and post-natal Sprague-Dawley (SD) rats. Sections in the sagittal plane through the brain stem and cervical region of the spinal cord are made using a vibratome. The dissected tissue is placed on membranes (MILLICELL™-CM; Millipore, Billerica, Mass., USA), in 1 ml of serum-based medium (50% basal medium Eagle with Earle's Salts (BME; Sigma, St. Louis, Md., USA), 25% heat inactivated horse serum (Gibco, Grand Island, N.Y., USA), and 25% Earle's Balanced Salt Solution (EBSS; Sigma), 1 mM L-glutamine and 0.5% d-glucose) in a 6-well tissue culture plate in a humidified atmosphere with 5% $CO_2$ at 37° C. The tissue sections are incubated for 7-14 days, the medium replaced every 3 days. At the time of injury, a transection of the upper cervical spinal cord is made with a razor blade. The tissue is inspected in an inverted microscope to ensure complete separation of the two parts of the explant.

A bundle of 4RepCT fibers, prepared as described in previous Examples (with or without additional peptide motifs such as RGD, RGE, IKVAV and YIGSR or using another variant of a spidroin protein, e.g. NT4RepCTHis), is placed in the gap between the tissue pieces. The cultures are incubated for another 14 days, before being fixed by immersion in phosphate-buffered 4% paraformaldehyde (PFA, Merck) for 2 hours and cryo-preserved in 10% sucrose at 4° C. for 24 h.

For immunohistochemical analysis, the following primary antibodies are used: human-specific rabbit anti-heat shock protein 27, rabbit anti-nestin, rabbit anti-β-tubulin type II, mouse monoclonal human-specific anti-glial fibrillary acidic protein, rabbit anti microtubule-associated protein 2. Primary antibodies are diluted in 0.1 M phosphate buffer with 0.3% Triton X-100 (TPBS). The secondary antibodies used are conjugated to Cy3 (Jackson ImmunoResearch Laboratories Lab. Inc) or Alexa 488 (Molecular Probes). Fixed cultures are treated with 1.5% normal goat serum (Sigma) at room temperature for 30 minutes, incubated with primary antibodies at 4° C. over night followed by rinsing and two hour incubation with secondary antibodies at room temperature. All tissues are counterstained with nuclear marker Hoechst 33342 (30 µg/ml, Molecular Probes), and mounted with poly vinyl-alcohol (0.1 mg/ml, Sigma) in DABCO (1,4-diazabicyclo [2.2.2]octane, 0.03 mg/ml, Sigma). The immunolabeled tissue sections are studied in a fluorescence microscope (Zeiss Axiophot) for quantitative analyses, images are captured using a CCD camera (Hamamatsu ORCA-ER) and the OPENLAB™ software for Macintosh (Improvision).

49

The results are predicted to indicate that 4RepCT scaffolds can guide regeneration of injured axons.

Example 12

Human Embryonic Stem Cells on Recombinant Spider Silk

The experiment explores further the feasibility of culturing human embryonic stem cells on a recombinant spider silk material, building on the study reported as Example 2 above.

Materials and Methods

Standard six-well tissue culture plates were prepared. In the plates, three wells contained film of one of the following 4RepCT variants: RGD-4RepCT, RGE-4RepCT, IKVAV-4RepCT, YIGSR-4RepCT and NT4RepCTHis, while the remaining three wells of each plate were empty. All films of 4RepCT with peptide motifs and of NT4RepCTHis were prepared essentially as described in Example 1. In total, 15 plates were included in the experiment (representing triplicates of each 4RepCT variant). The plates were kept dry at room temperature until further use.

In preparation for the experiment, the tissue culture plates were UV irradiated for 30 minutes in a Class II microbiological safety cabinet. The three empty wells in each plate were then coated with CELLstart™ CTS™ (Invitrogen; cat no A10142-01), as per manufacturer's protocol.

Human embryonic stem cells (RCM-1, De Sousa et al, Stem Cell Res 2:188-197; Roslin Cells, Edinburgh, UK) were cultured on CELLstart™ with the serum and feeder free medium STEMPRO® hESC SFM—Human Embryonic Stem Cell Culture Medium (Invitrogen; cat no A1000701), as per manufacturer's protocol. The cells were passaged at a ratio of 1:6 from a 90% confluent well using STEMPRO® EZPassage™—Disposable Stem Cell Passaging Tool (Invitrogen; cat no 23181-010) as per manufacturer's protocol.

Wells were washed with PBS, and medium was placed in all wells and preincubated prior to cell seeding. Cells at passage 60 were seeded into all wells of five six-well plates (representing the five different variants) at the recommended density, and care was taken not to disturb cells after seeding. All wells were cultured with STEMPRO® hESC SFM as per manufacturer's protocol. Incubation was performed in a standard culture incubator at 37° C., 5% $CO_2$ in air, at 95% humidity. Cells were observed daily and 100% medium exchanged every 48 hours. All medium was pre-equilibrated to incubator conditions for two hours prior to exchange feeding.

Cells were passaged after 16 days, and again after 6 more days, onto the remaining two six well plates of the respective variants. The passaging regime for these two time points involved a method established by Roslin Cellabs for the single cell dissociation of human embryonic stem cells. Single cell dissociation was achieved using TrypLE Select (Invitrogen cat. no. A12177 (100 ml 10×)) as per manufacturer's instructions with a pre-treatment for 1 h using a ROCK inhibitor (ROCK inhibitor/Y27632; FluoroChem cat. no. 047265) as per the manufacturer's instructions (Watanabe et al (2007),Nat Biotechnol 25, 681-686). This has been shown to be essential for the successful growth of embryonic stem cells post enzymatic passaging. Control and trial cells were treated identically and all were subsequently seeded at equivalence.

After 24 h of the third passage of the study, wells were stained with Sigma-Aldrich: alkaline phosphatase (AP), Leukocyte (Sigma-Aldrich; Ref 86R-1 KT, Lot 019K4349) as per manufacturer's protocol.

Results

Selected images from the cell culture experiments are presented as FIGS. 48-52.

No differences between the various 4RepCT variants were observed. Initially, cells were non-adherent "clumps" with a small degree of adherence. Growth was much slower than that seen in the control wells, which could be a consequence of the cell line adapting to the 4RepCT variants, as seen in Example 2. It is often the case that embryonic stem cell lines will go through a phase of transition or lag, prior to establishing again on a new matrix or indeed in a new medium composition. These Embryonic Body (EB) structures did eventually adhere to the matrix, and from these EB masses, cells were seen to grow and expand, which suggests adaptation to the new matrix as illustrated by photographs of cells in the first, second and third passage of the experiment (FIGS. 48-52).

Subsequent passaging resulted in improved morphology and growth.

Figure 50:
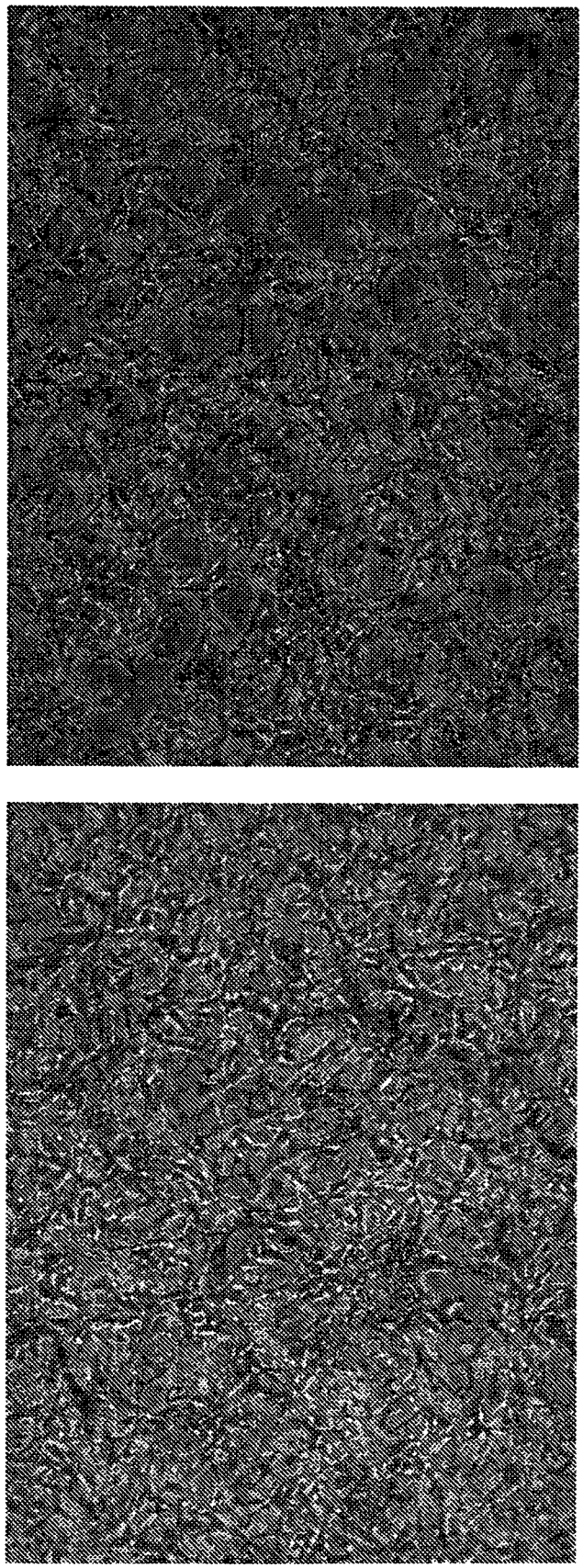
FIG. 50 is a pair of photographs showing the appearance of AP-stained hESC 24 hours post seeding in the third passage of the experiment described in Example 12 on respective coating. Left: Cellstart coating (control); Right: YIGSR-4RepCT film (Y). Positive AP staining appears in brown color (dark grey in picture).

As shown by alkaline phosphatase staining, the cells are, surprisingly, still exhibiting undifferentiated stem cell characteristics after 23 days of culture on the respective 4RepCT variants (FIGS. 50-52).

Conclusions

All control wells showed the characteristics and morphology as would be expected with this hESC line under the control culture conditions employed. The cell line showed signs of adaptation to all the 4RepCT variants. Initial adherence, growth and culture morphology was poor in the first passage on 4RepCT variants. However, subsequent growth and passaging resulted in colonies exhibiting the morphology characteristic of an undifferentiated cell, with positive alkaline phosphatase staining for all variants.

This study of hESC culture on 4RepCT variants surprisingly indicates that the variants allow culturing of hESCs and that they are suitable for maintaining the cells' stemness, for example with respect to morphology, growth characteristics and Alkaline Phosphatase staining.

The invention claimed is:

1. A combination, comprising:
   eukaryotic cells; and
   a cell scaffold material;
   wherein
   said cell scaffold material comprises a polymer comprising a spider silk protein and a cell-binding motif, said spider silk protein consisting of from 140 to 600 amino acid residues and comprising
   a repetitive fragment of from 70 to 300 amino acid residues derived from the repetitive fragment of a spider silk protein;
   a C-terminal fragment of from 70 to 120 amino acid residues derived from the C-terminal fragment of a spider silk protein; and optionally
   an N-terminal fragment of from 100 to 160 amino acid residues derived from the N-terminal fragment of a spider silk protein,
   wherein said cell-binding motif is an oligopeptide coupled to the spider silk protein via at least one peptide bond, and wherein said oligopeptide cell-binding motif is a keratinocyte-specific cell-binding motif.

2. The combination according to claim 1, wherein said spider silk protein is selected from the group of proteins defined by the formulas REP-CT and NT-REP-CT, wherein NT is a protein fragment having from 100 to 160 amino acid residues, which fragment is a N-terminal fragment derived from a spider silk protein;

REP is a protein fragment having from 70 to 300 amino acid residues, wherein said fragment is selected from the group consisting of $L(AG)_nL$, $L(AG)_nAL$, $L(GA)_nL$, and $L(GA)_nGL$, wherein n is an integer from 2 to 10;

each individual A segment is an amino acid sequence of from 8 to 18 amino acid residues, wherein from 0 to 3 of the amino acid residues are not Ala, and the remaining amino acid residues are Ala;

each individual G segment is an amino acid sequence of from 12 to 30 amino acid residues, wherein at least 40% of the amino acid residues are Gly; and each individual L segment is a linker amino acid sequence of from 0 to 20 amino acid residues; and CT is a protein fragment having from 70 to 120 amino acid residues, which fragment is a C-terminal fragment derived from a spider silk protein.

3. The combination according to claim 1, wherein said oligopeptide is coupled to the N-terminal of the spider silk protein.

4. The combination according to claim 1, wherein said cell scaffold material is in a physical form selected from the group consisting of film, foam, fiber and fiber-mesh.

5. The combination according to claim 1, wherein said oligopeptide is coupled to the C-terminal of the spider silk protein.

* * * * *